United States Patent
Koo

(10) Patent No.: US 12,396,977 B2
(45) Date of Patent: Aug. 26, 2025

(54) COMPOSITION FOR TREATING DEGENERATIVE BRAIN DISEASES, CONTAINING 2-PENTYLFURAN AS ACTIVE INGREDIENT

(71) Applicant: DAEGU GYEONGBUK INSTITUTE OF SCIENCE AND TECHNOLOGY, Daegu (KR)

(72) Inventor: Jae Hyung Koo, Daegu (KR)

(73) Assignee: DAEGU GYEONGBUK INSTITUTE OF SCIENCE AND TECHNOLOGY, Daegu (KR)

( * ) Notice: Subject to any disclaimer, the term of this patent is extended or adjusted under 35 U.S.C. 154(b) by 874 days.

(21) Appl. No.: 17/622,505

(22) PCT Filed: Jun. 26, 2020

(86) PCT No.: PCT/KR2020/008347
§ 371 (c)(1),
(2) Date: Dec. 23, 2021

(87) PCT Pub. No.: WO2020/263012
PCT Pub. Date: Dec. 30, 2020

(65) Prior Publication Data
US 2022/0241237 A1    Aug. 4, 2022

(30) Foreign Application Priority Data
Jun. 27, 2019    (KR) ........................ 10-2019-0077257

(51) Int. Cl.
*A61K 31/341*    (2006.01)
*A23L 33/00*    (2016.01)
*A23L 33/10*    (2016.01)

(52) U.S. Cl.
CPC ............ *A61K 31/341* (2013.01); *A23L 33/10* (2016.08); *A23L 33/40* (2016.08); *A23V 2002/00* (2013.01)

(58) Field of Classification Search
CPC ....... A61K 31/341; A23L 33/10; A61P 25/28; A61P 25/00; A23V 2200/322
See application file for complete search history.

(56) References Cited

FOREIGN PATENT DOCUMENTS

| JP | H05-017471 A | 1/1993 | |
|---|---|---|---|
| KR | 10-2019-0009084 A | 1/2019 | |
| WO | WO-2014160940 A2 * | 10/2014 | ........... A61K 31/341 |
| WO | WO-2017/130933 A1 | 8/2017 | |

OTHER PUBLICATIONS

Loizzo, et al.; Food and Chemical Toxicology, v59, pp. 586-594; 2013 (Year: 2013).*
Olivera M. Mitrasinovic et al., 'Accelerated Phagocytosis of Amyloid-ß by Mouse and Human Microglia Overexpressing the Macrophage Colony-stimulating Factor Receptor,' *The Journal of Biological Chemistry*, vol. 277, No. 23, Aug. 16, 2002, pp. 29889-29896.
Syhre, M. et al., "Investigation into the production of 2-Pentylfuran by Aspergillus fumigatus and other respiratory pathogens in vitro and human breath samples", Medical Mycology, May 2008.
International Search Report for International Application No. PCT/KR2020/008347 dated Oct. 15, 2020.
Korean Office Action for Korean Application No. 10-2019-0077257 dated Jul. 13, 2020.

* cited by examiner

*Primary Examiner* — Jeffrey S Lundgren
*Assistant Examiner* — W. Justin Youngblood
(74) *Attorney, Agent, or Firm* — Sughrue Mion, PLLC

(57) ABSTRACT

The present invention relates to a composition for preventing or treating a degenerative brain disease, comprising 2-pentylfuran or a solvate thereof, a stereoisomer thereof or a pharmaceutically acceptable salt thereof as an active ingredient.

5 Claims, 55 Drawing Sheets

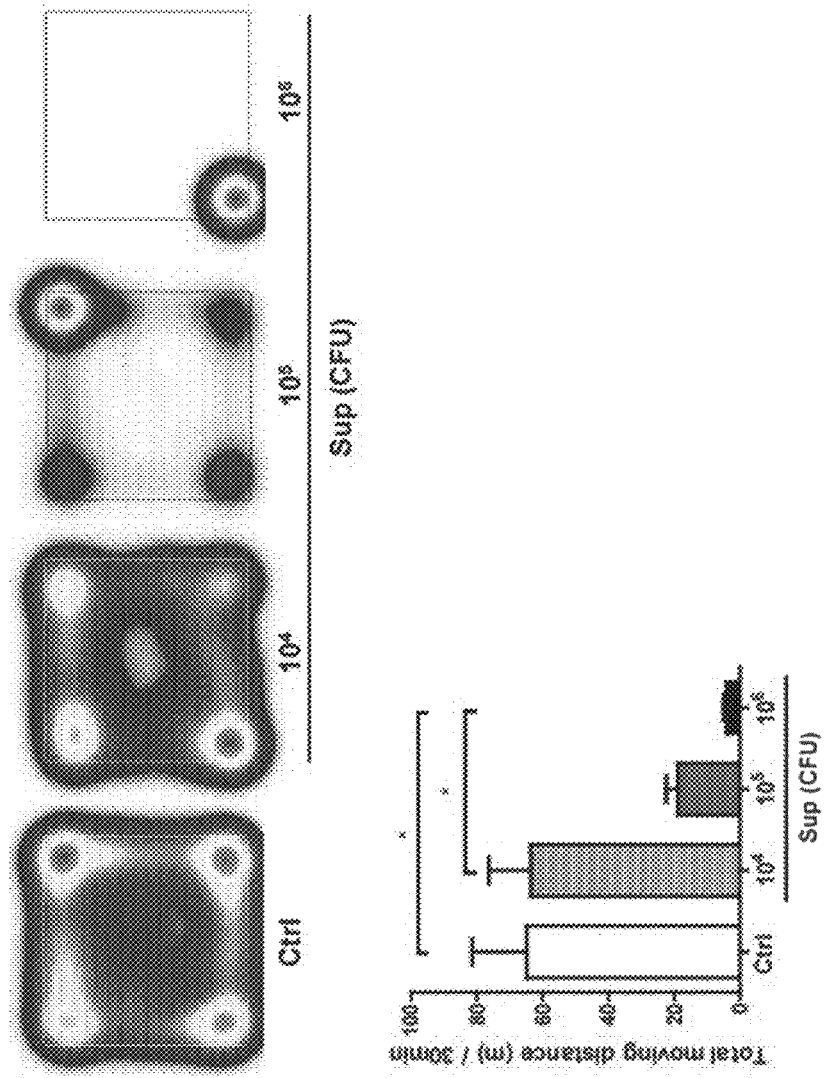
[FIG. 1]

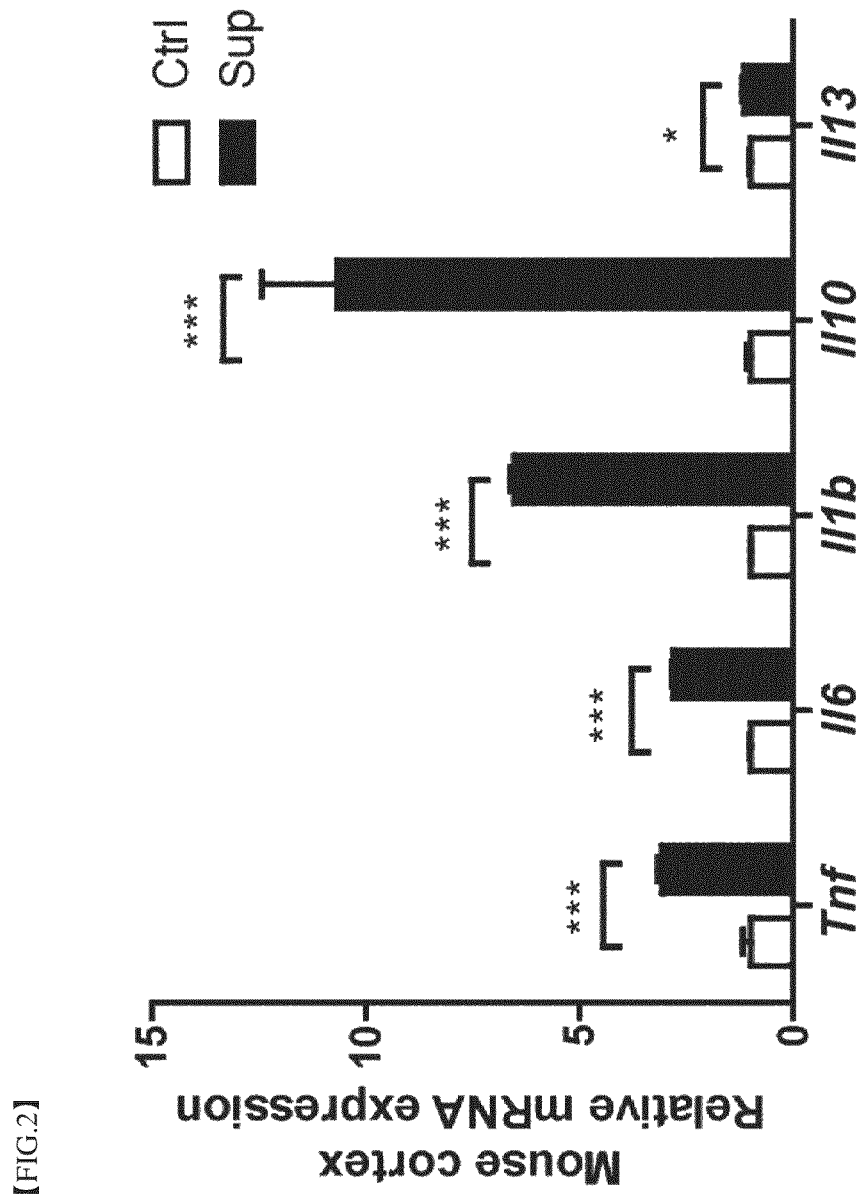
[FIG.2]

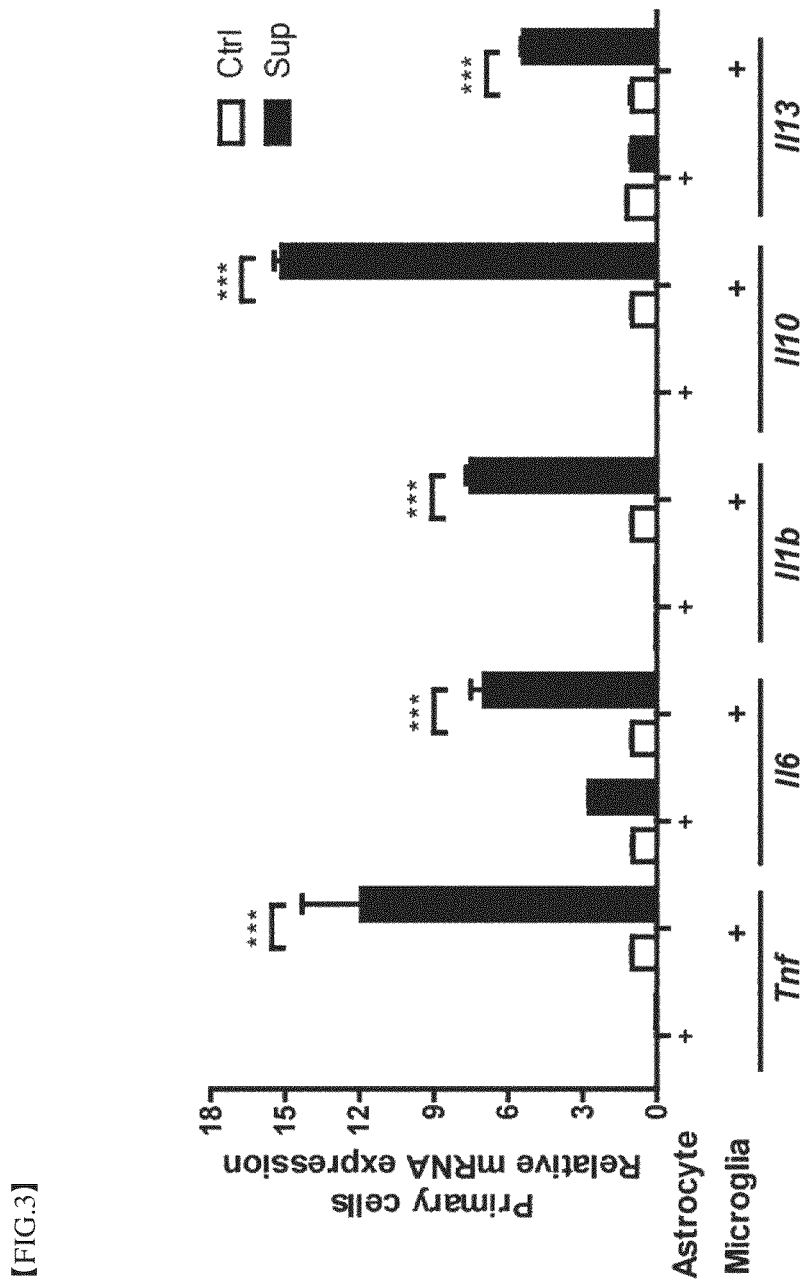
[FIG.3]

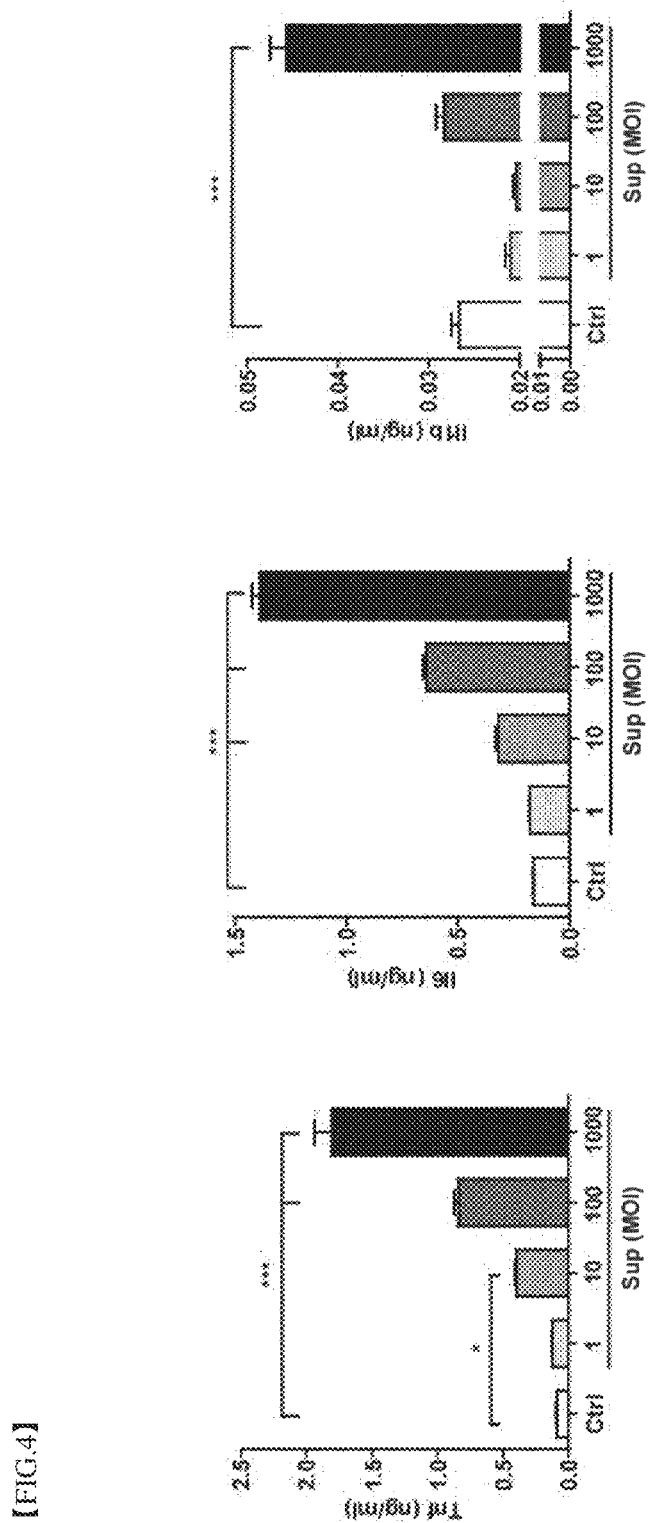
[FIG.4]

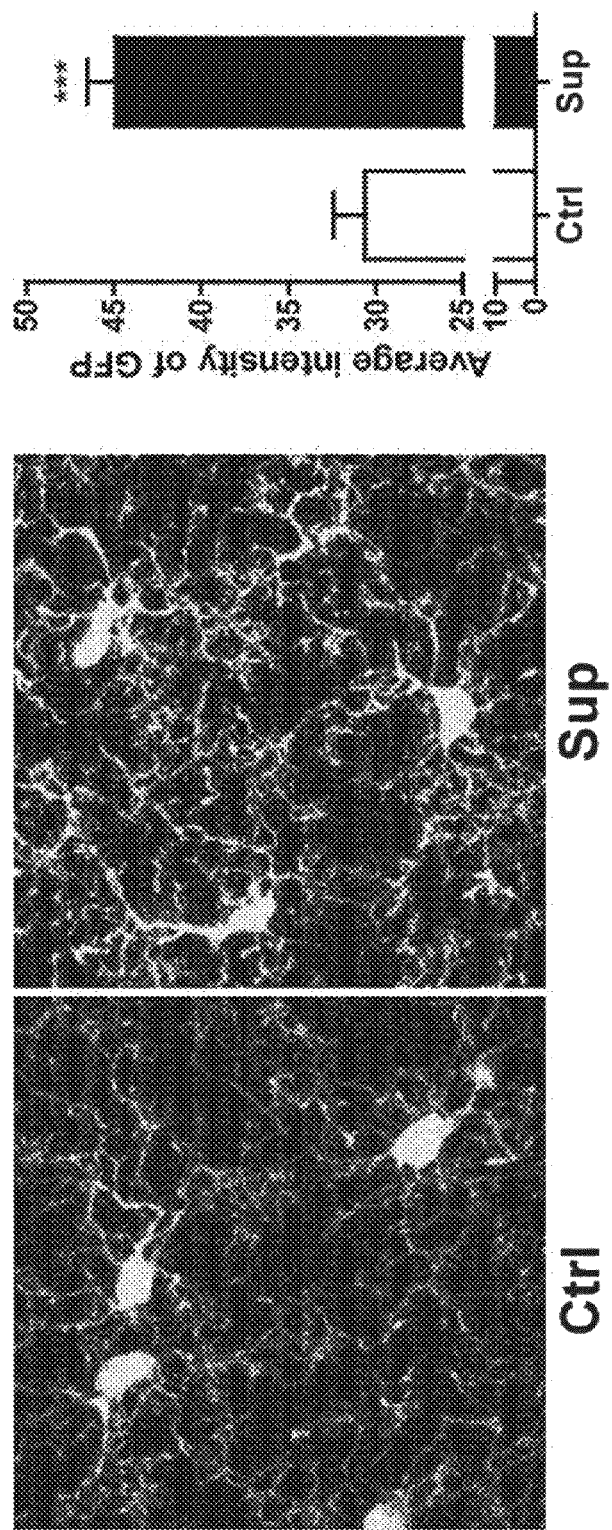
[FIG.5]

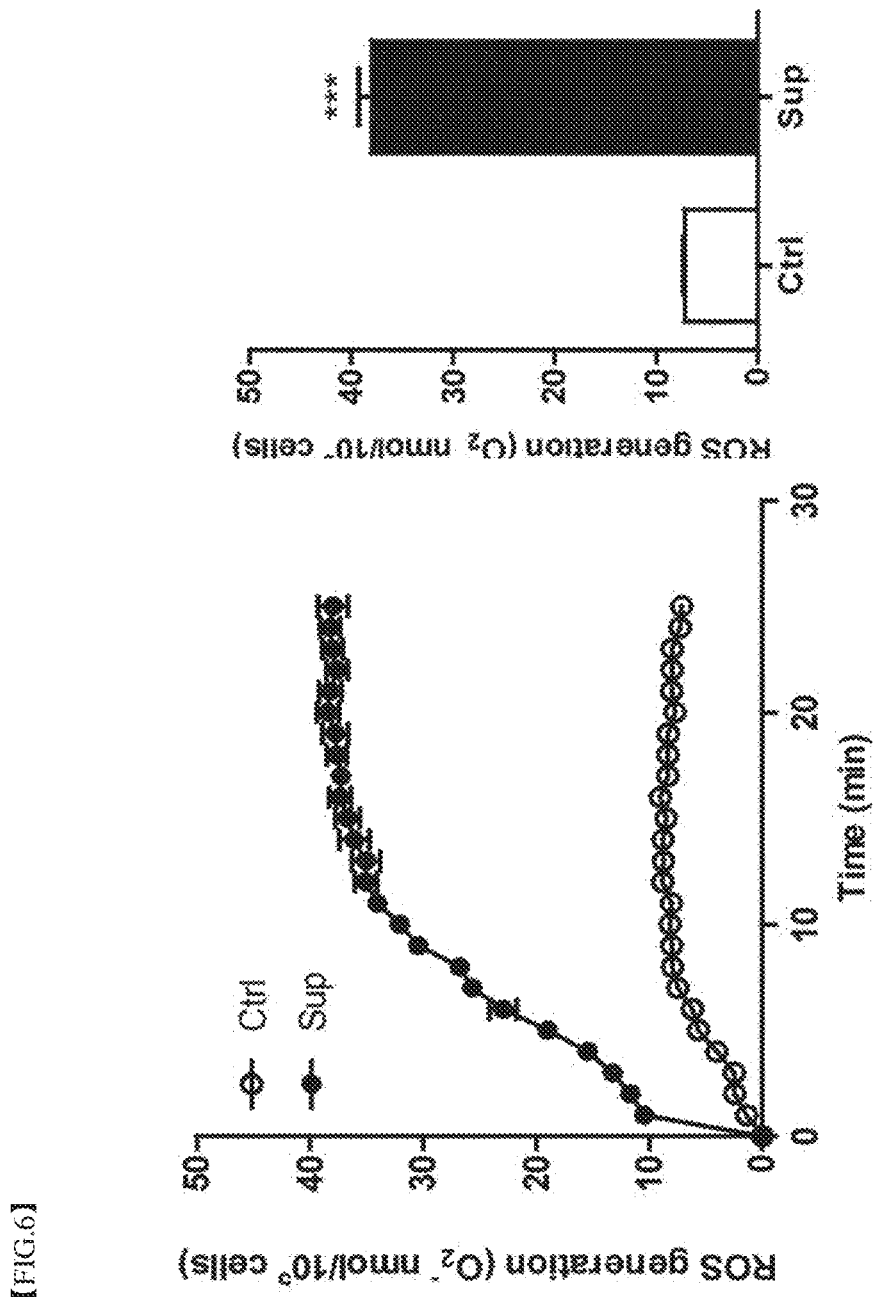
[FIG.6]

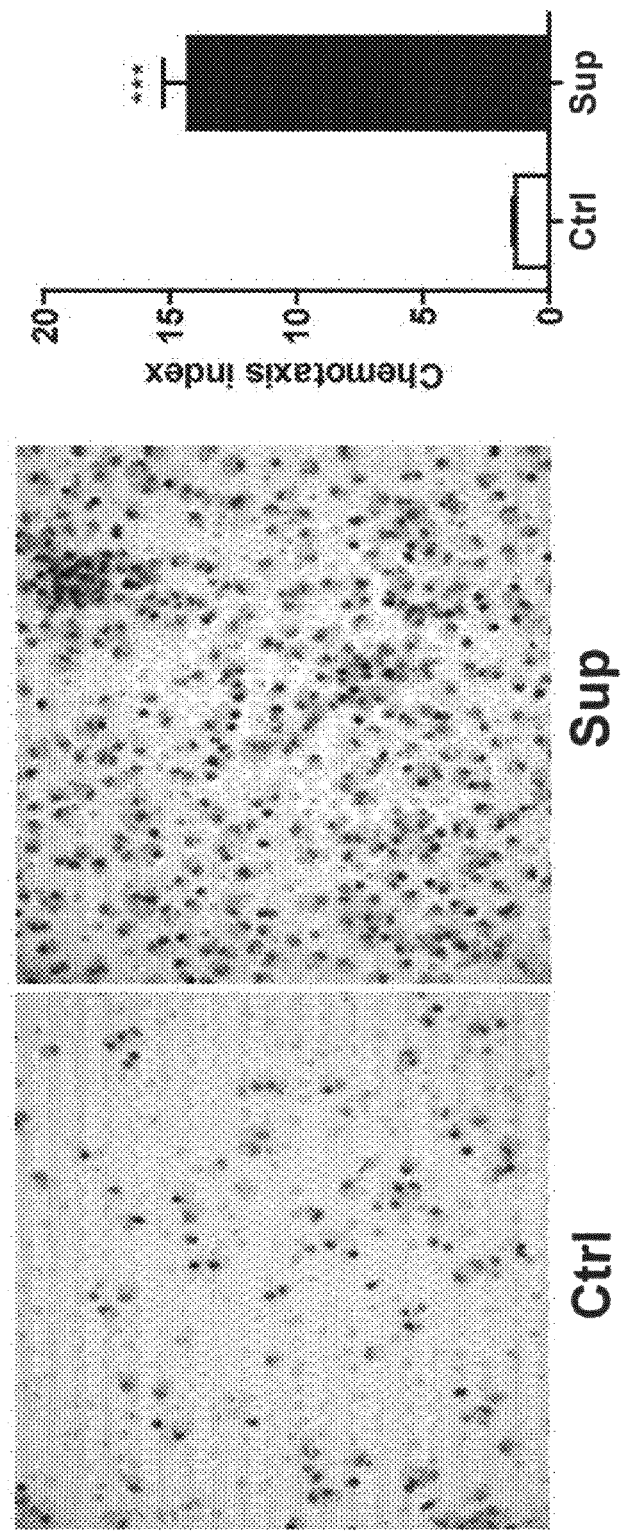
[FIG.7]

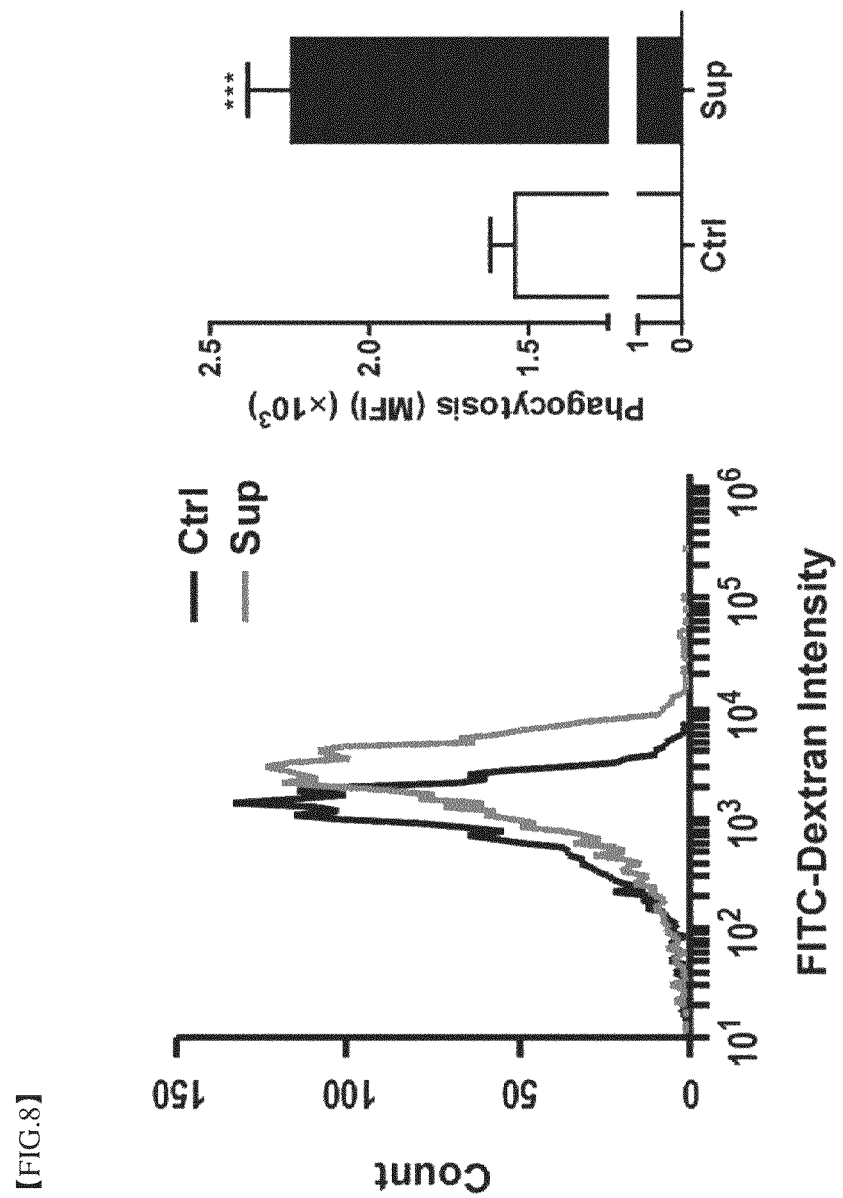
[FIG.8]

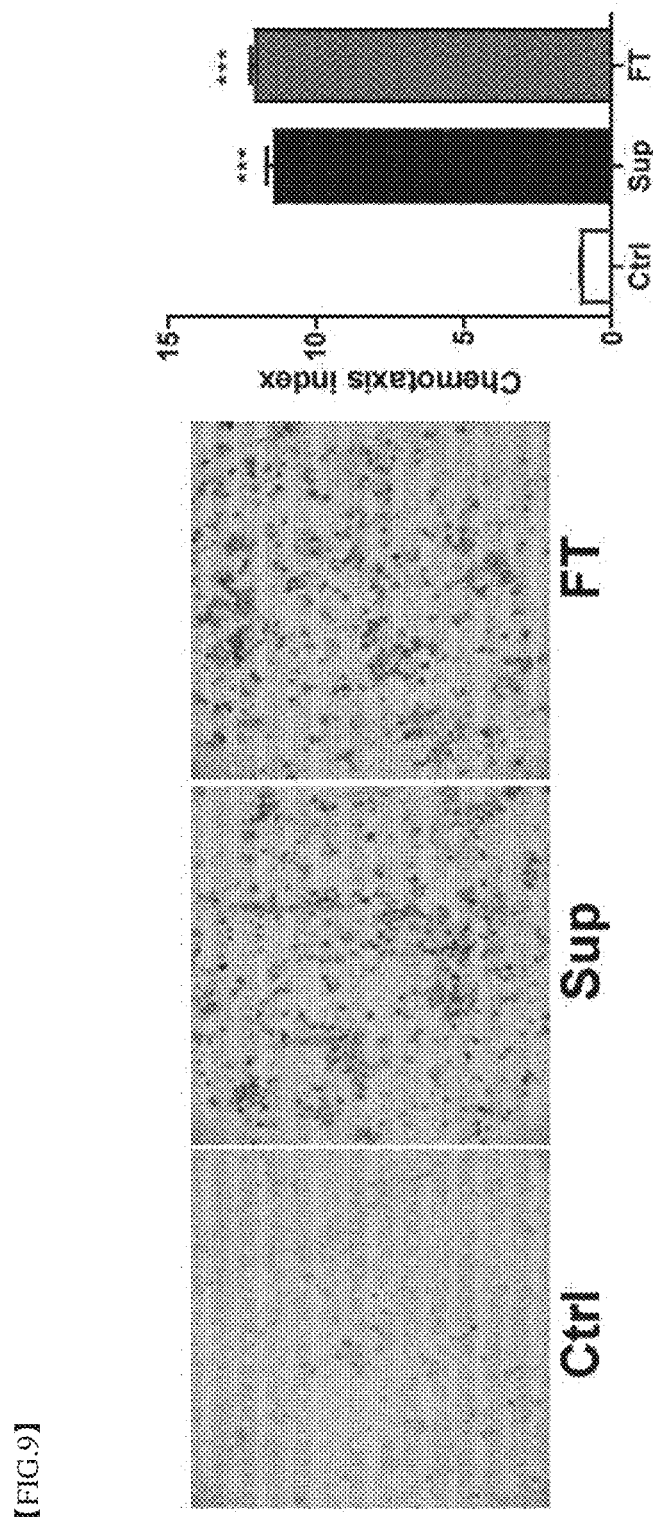
[FIG.9]

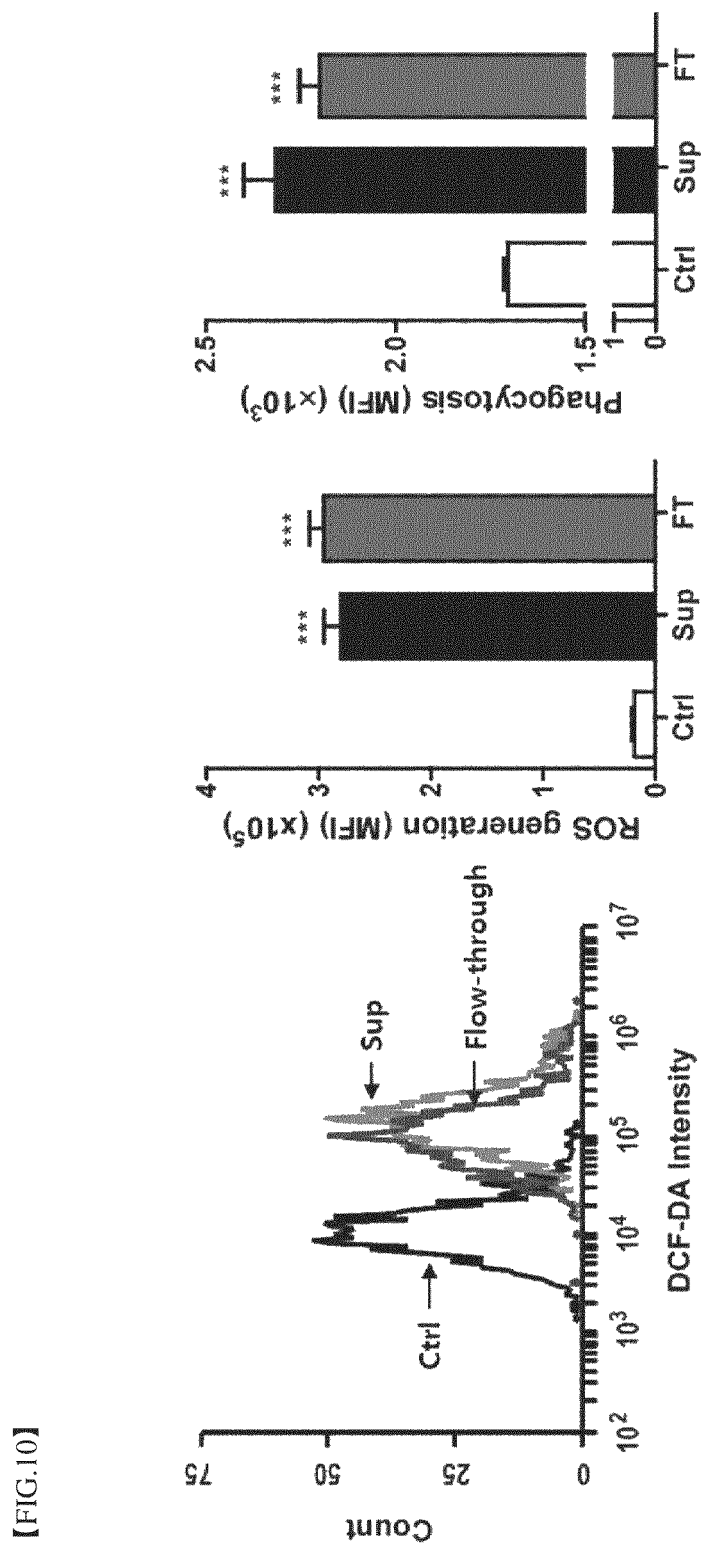
[FIG.10]

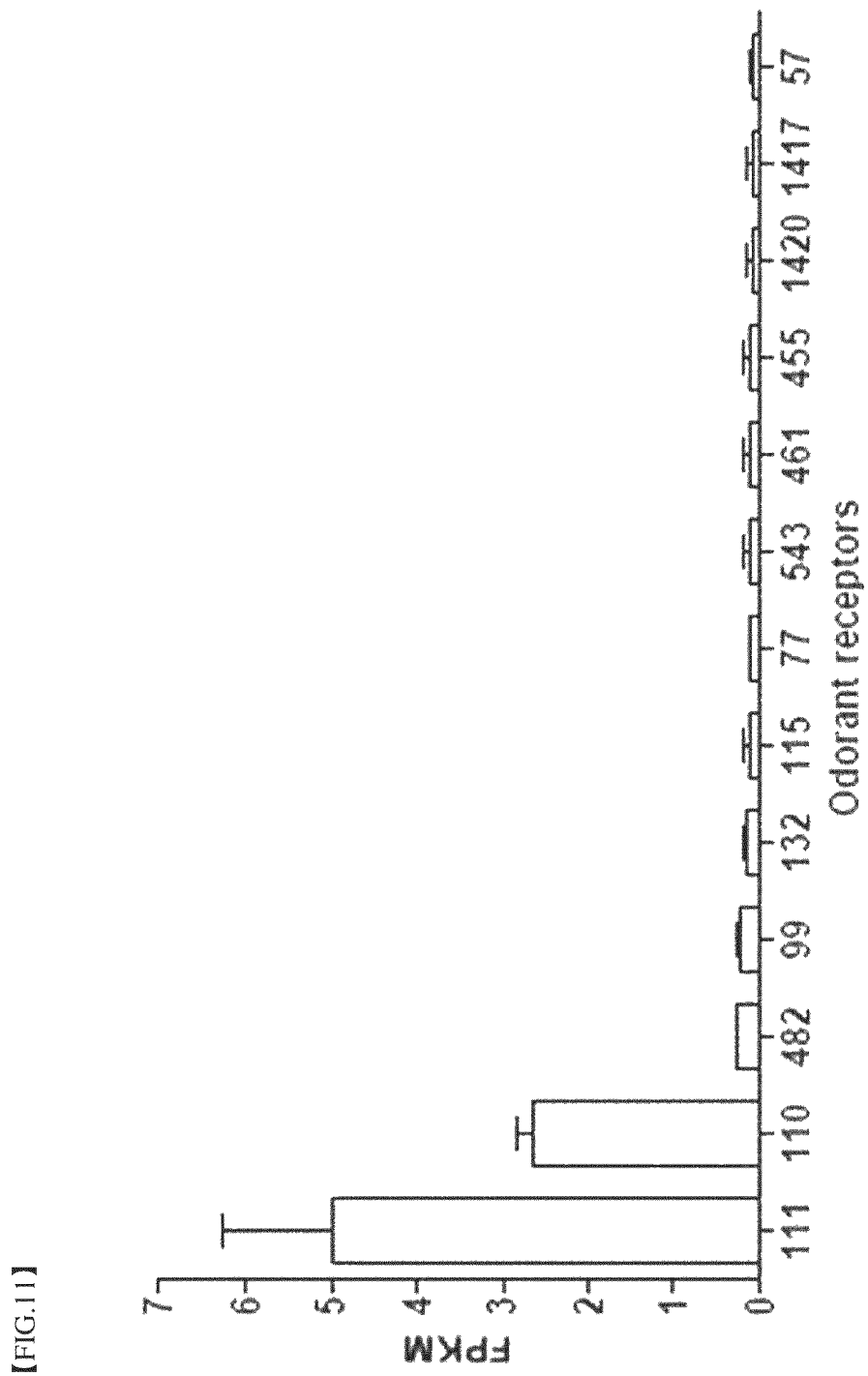
[FIG.11]

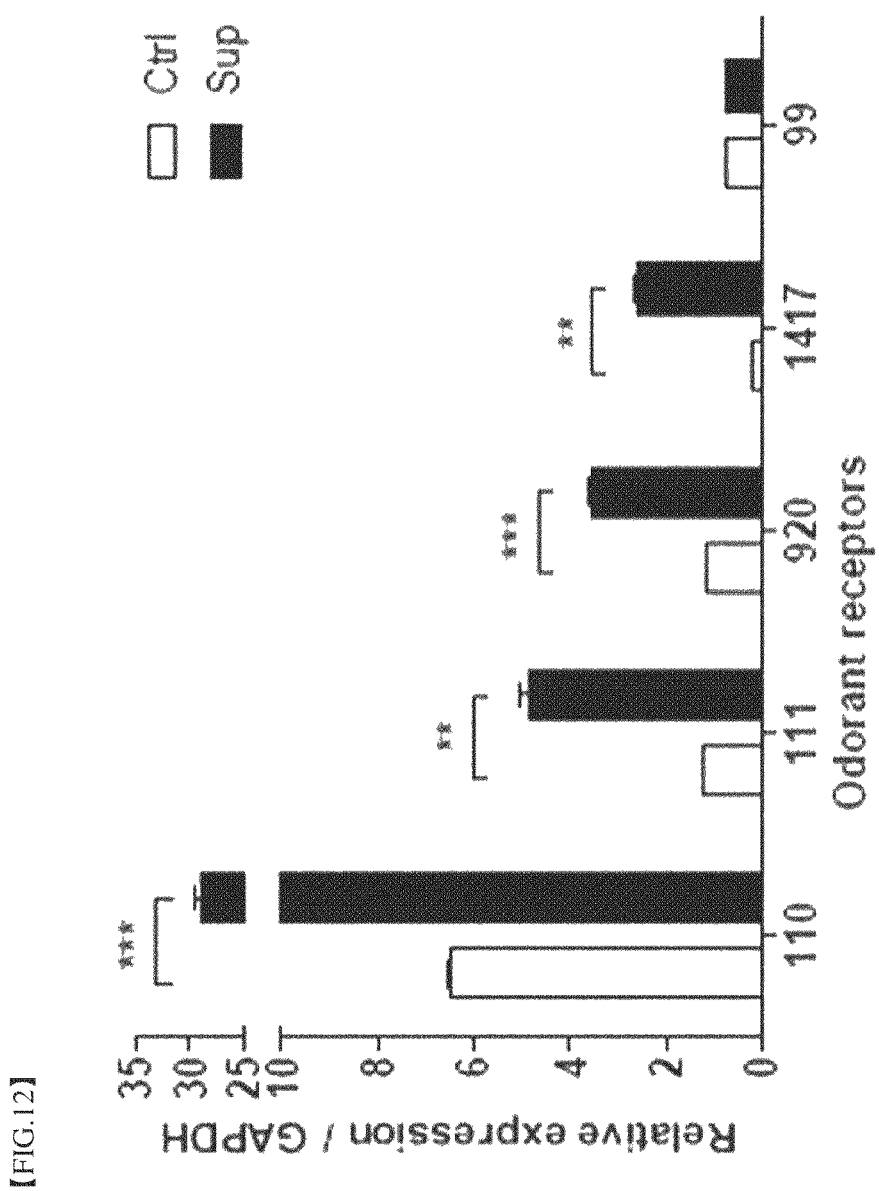
[FIG.12]

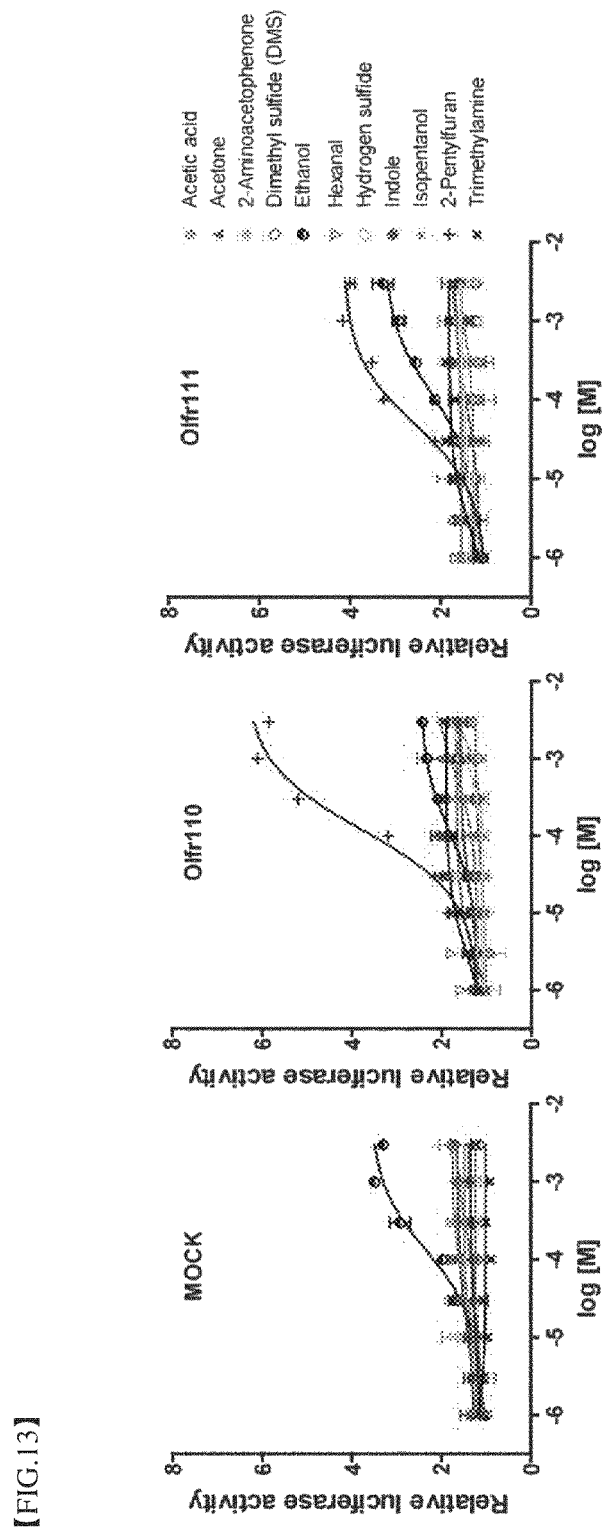
[FIG.13]

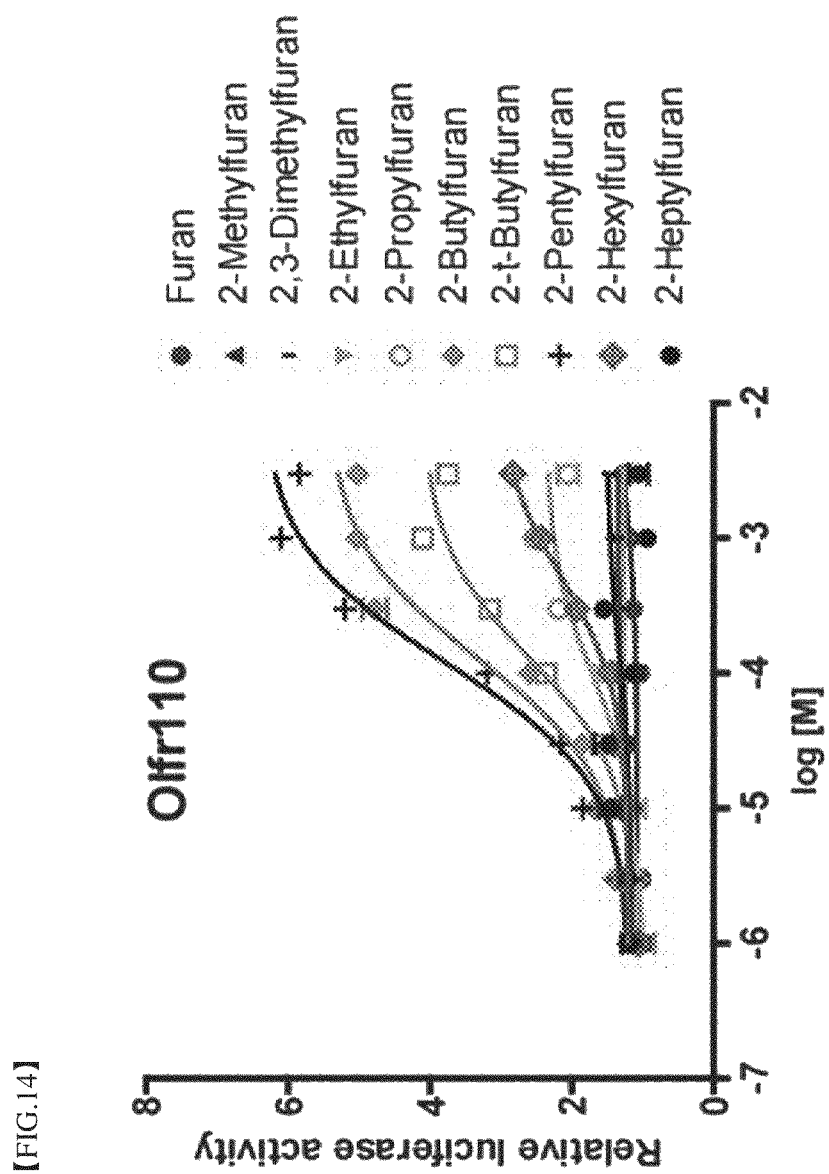
[FIG.14]

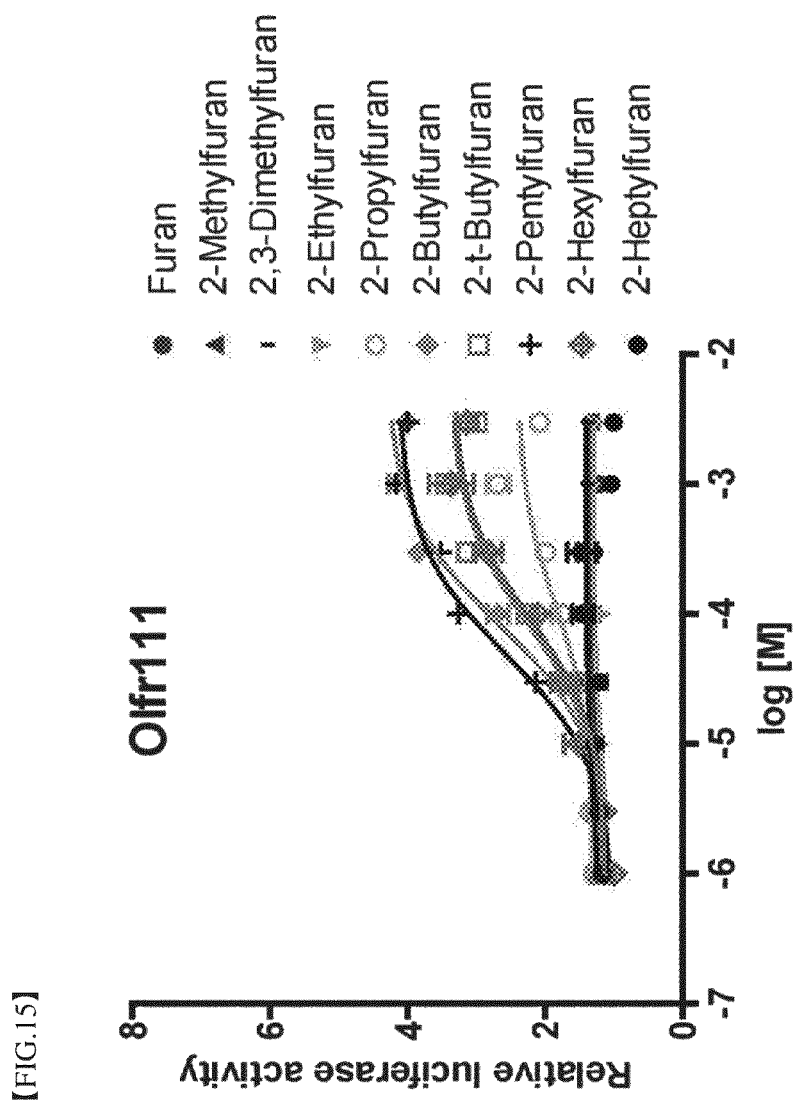
[FIG.15]

[FIG.16]
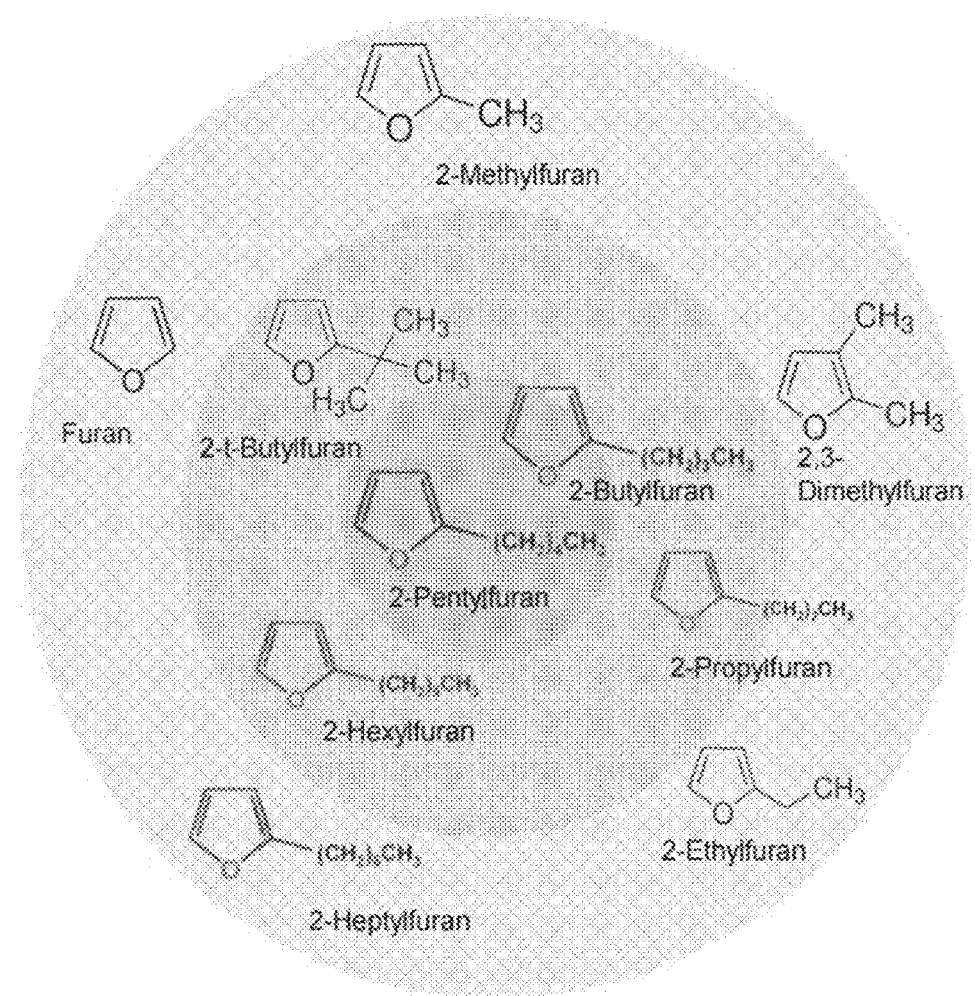

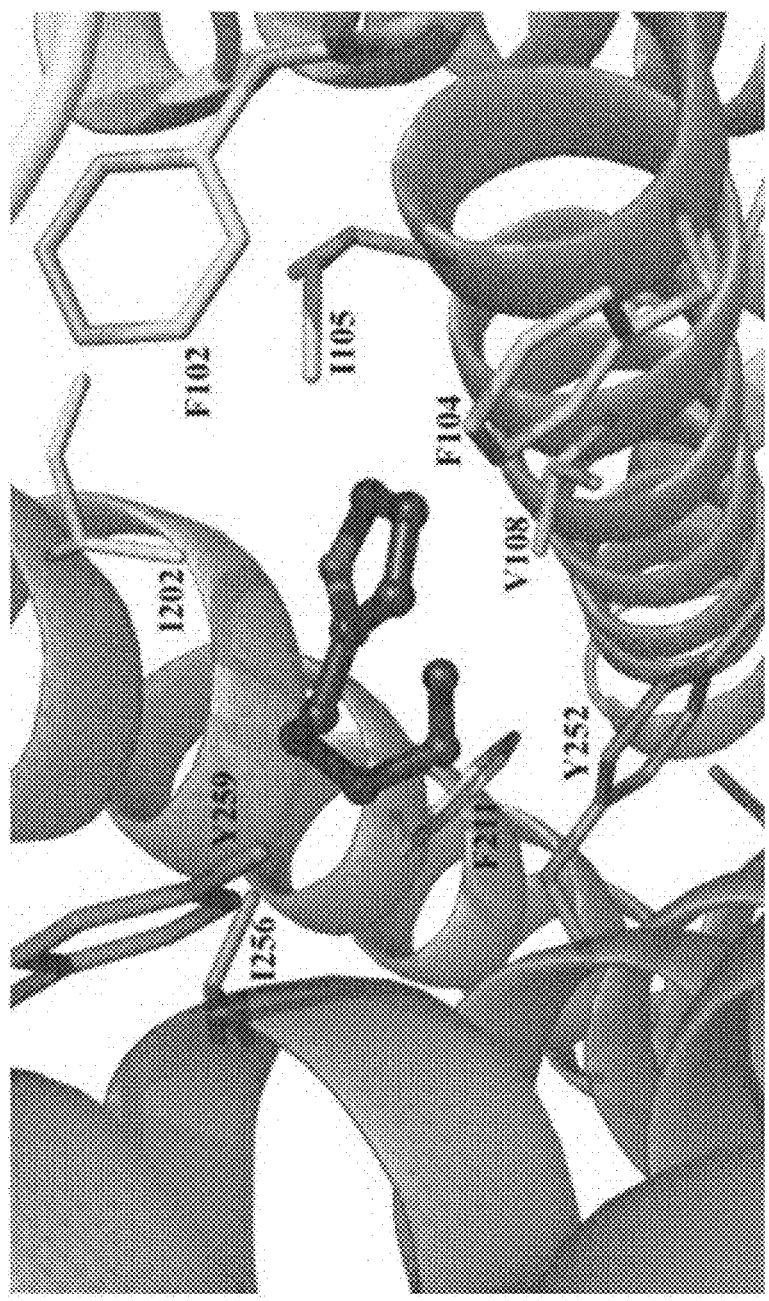
[FIG. 17]

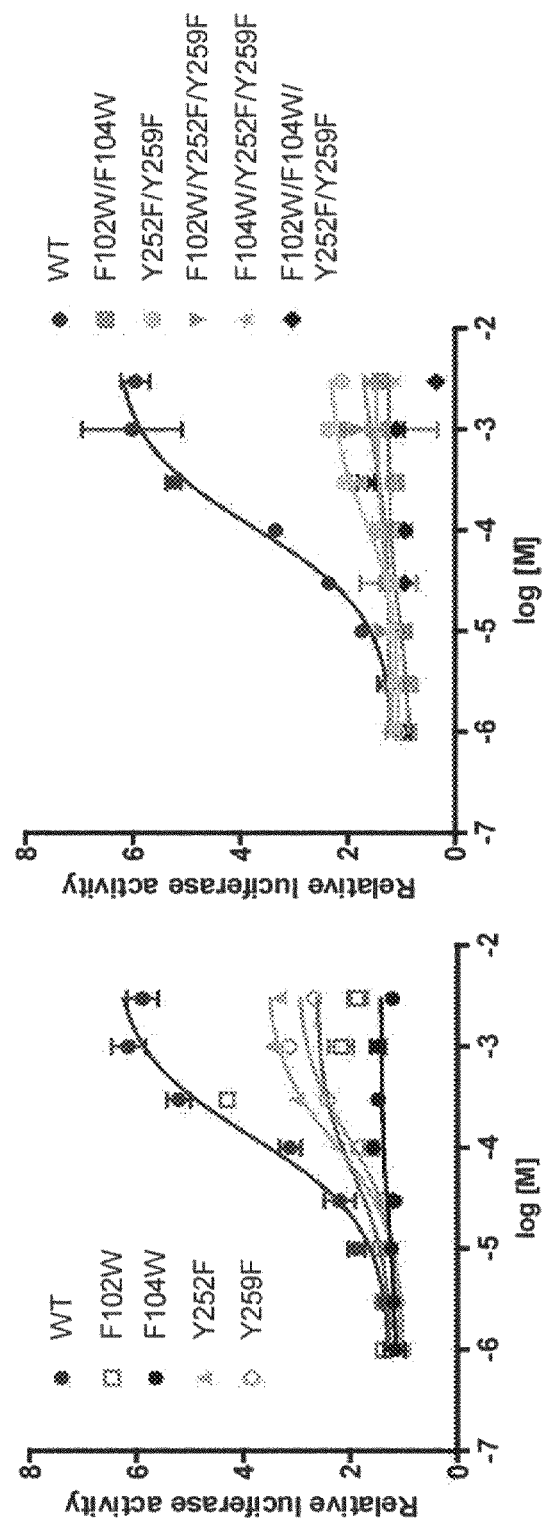
[FIG.18]

[FIG.19]
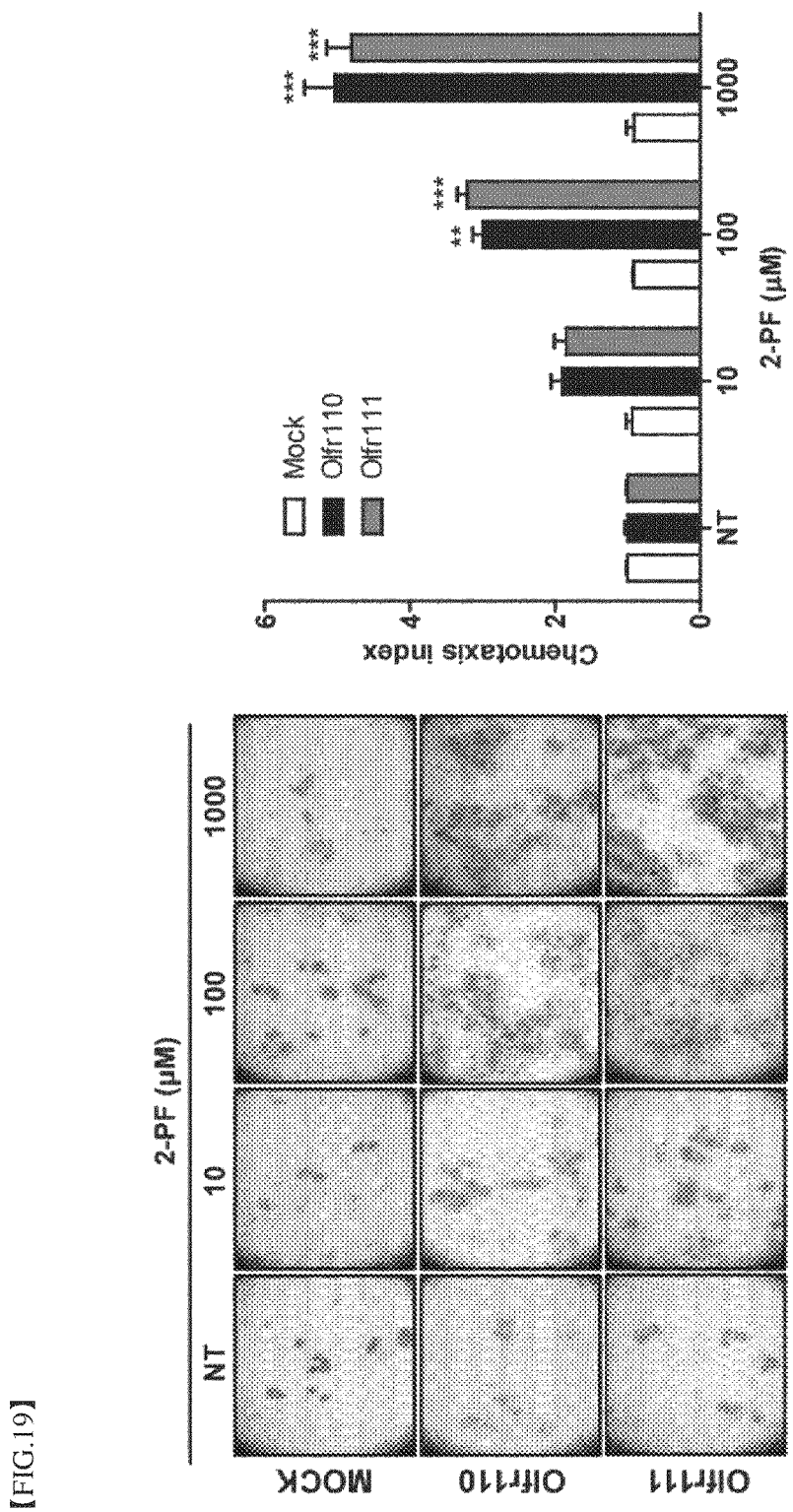

[FIG.20]
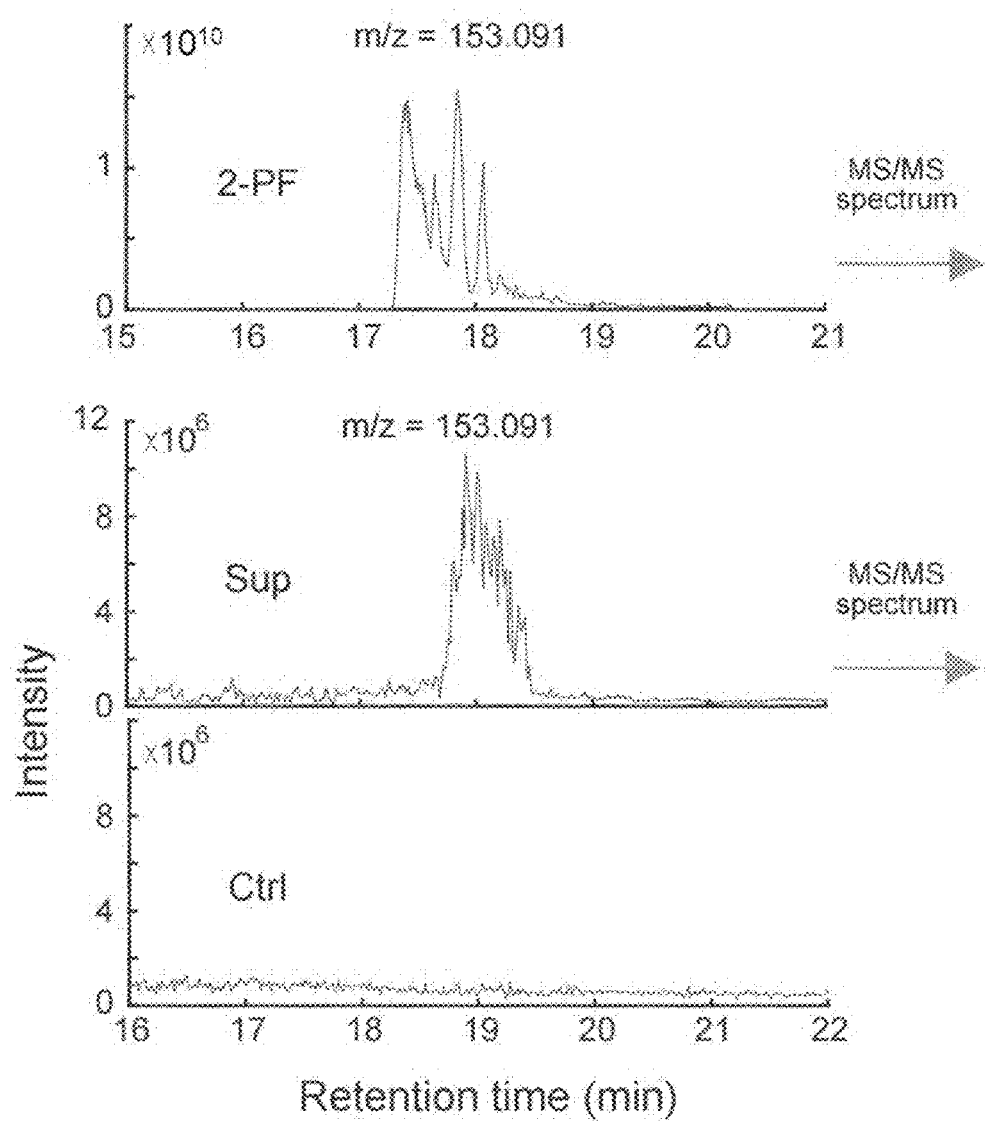

[FIG.21]
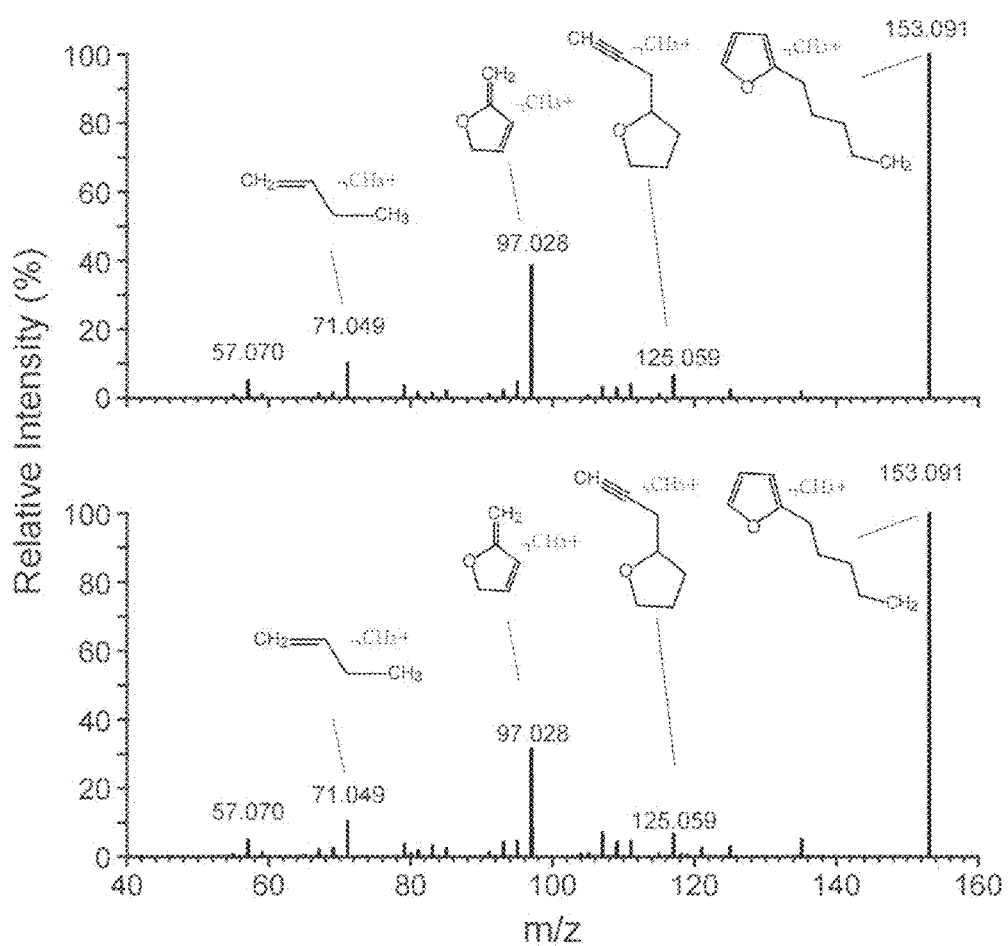

[FIG.22]
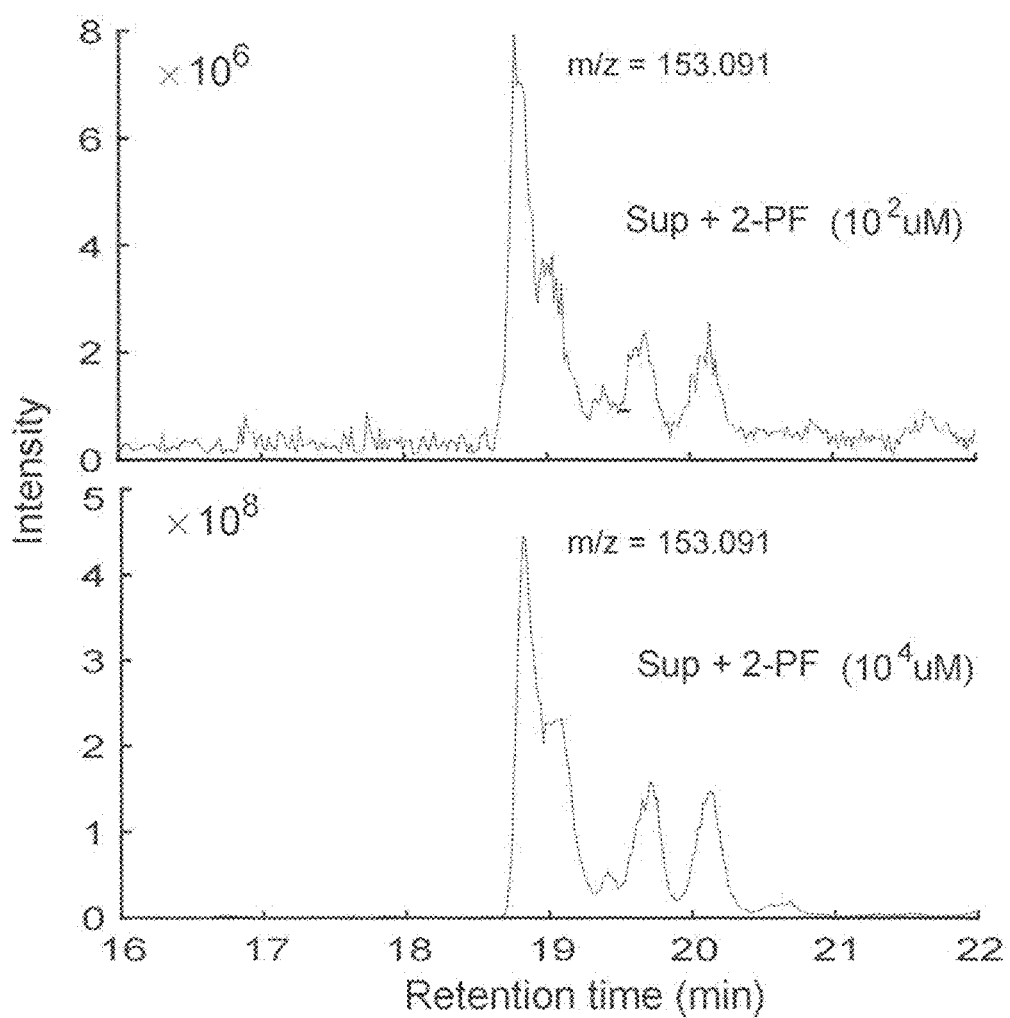

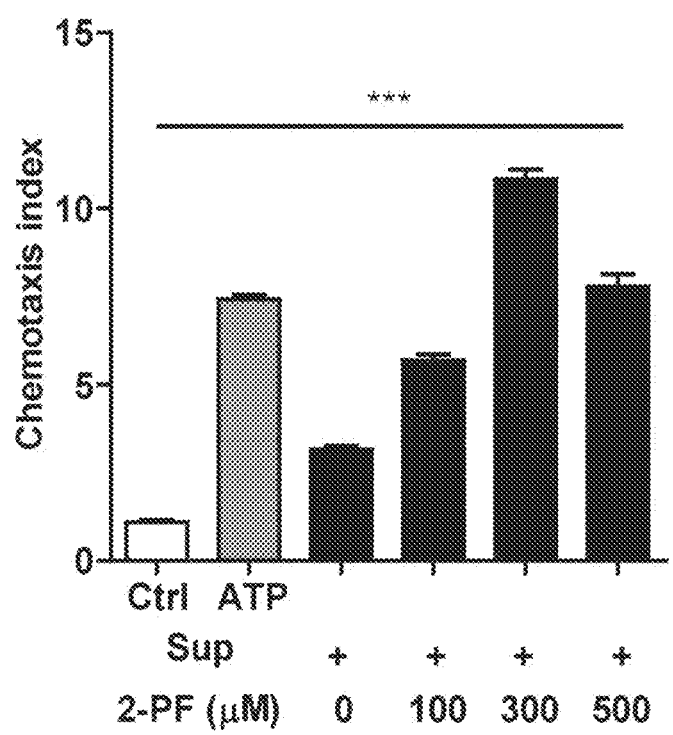
[FIG.23]

[FIG.24]
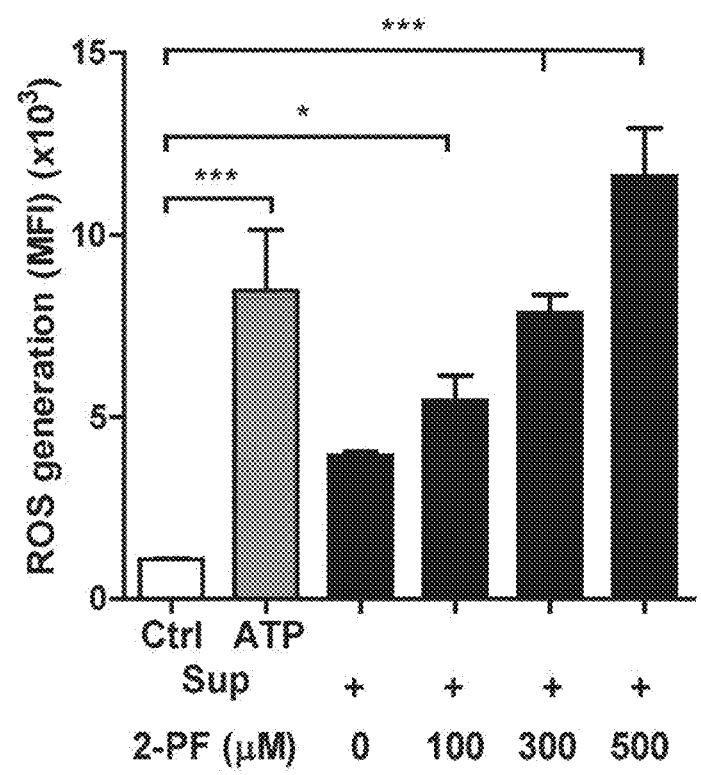

[FIG.25]
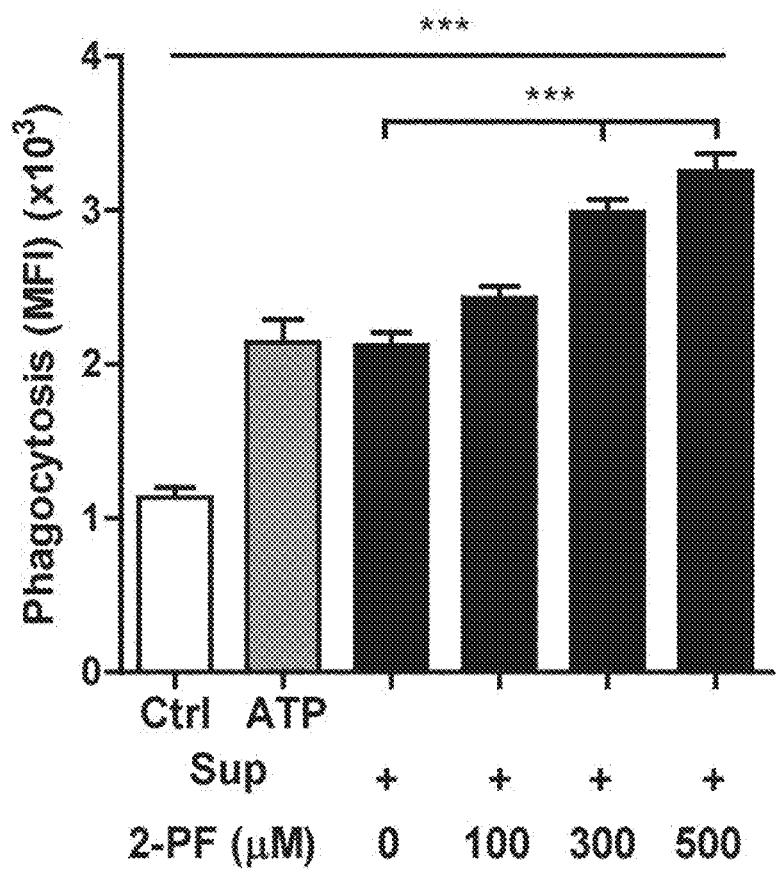

[FIG. 26]
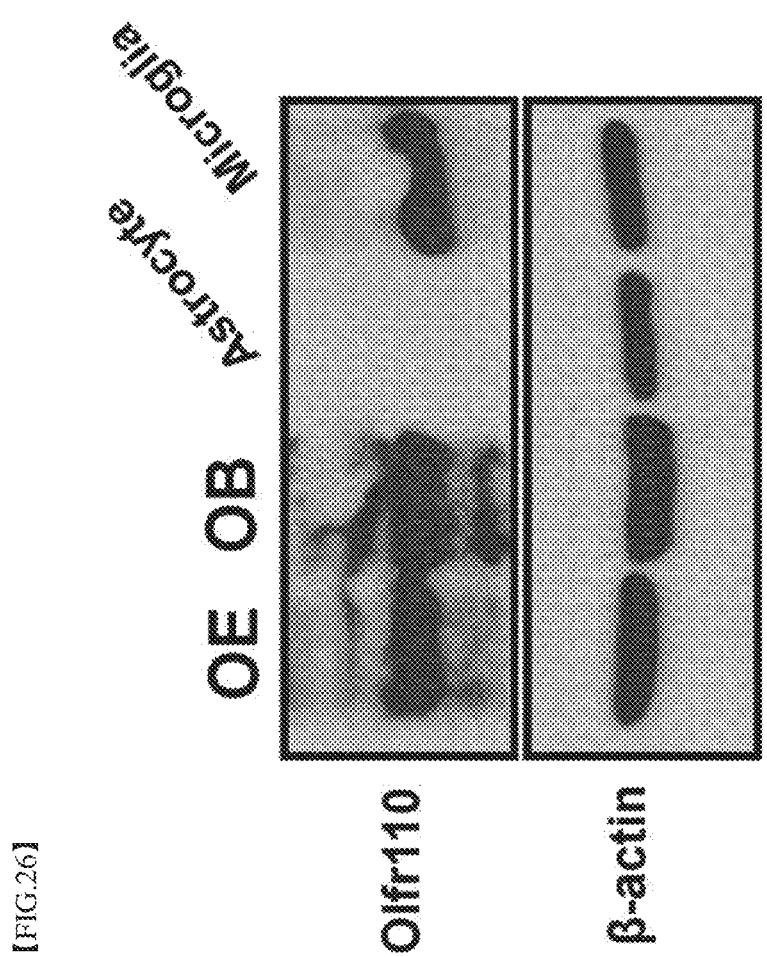

[FIG.27]
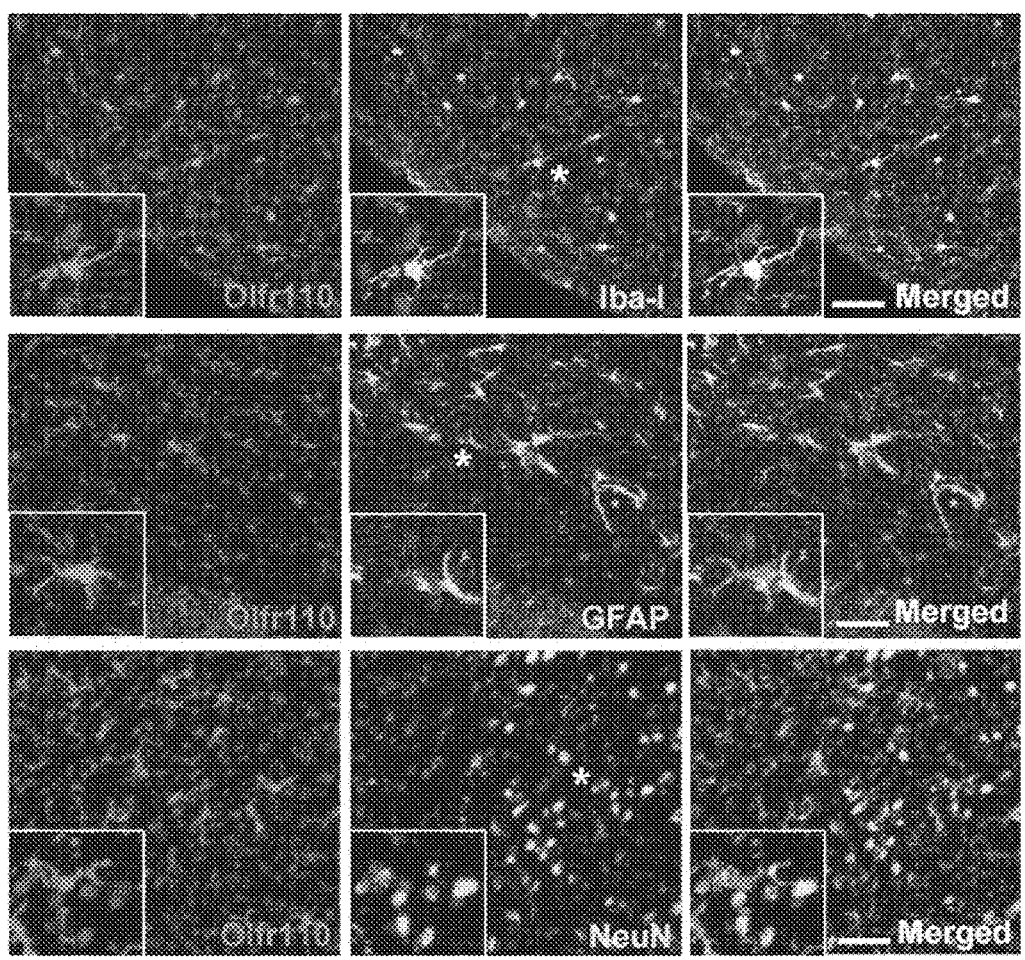

[FIG.28]
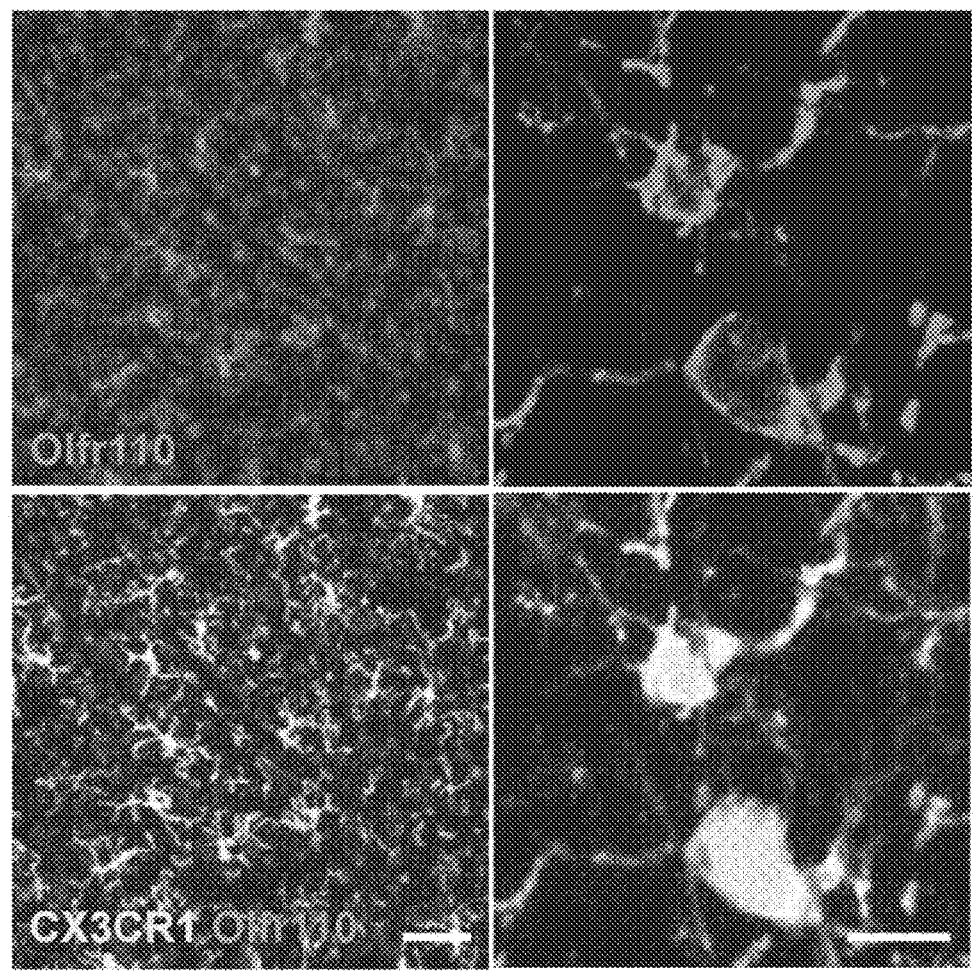

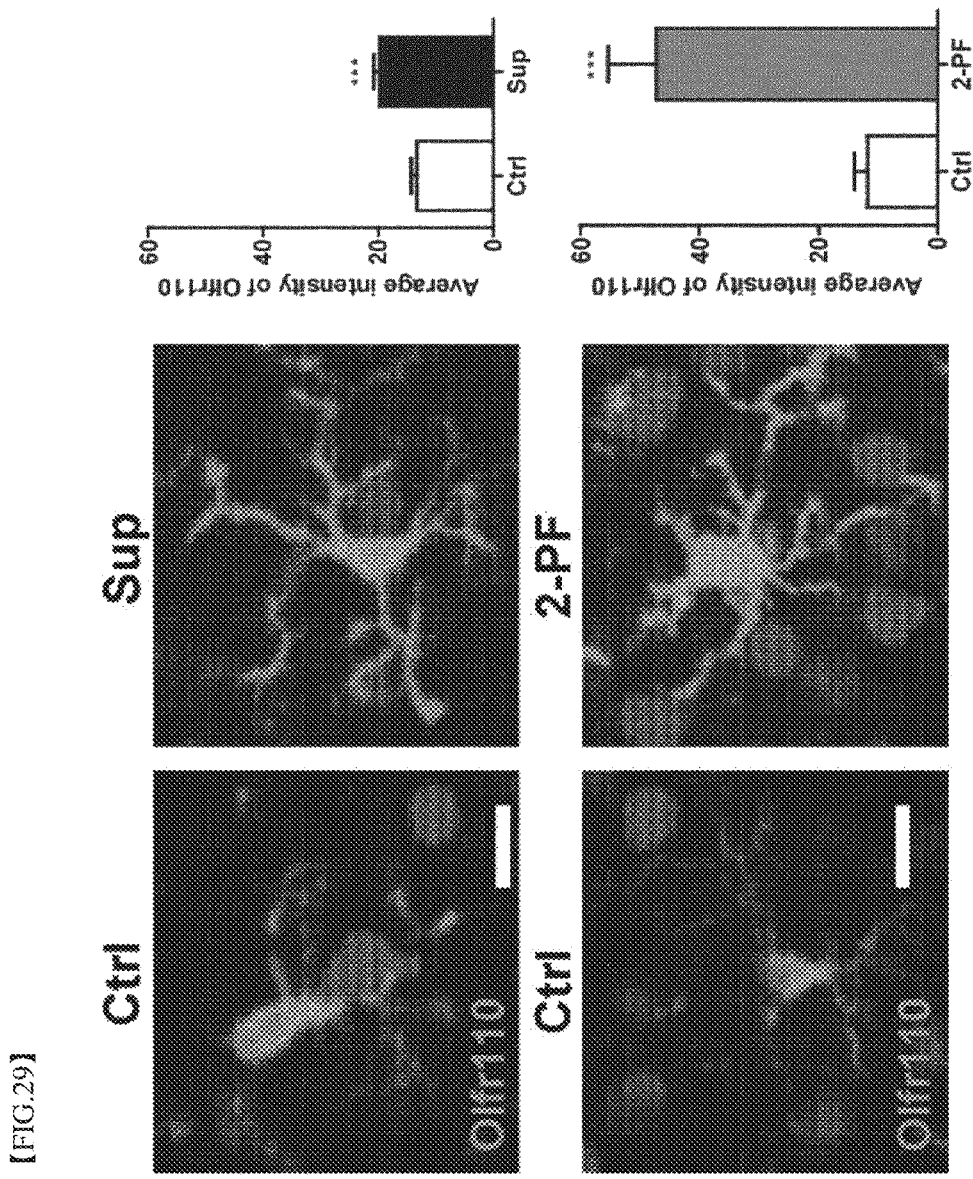
[FIG. 29]

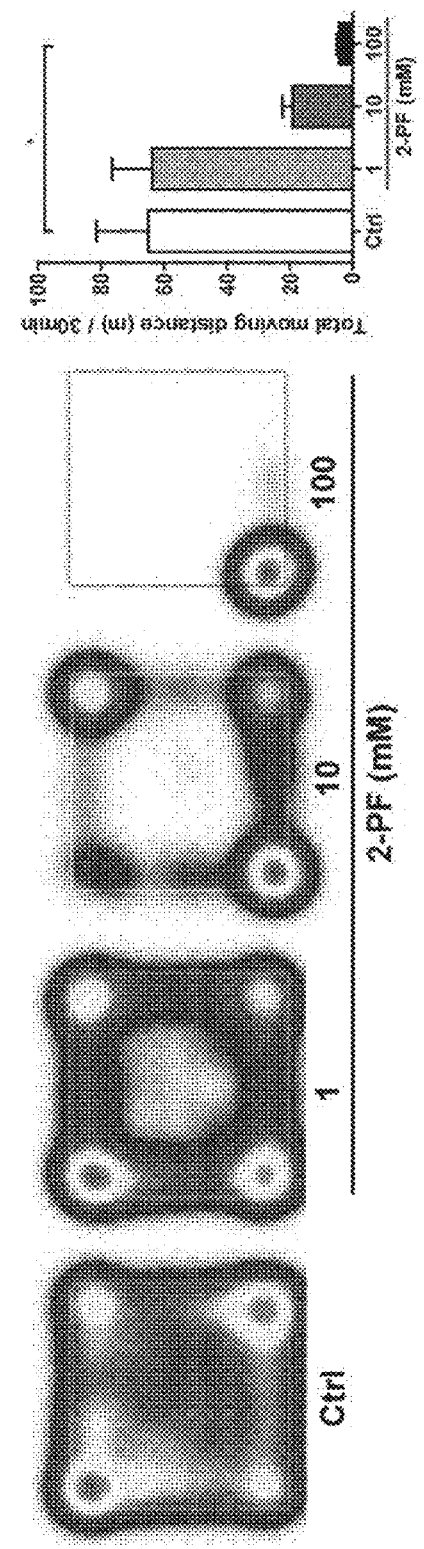
[FIG. 30]

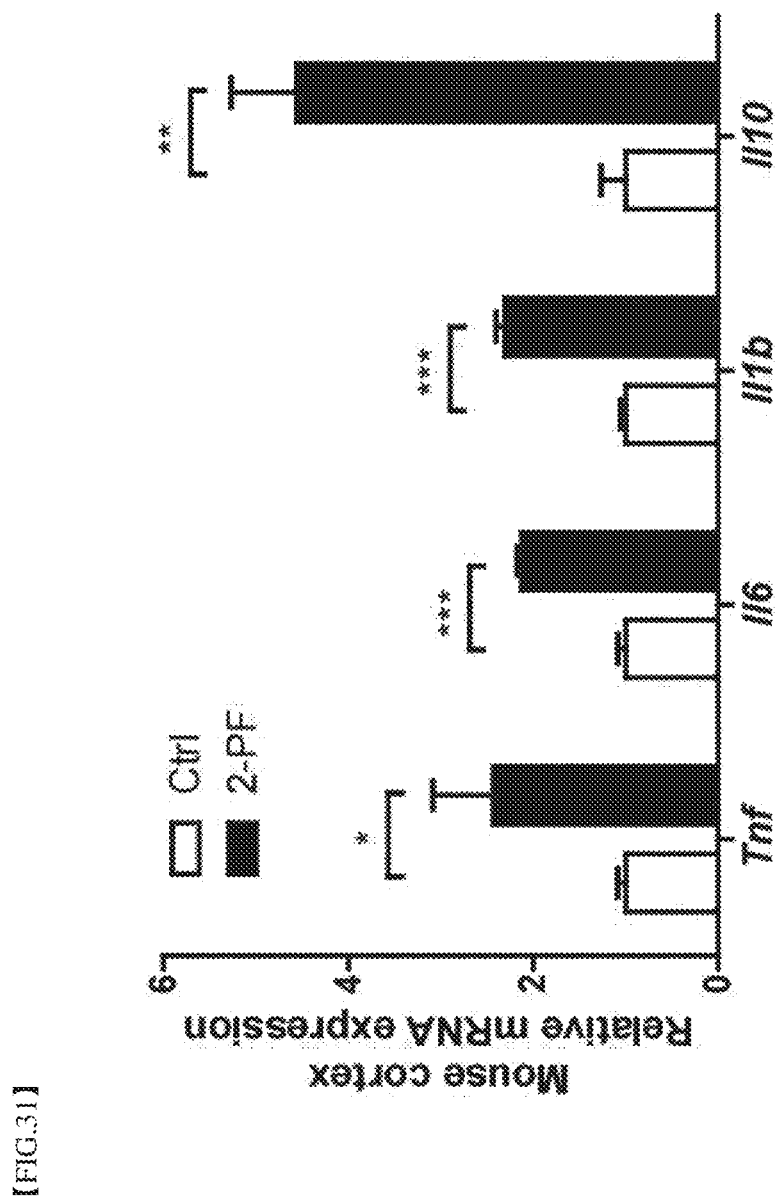
[FIG. 31]

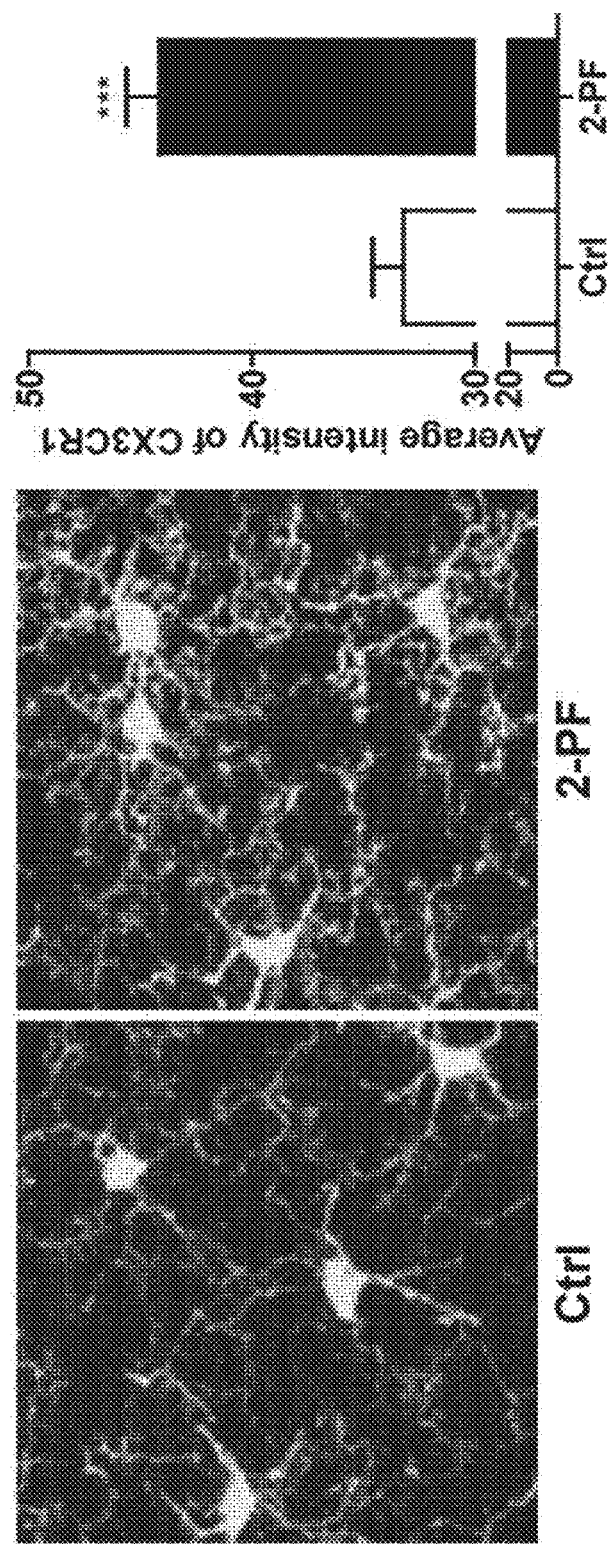
[FIG. 32]

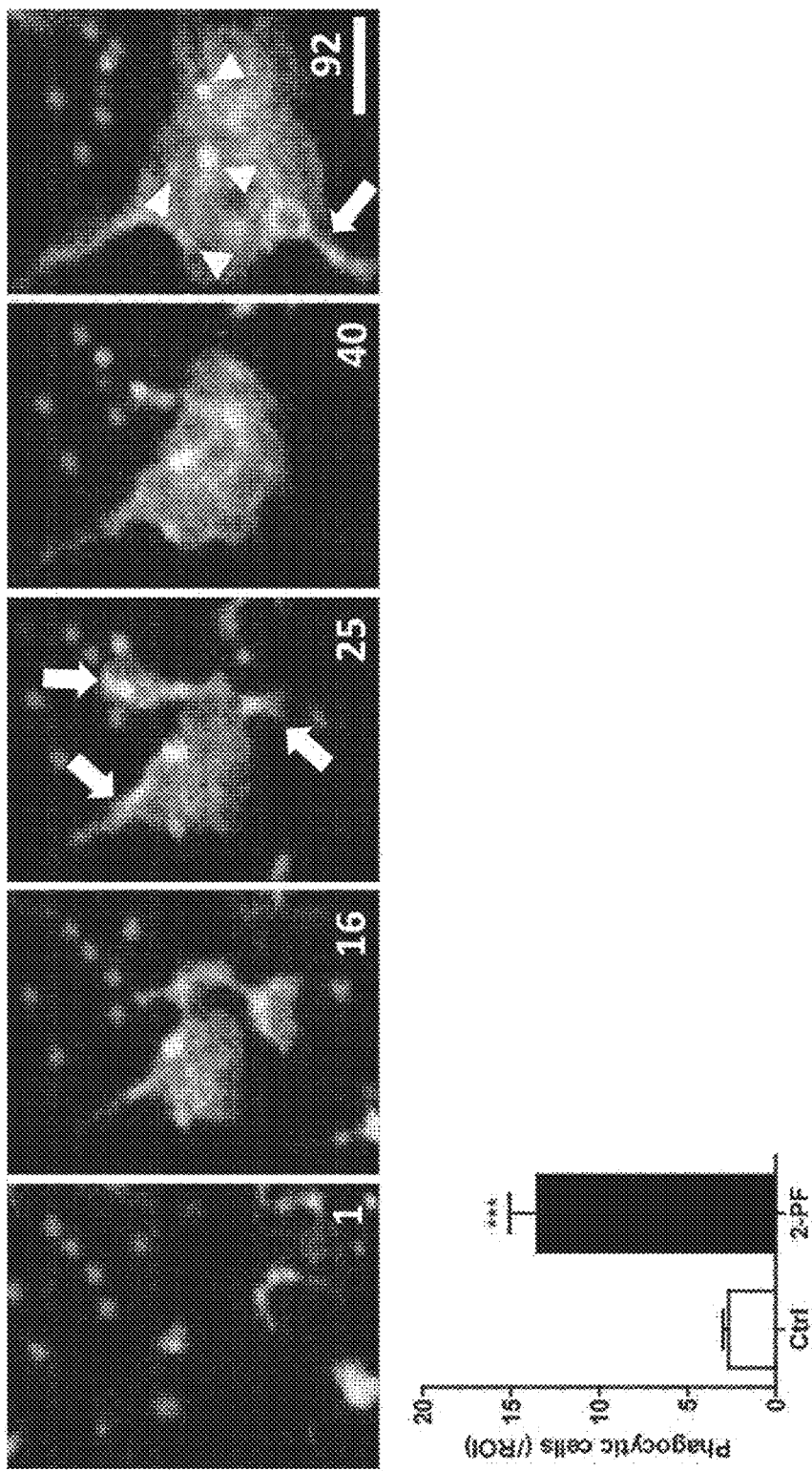
[FIG.33]

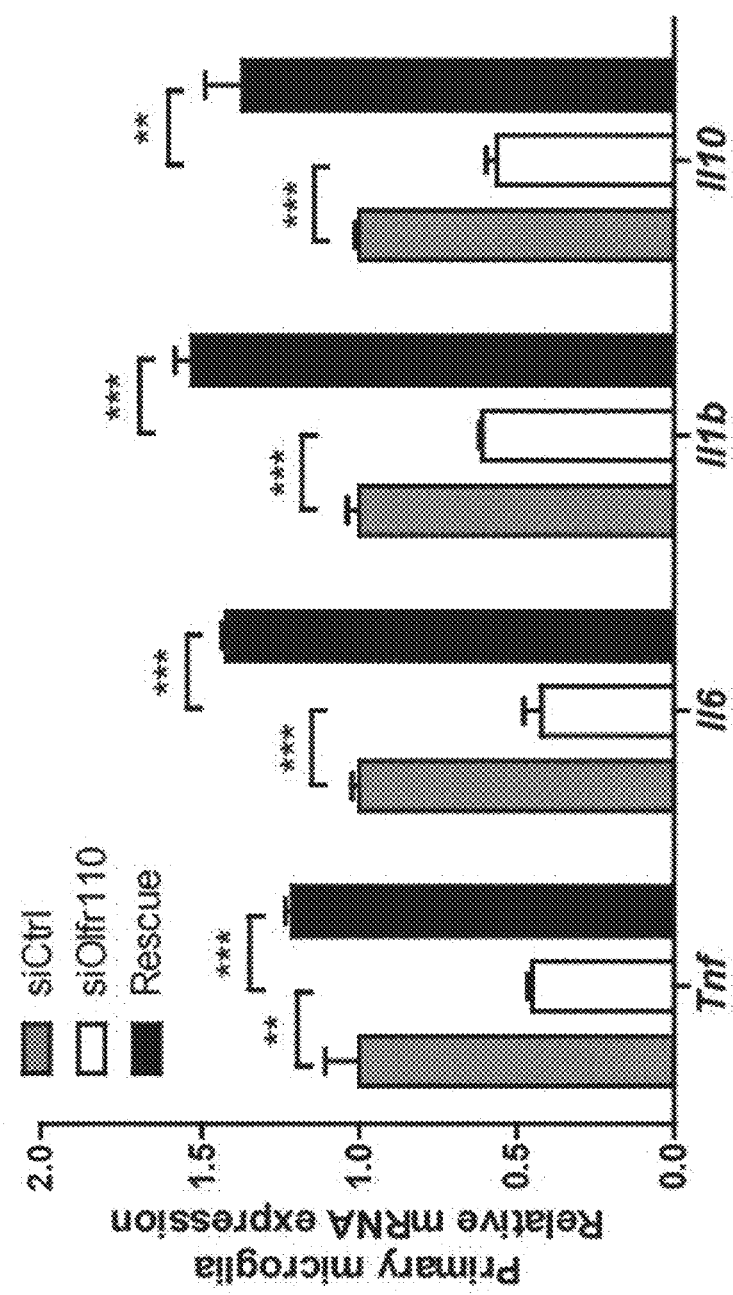
[FIG. 34]

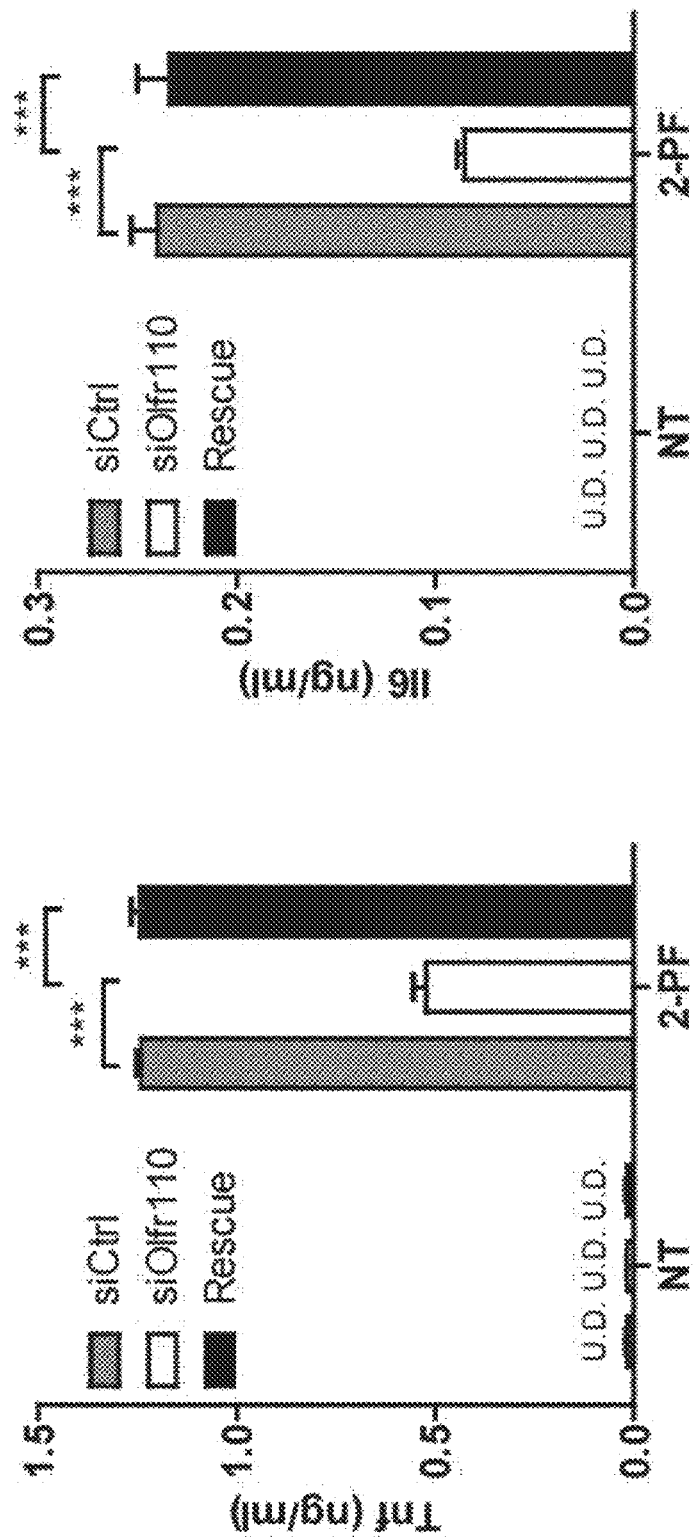
[FIG. 35]

[FIG.36]
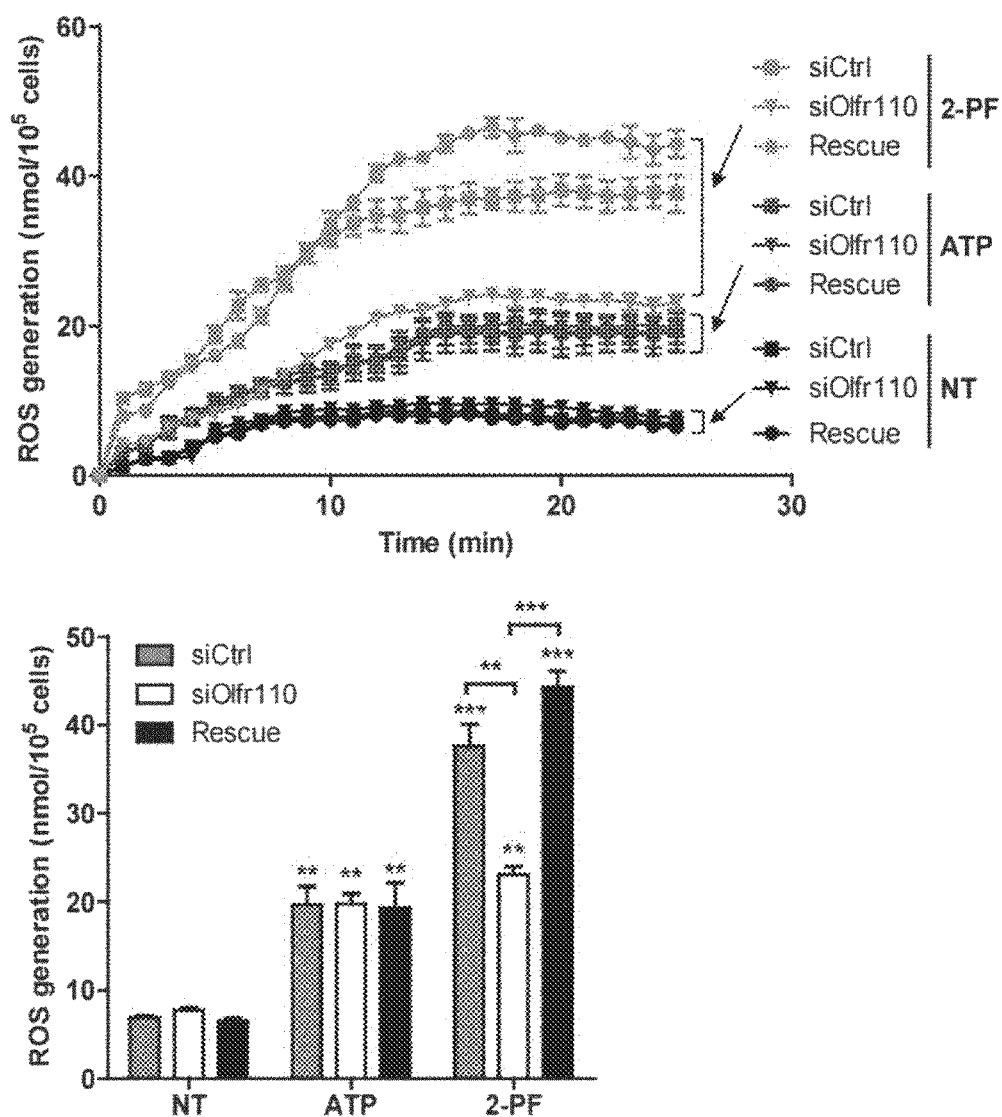

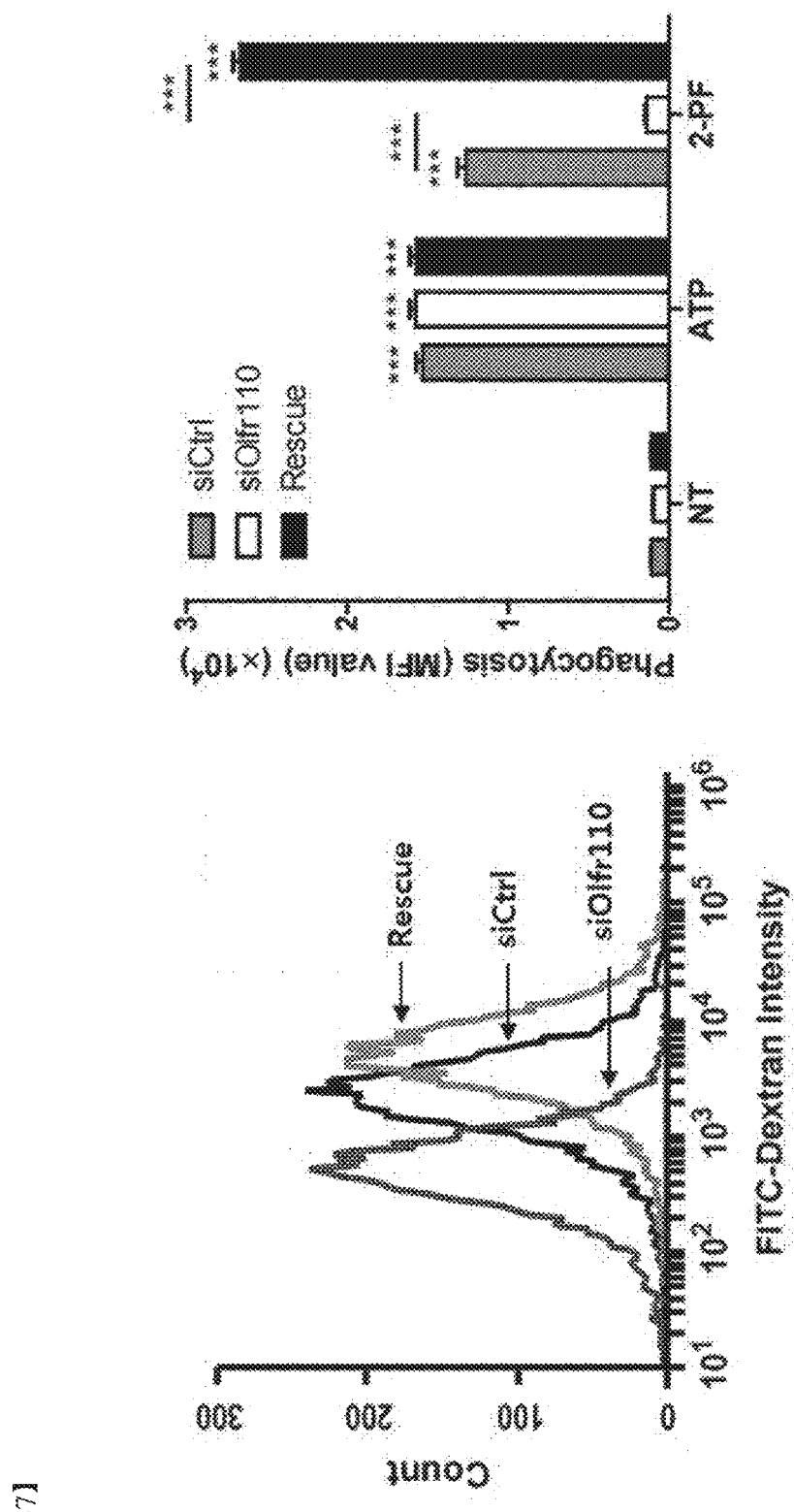
[FIG. 37]

[FIG.38]
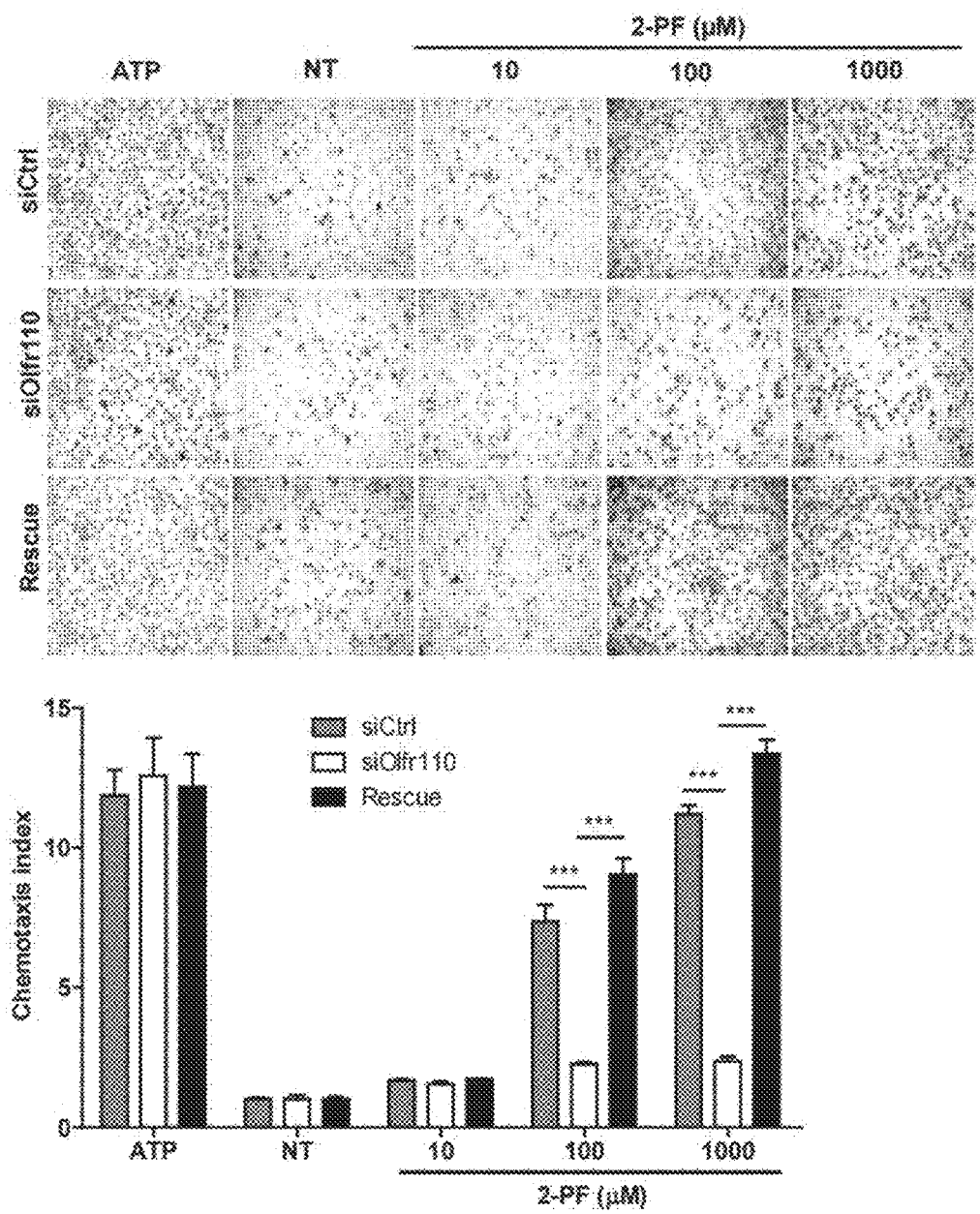

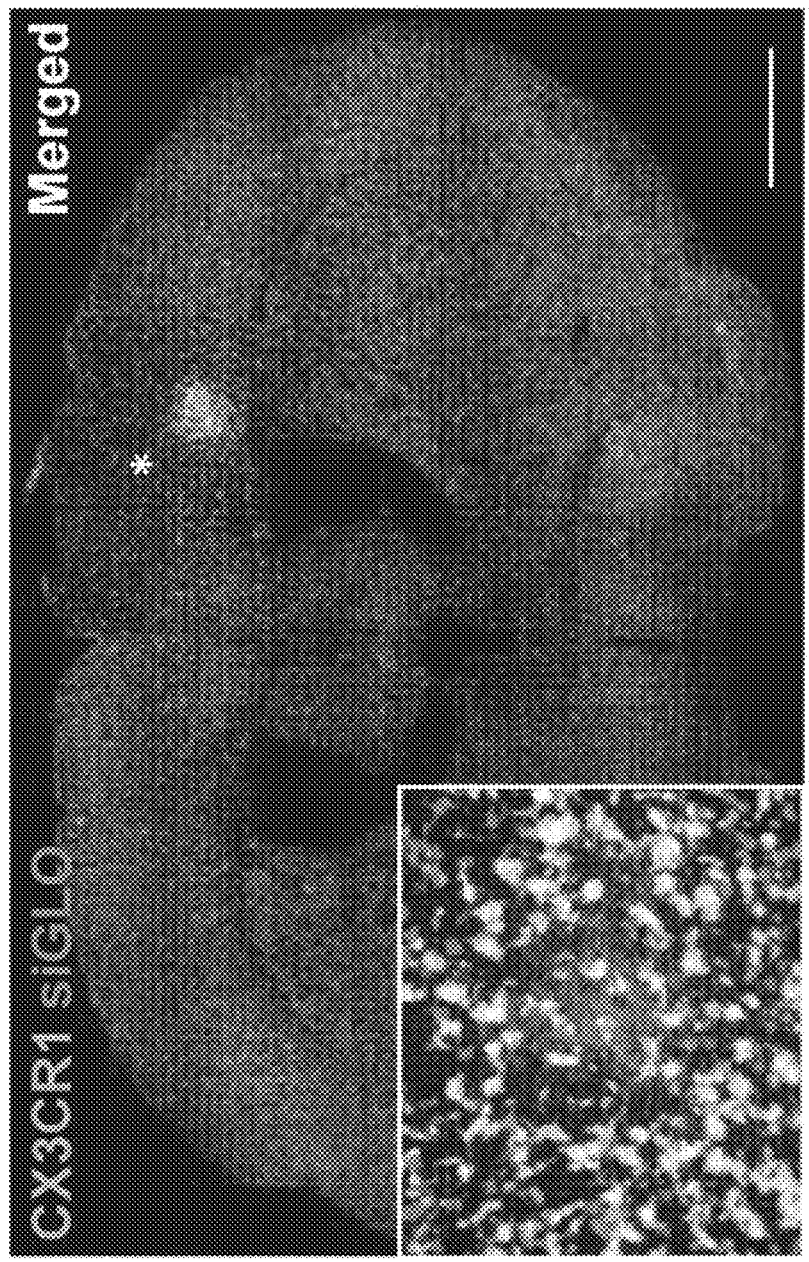
[FIG. 39]

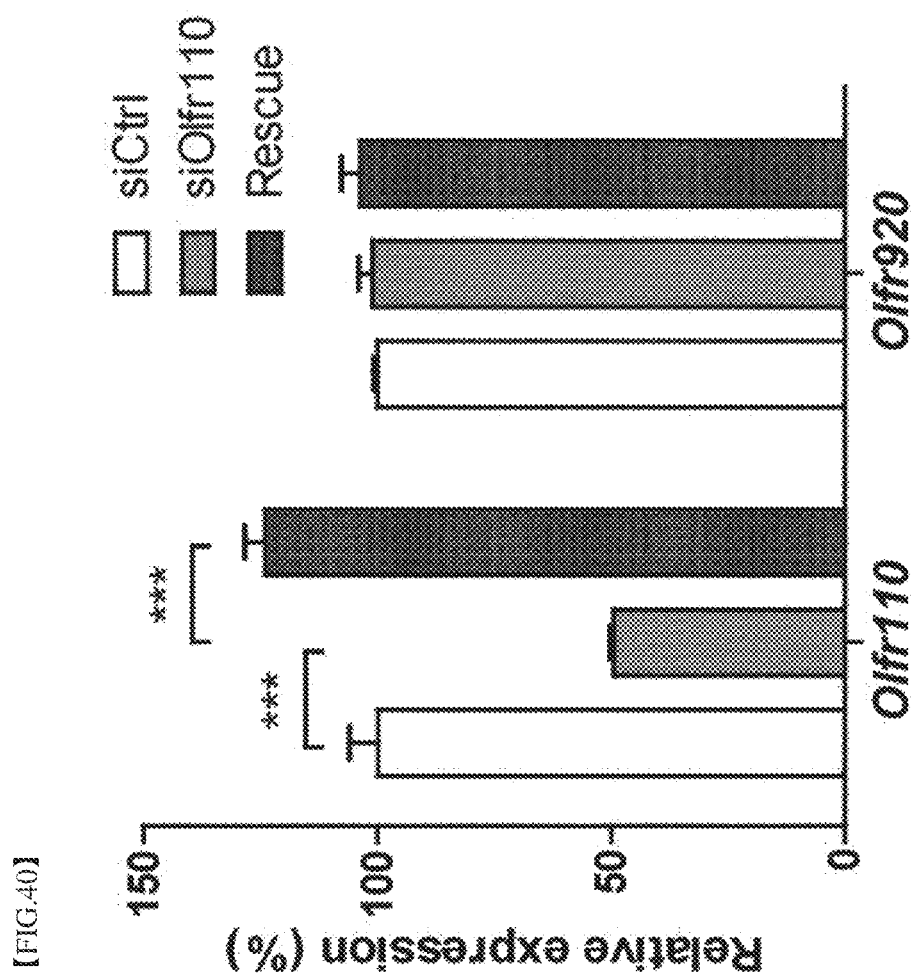
[FIG. 40]

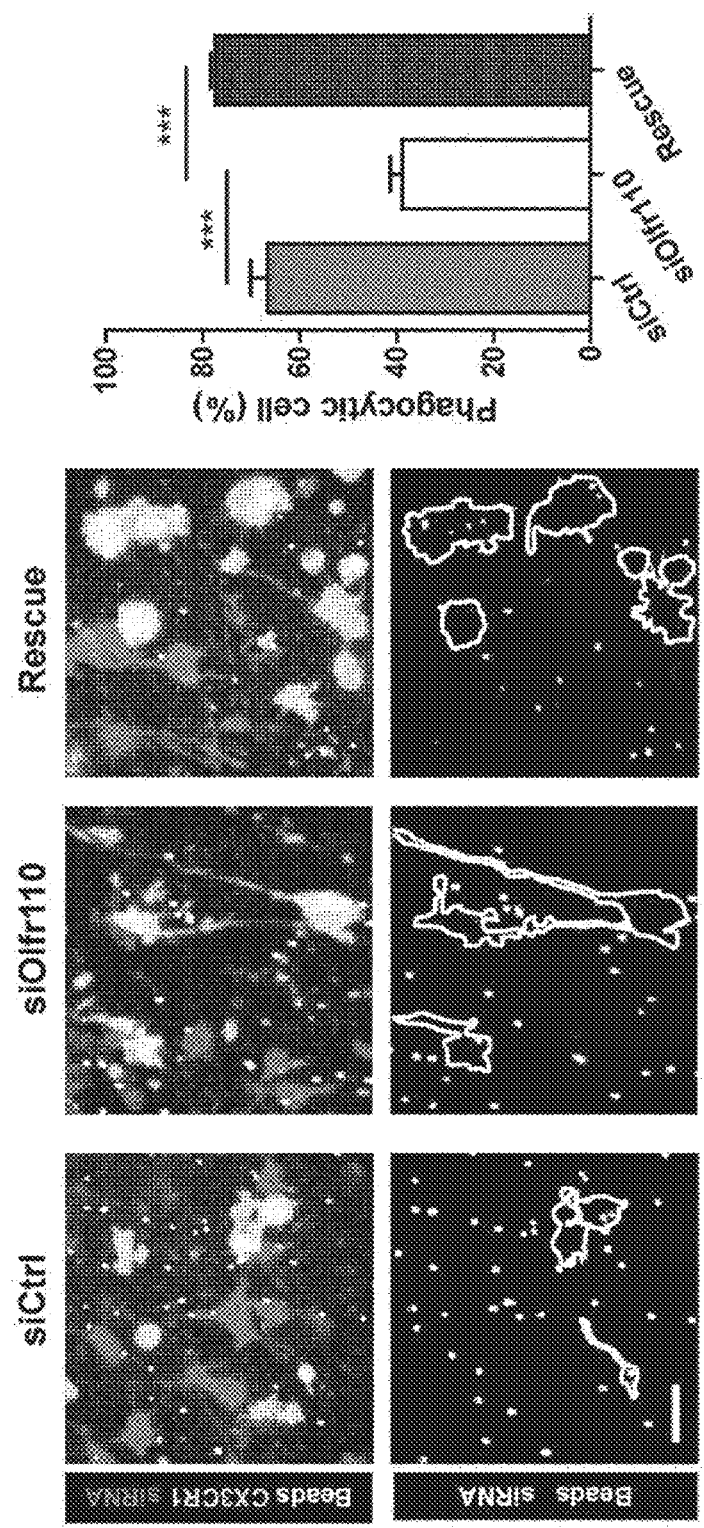
[FIG.41]

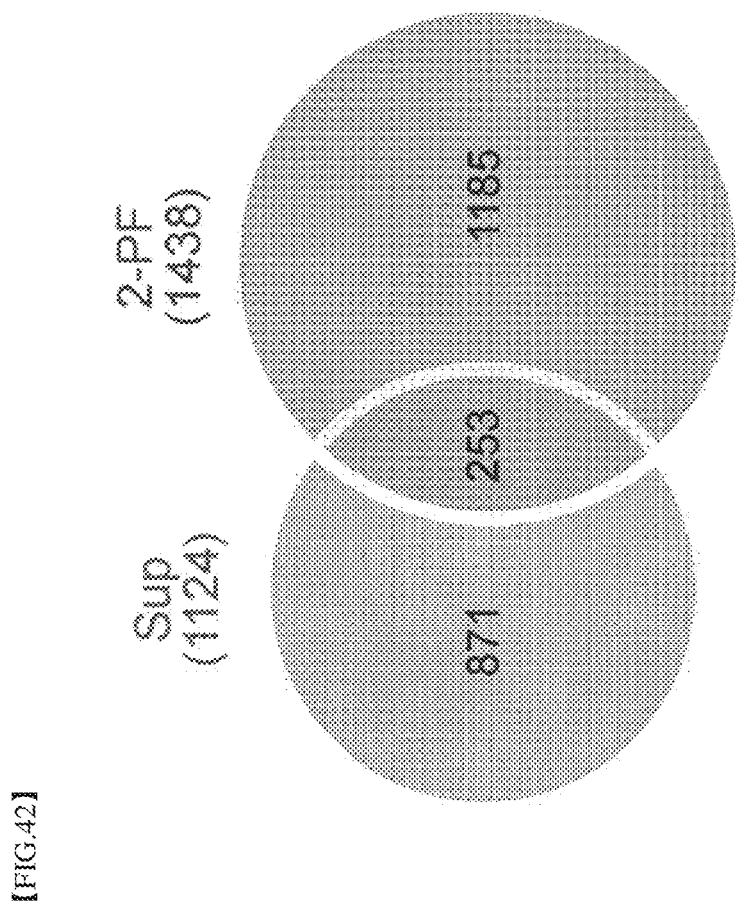
[FIG. 42]

[FIG.43]
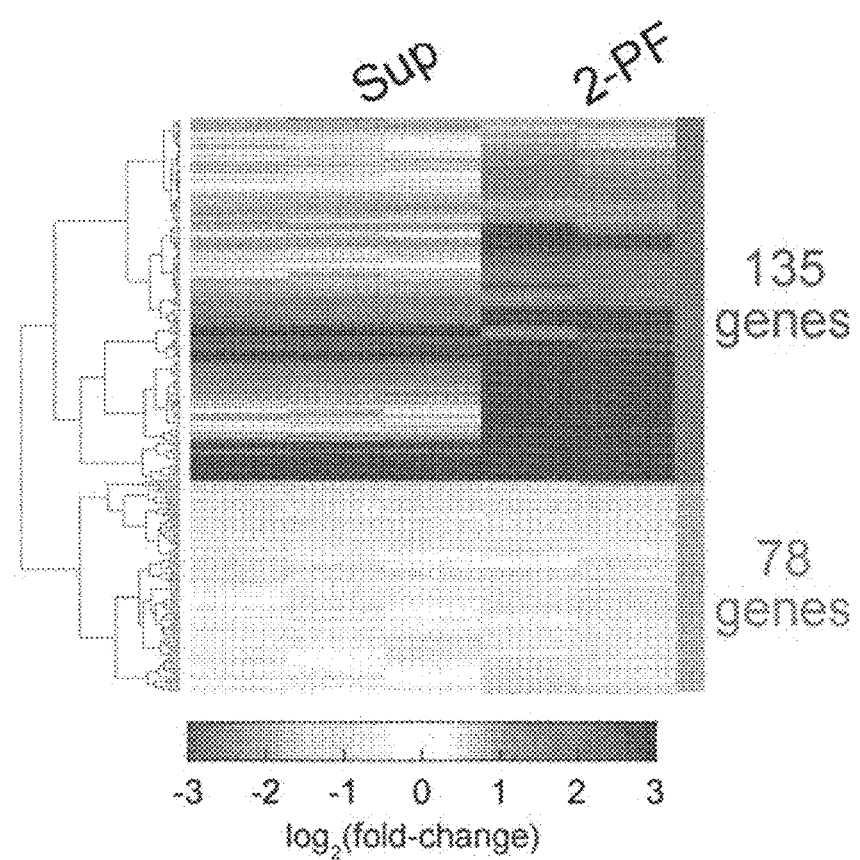

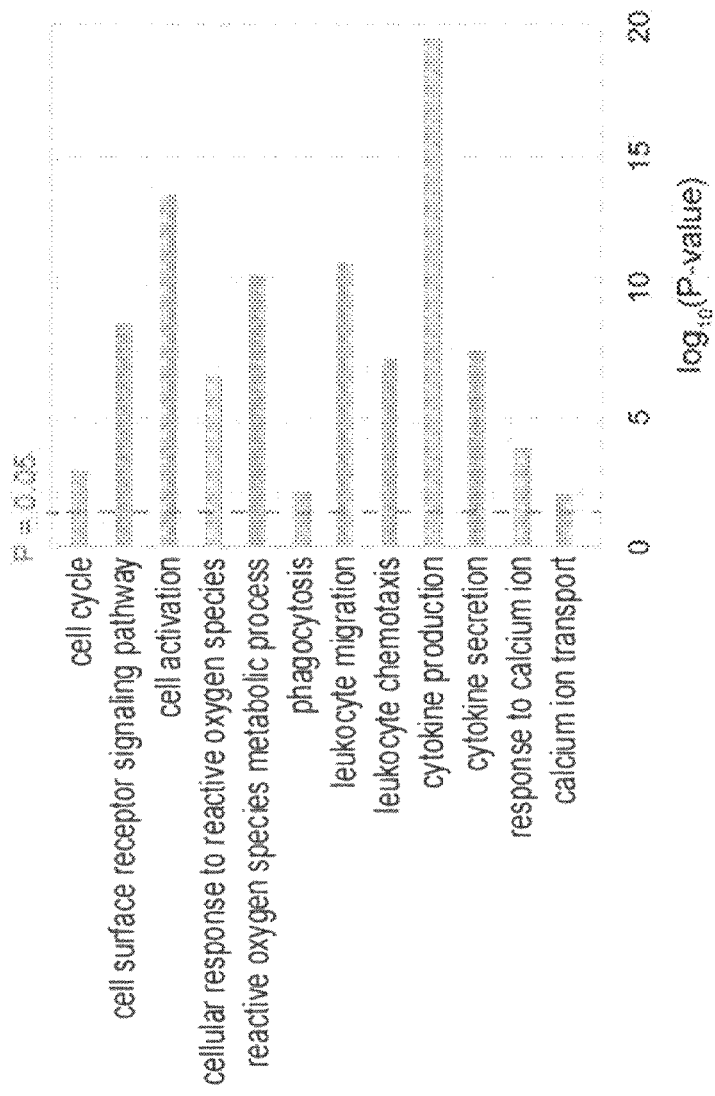
[FIG. 44]

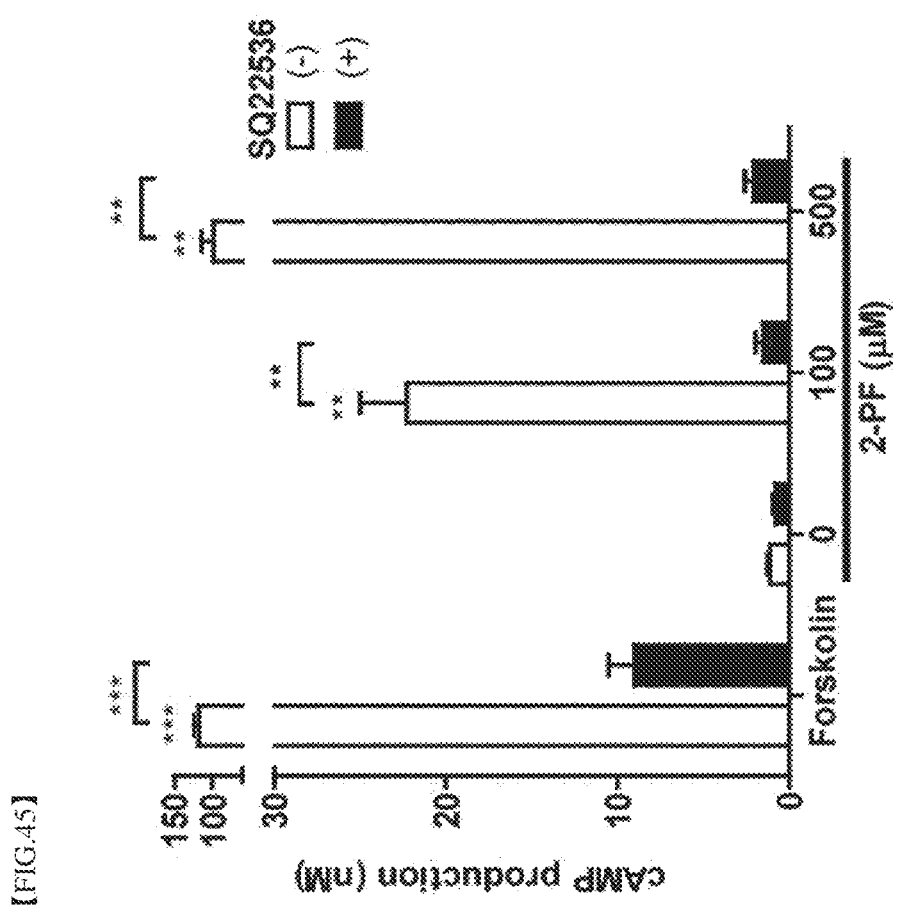
[FIG.45]

[FIG.46]
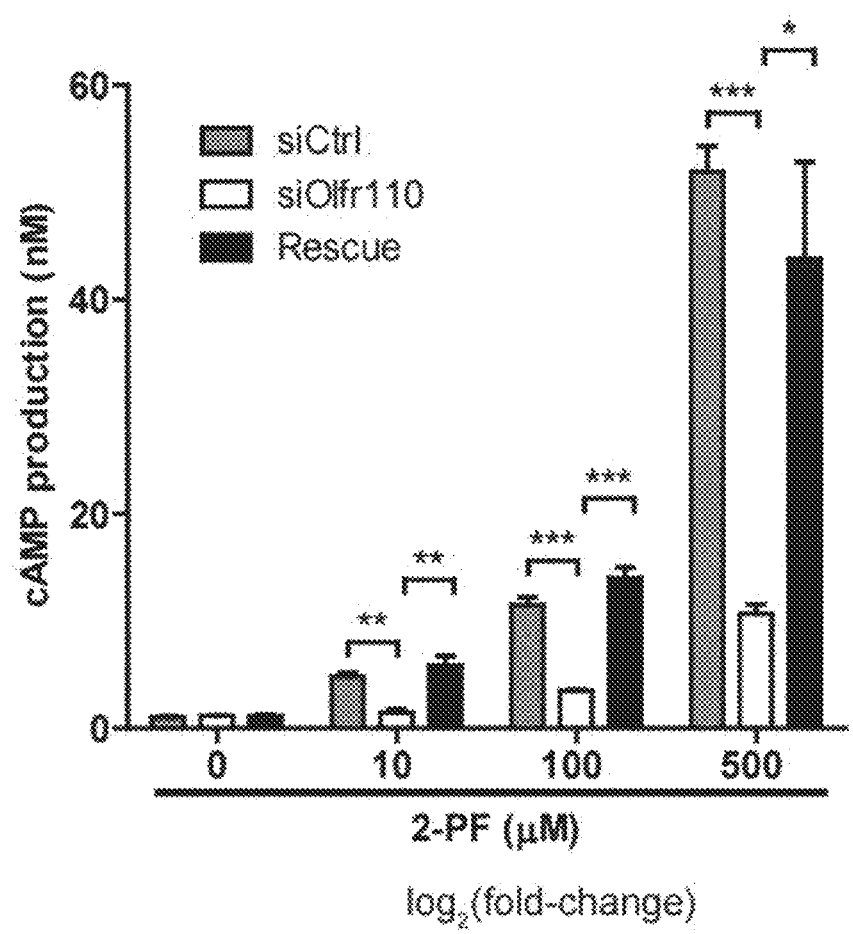

[FIG.47]
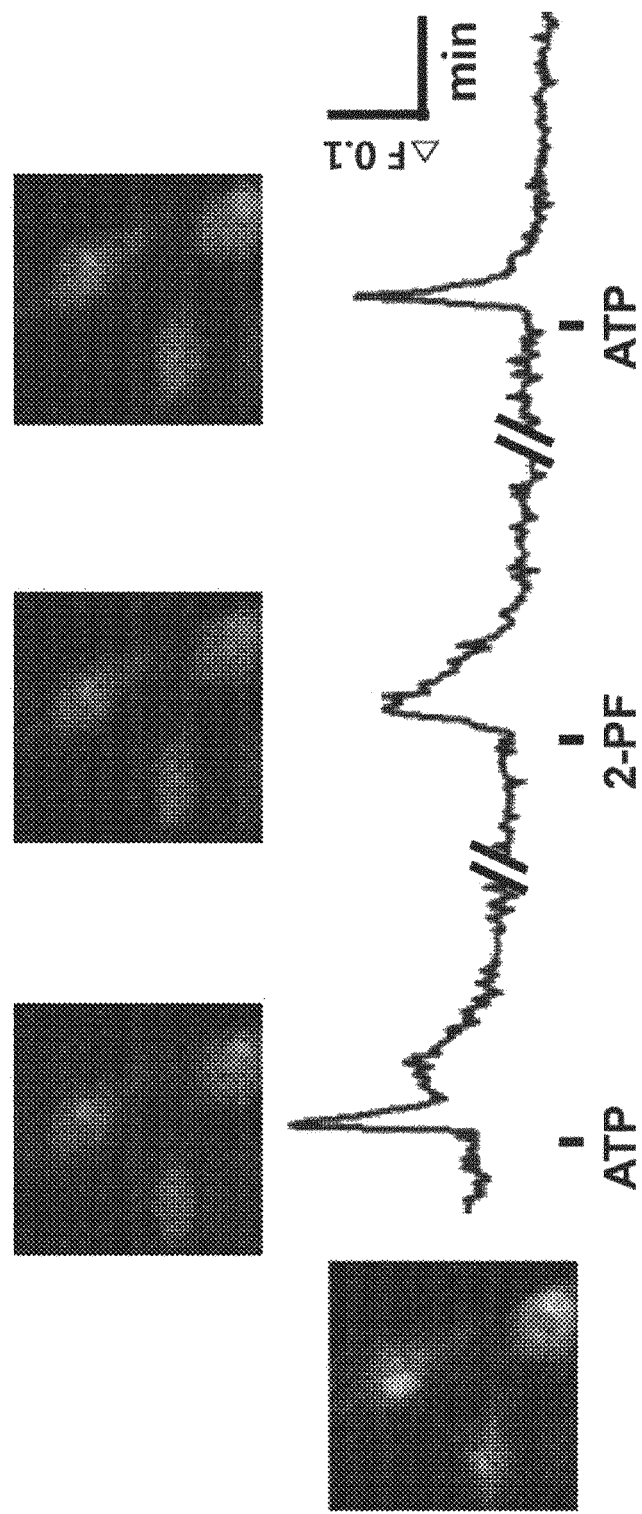

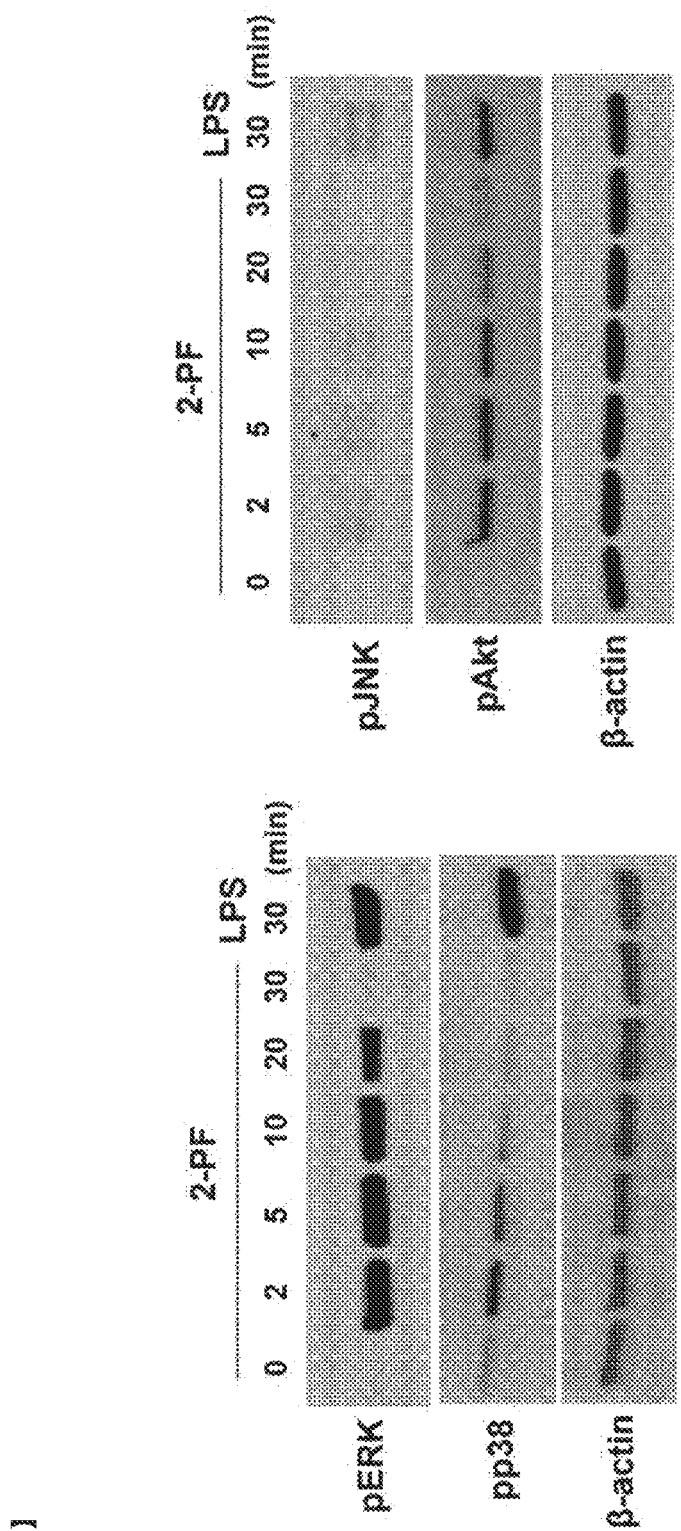
[FIG.48]

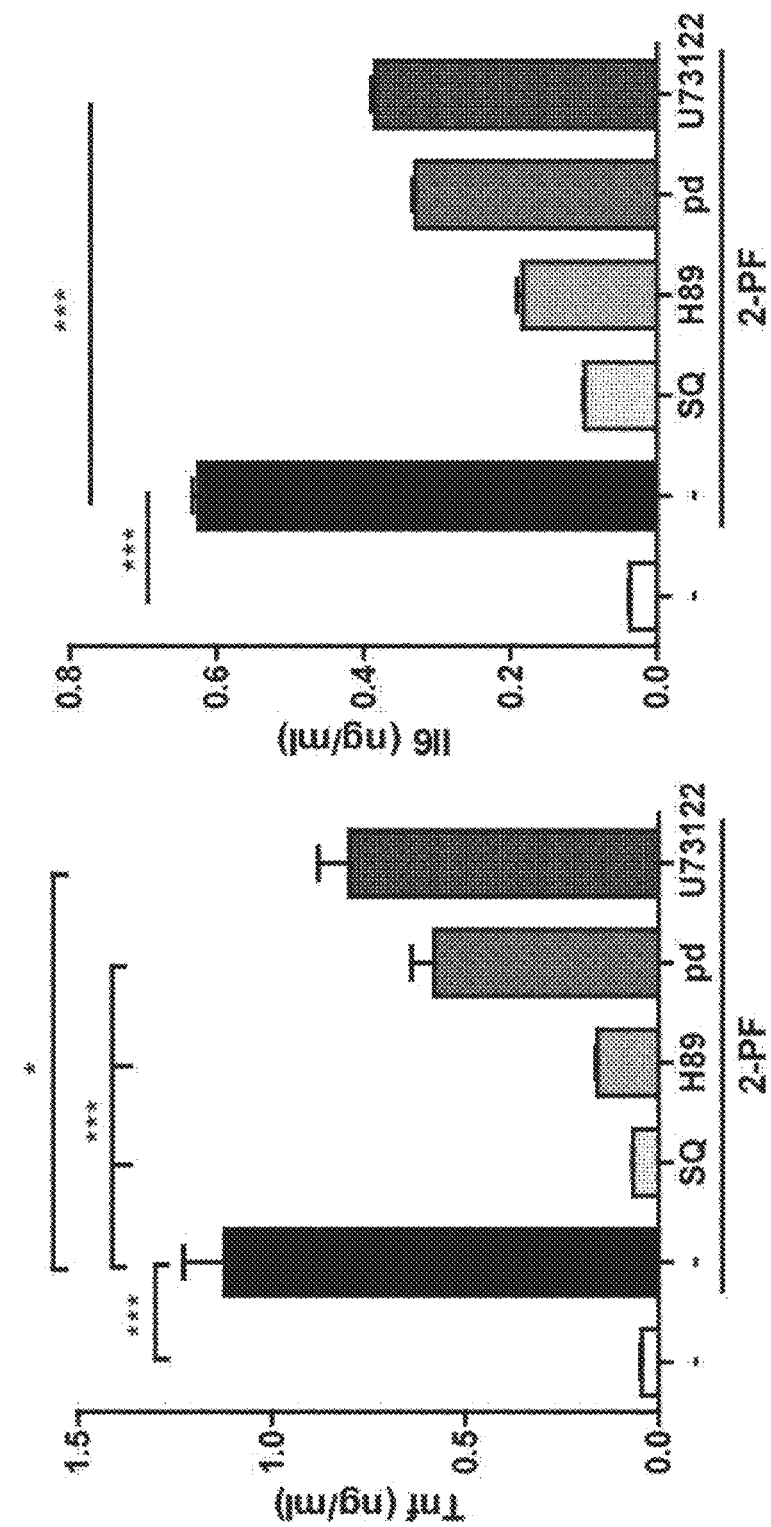
[FIG.49]

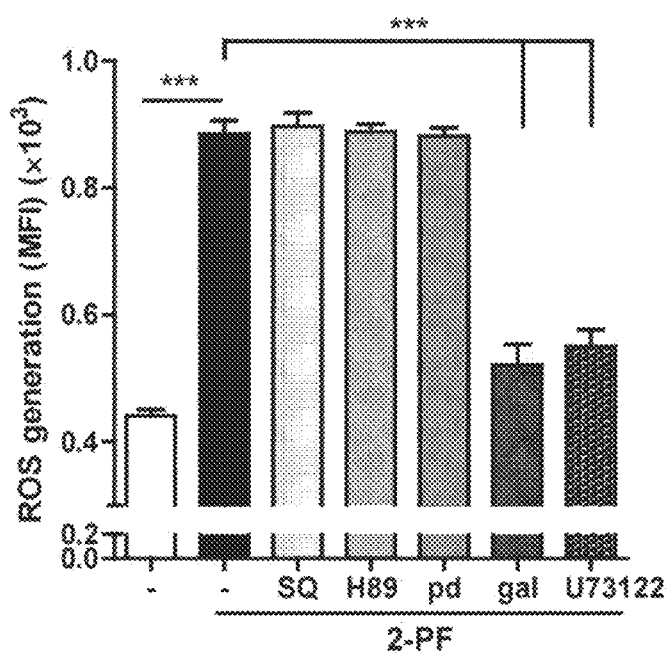
[FIG.50]

[FIG.51]
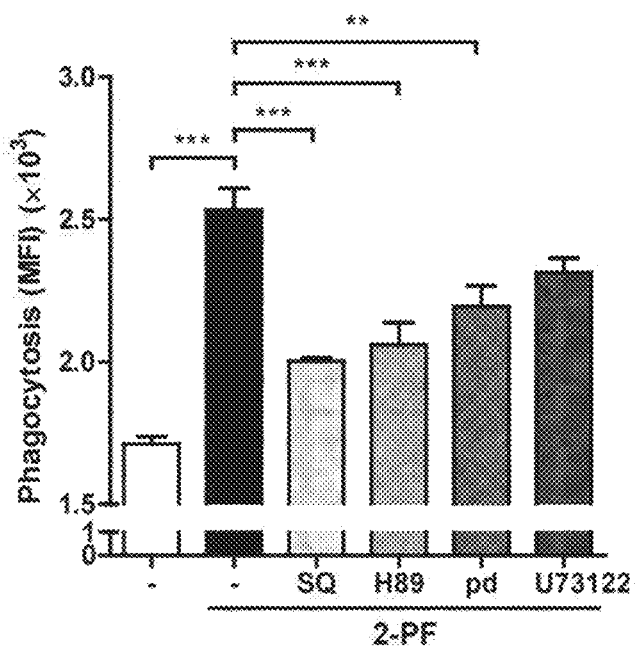

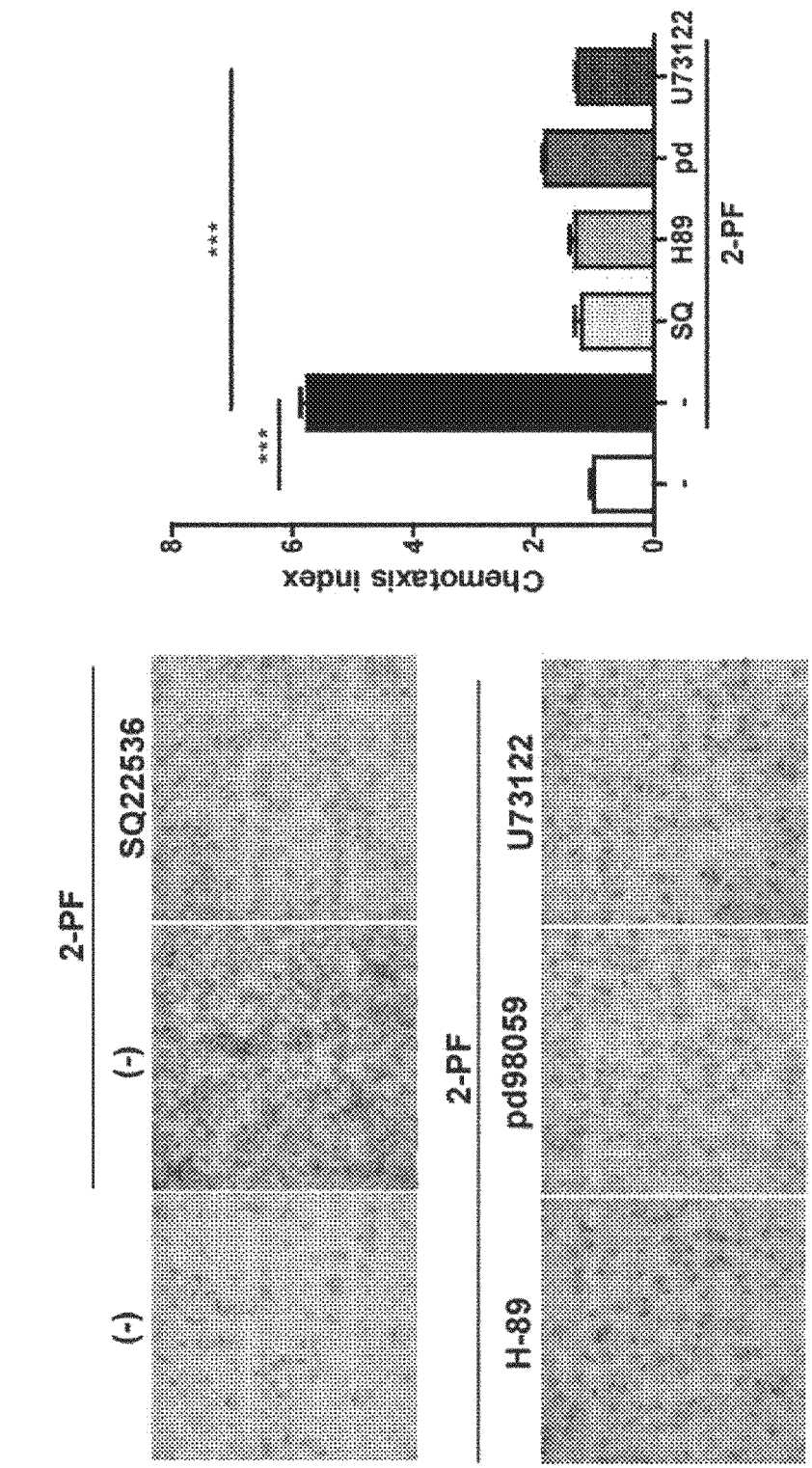
[FIG.52]

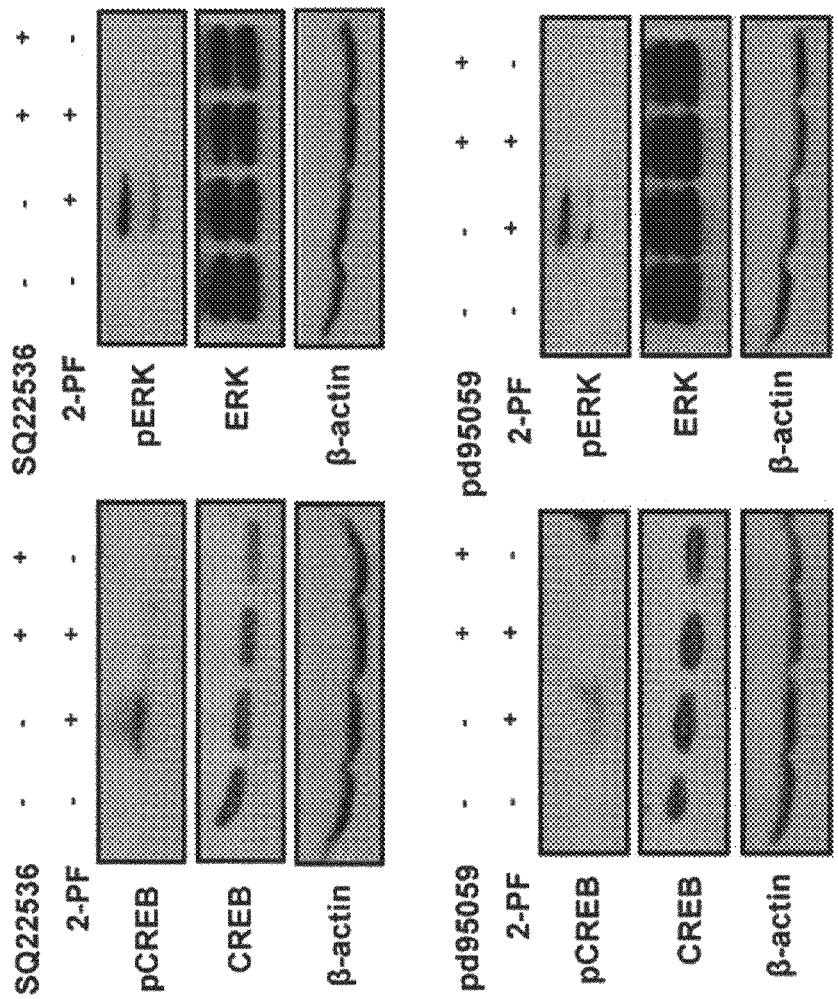
[FIG.53]

[FIG.54]
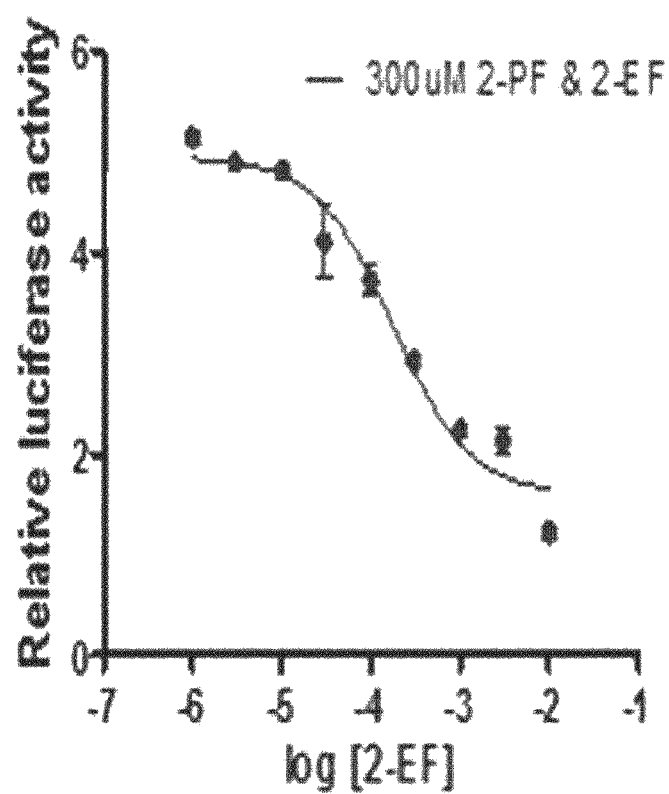

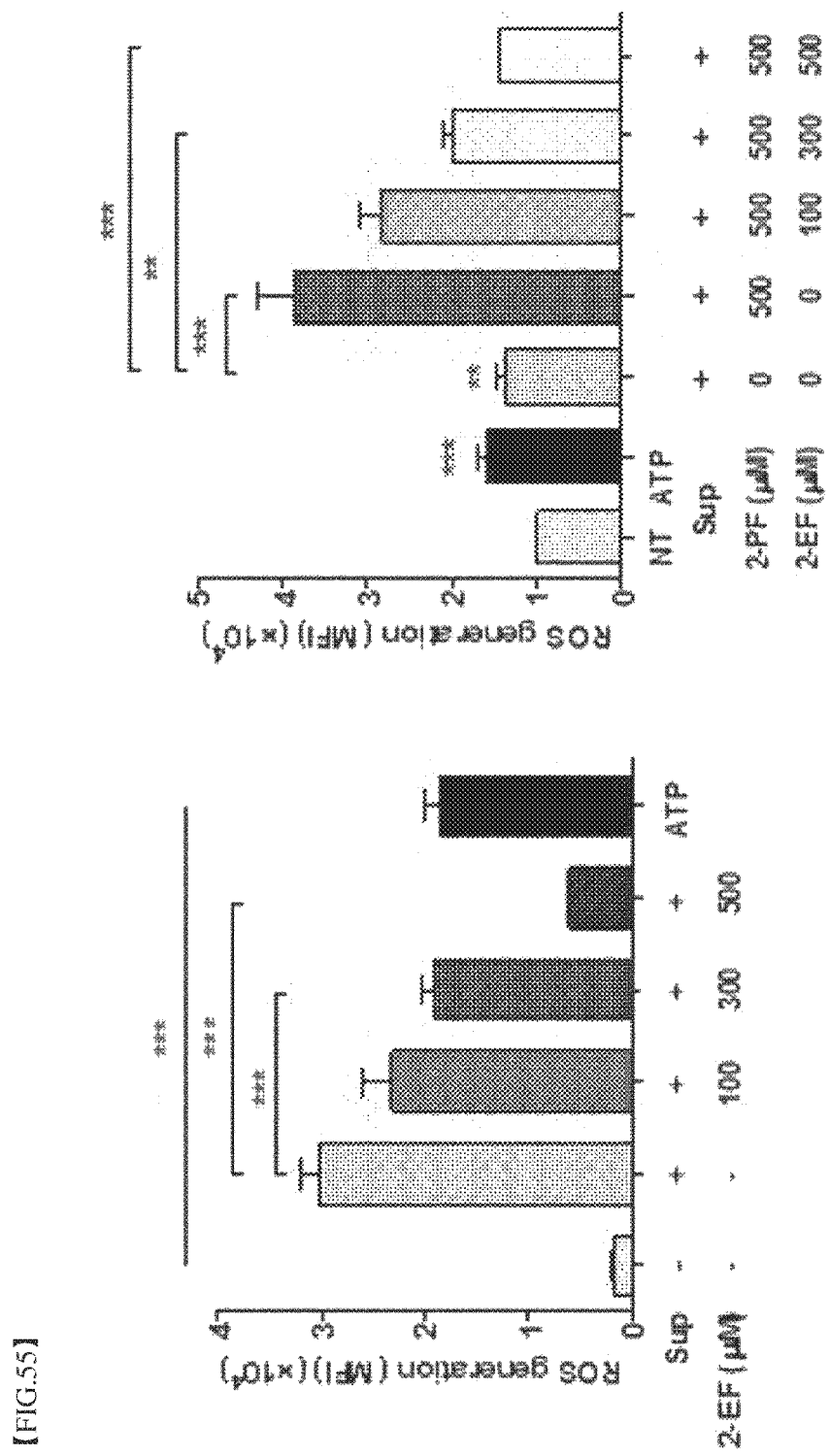
[FIG.55]

COMPOSITION FOR TREATING DEGENERATIVE BRAIN DISEASES, CONTAINING 2-PENTYLFURAN AS ACTIVE INGREDIENT

CROSS-REFERENCE TO RELATED APPLICATIONS

This application is a national phase under 35 U.S.C. § 371 of PCT International Application No. PCT/KR2020/008347 which has an International filing date of Jun. 26, 2020, which claims priority to Korean Application No. 10-2019-0077257, filed Jun. 27, 2019, the entire contents of each of which are hereby incorporated by reference.

TECHNICAL FIELD

The present invention relates to a composition for preventing a degenerative brain disease.

BACKGROUND ART

A degenerative brain disease is characterized in that general impairment of mental or motor function progressively appears because temporary or persistent damage to the cranial nerve occurs due to various causes. Although there are about 70 or more types of diseases reported as a degenerative brain disease, among the diseases, dementia, Alzheimer's disease, Parkinson's disease, frontotemporal degenerative disease, or the like are representatively well known.

Among them, dementia is one of the diseases with a high prevalence rate, and cerebral cortex dysfunction occurs in memory, attention, language functionality, visuospatial ability, and the like, so that patients with dementia suffer great difficulty in leading daily and social lives.

Although the cause of dementia has not been exactly revealed, Alzheimer's disease (AD) caused by the accumulation and entanglement of β-amyloid (Aβ) protein in the brain during aging, vascular dementia caused by cerebral arteriosclerosis, alcoholic dementia, and the like have been pointed out as the causes of dementia. Among them, dementia caused by Alzheimer's disease is the most common at 60% or more, and Alzheimer's disease is characterized by histological findings such as brain atrophy occurring in the brain cortex or hippocampus, senile plaque, neurofibrillary tangles and granulovacuolar degeneration of nerve cells, and Hirano bodies. Aβ is a major component of senile plaque, and Aβ deposition is presumed to be an important cause of the development of Alzheimer's disease.

Alzheimer's disease (AD) symptoms are associated not only with cytotoxicity due to β-amyloid (Aβ) deposition, but also with synaptic disorders of the cholinergic nervous system. Dysfunction of the cholinergic nervous system has been known to contribute to memory and cognitive dysfunction of Alzheimer's patients. The basal nucleus of Meynert cholinergic neurons in the forebrain are associated with memory and cognitive abilities along with the temporal lobe, hippocampus, and amygdala, and it is known that in the brains of Alzheimer's patients, nerve cells are reduced to 78% in the temporal lobe, 60% in the hippocampus, and 67% in the basal nucleus of Meynert. When brain cells are damaged by cytotoxicity, the transmission of information, that is, the metabolism of neurotransmitters is impaired, thereby causing memory and cognitive dysfunction. Already, many researchers have consistently reported that acetylcholine (ACh) and an enzyme involved in the synthesis thereof (choline acetyltransferase) are observed to be selectively reduced in Alzheimer's disease. Furthermore, it is known that in the brains of patients with Alzheimer's disease, not only the nicotinic acetylcholine receptor and muscarinic acetylcholine receptor are decreased, but also the reabsorption of choline and the secretory function of acetylcholine deteriorate compared to the brain function of normal people.

To date, most of the drugs officially approved as therapeutic agents for dementia by the FDA and the like have targeted dementia caused by Alzheimer's disease, but the point of action of the drug is limited to acetylcholinesterase. However, suppression of this enzyme only plays a role in making it possible to lead a normal life by suppressing a decrease in acetylcholine, and is not a method of treating the underlying cause of dementia. In addition, there is a drug therapy using an N-methyl-D-aspartate (NMDA) receptor antagonist, but the drug therapy is also based on the decrease in ACh in patients with Alzheimer's disease and is likewise not a fundamental treatment method. In other words, there is still no drug capable of bringing the patient back to a normal state by fundamentally reversing the cause of dementia.

DISCLOSURE

Technical Problem

An aspect is to provide a composition for preventing or treating a degenerative brain disease, comprising 2-pentylfuran or a solvate thereof, a stereoisomer thereof or a pharmaceutically acceptable salt thereof.

Another aspect is to provide a health functional food for preventing or alleviating a degenerative brain disease, comprising 2-pentylfuran or a solvate thereof, a stereoisomer thereof or a pharmaceutically acceptable salt thereof.

Other objects and advantages of the present application will be apparent from the detailed description along with the accompanying claims and drawings. The contents not described in the present specification can be sufficiently recognized and inferred by those skilled in the art or similar fields of the present application, and thus, the description thereof will be omitted.

Technical Solution

One aspect is to provide a composition for preventing or treating a degenerative brain disease, containing 2-pentylfuran or a solvate thereof, a stereoisomer thereof or a pharmaceutically acceptable salt thereof as an active ingredient.

The 2-pentylfuran may be represented by the following Chemical Formula 1.

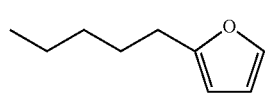

[Chemical Formula 1]

As used herein, the term "stereoisomer" refers to a molecule which has the same chemical formula and the same bond order between constituent atoms, but has a different three-dimensional structure, and is divided into an enantiomer and a diastereomer. Further, the stereochemical isomer form of the pyridone derivative compound according to an exemplary embodiment is defined as all possible compounds that the compound of Chemical Formula 1 may have. Unless otherwise mentioned or indicated, the chemical name of a compound refers to a mixture of all possible stereochemical isomer forms, the mixture comprising all diastereomers and enantiomers of a basic molecular structure. In particular, a stereocenter may have an R- or S-configuration, and a substituent on a divalent cyclic (partially) saturated radical may have a cis- or trans-configuration. A compound including a double bond may have E or Z-stereochemistry at the double bond. The stereochemical isomer form of the compound represented by Chemical Formula 1 is intended to be included in the scope of the present invention.

As used herein, the term "pharmaceutically acceptable" refers to a composition which is suitable for use in contact with tissues of a subject (for example: a human) and within the scope of the sound medical judgment because its benefit/risk ratio is reasonable without excessive toxicity, irritation, allergic reactions or other problems or complications.

As the term "salt" used herein, an acid addition salt formed by a pharmaceutically acceptable free acid is useful. The acid addition salt is obtained from inorganic acids such as hydrochloric acid, nitric acid, phosphoric acid, sulfuric acid, hydrobromic acid, hydroiodic acid, nitrous acid or phosphorous acid, and nontoxic organic acids such as aliphatic mono- and dicarboxylates, phenyl-substituted alkanoates, hydroxyalkanoates and alkanedioates, aromatic acids, aliphatic and aromatic sulfonic acids. Such pharmaceutically nontoxic salts may include sulfates, pyrosulfates, bisulfates, sulfites, bisulfites, nitrates, phosphates, monohydrogen phosphates, dihydrogen phosphates, metaphosphates, pyrophosphates, chlorides, bromides, iodides, fluorides, acetates, propionates, decanoates, caprylates, acrylates, formates, isobutyrates, caprates, heptanoates, propiolates, oxalates, malonates, succinates, suberates, sebacates, fumarates, maleates, butene-1,4-dioates, hexane-1,6-dioates, benzoates, chlorobenzoates, methyl benzoates, dinitrobenzoates, hydroxybenzoates, methoxybenzoates, phthalates, terephthalates, benzenesulfonates, toluenesulfonates, chlorobenzenesulfonates, xylenesulfonates, phenyl acetates, phenyl propionates, phenyl butyrates, citrates, lactates, β-hydroxybutyrates, glycolates, malates, tartrates, methanesulfonates, propanesulfonates, naphthalene-1-sulfonates, naphthalene-2-sulfonates or mandelates, but are not limited thereto.

The acid addition salt may be prepared by typical methods, for example, dissolving the compound represented by Chemical Formula 1 or 2 in an excess aqueous acid solution, and precipitating this salt using a water-miscible organic solvent, for example, methanol, ethanol, acetone or acetonitrile. Further, the acid addition salt may also be prepared by evaporating the solvent or excess acid from this mixture, and then drying the mixture or suction-filtering a precipitated salt.

In addition, a pharmaceutically acceptable metal salt may be prepared using a base. An alkali metal or alkaline earth metal salt may be obtained by, for example, dissolving the compound in an excess alkali metal hydroxide or alkaline earth metal hydroxide solution, filtering the non-soluble compound salt, evaporating the filtrate, and drying the resulting product. In this case, preparing a sodium, potassium or calcium salt as the metal salt is pharmaceutically suitable. A silver salt corresponding thereto may be obtained by reacting an alkali metal or alkaline earth metal salt with a suitable silver salt (for example, silver nitrate).

As used herein, the term "degenerative brain disease" may include one or more from the group consisting of Alzheimer's disease and other types of dementias, Parkinson's disease (PD)-related disorders, a prion disease, a motor neuron disease, Huntington's disease, amyotrophic lateral sclerosis, Niemann-Pick disease, spinal muscular atrophy, spinocerebellar ataxia and stroke. Depending on the relationship between the cause of degenerative brain disease and the components, the pharmaceutical composition may be used as an active material for preventing and treating a degenerative brain disease.

As used herein, the term "prevention" refers to all actions that suppress a degenerative brain disease or delay the onset of the disease by administering the pharmaceutical composition according to the present invention.

As used herein, the term "treatment" refers to all actions in which symptoms of degenerative diseases are ameliorated or beneficially altered by administering the pharmaceutical composition according to the present invention.

In other exemplary embodiments, 2-pentylfuran may activate microglia or increase phagocytosis by the microglia. More specifically, the removal of a material (for example, (β-amyloid) which induces a degenerative brain disease is increased by the increased phagocytosis. In general, the material which induces a degenerative brain disease may be β-amyloid. Without being limited by a particular theory, microglia surrounding β-amyloid in the brain may increase immunoreactivity and may increase phagocytosis of beta-amyloid, and therefore, it has been reported that such phagocytosis can treat and ameliorate a degenerative brain disease by reducing β-amyloid (Olibera M. Mitrasinovic et al. Accelerated Phagocytosis of Amyloid by Mouse and Human Microglia Overexpressing the Macrophage Colony-stimulating Factor Receptor, THE JOURNAL OF BIOLOGICAL CHEMISTRY, Vol. 277, No. 33, 1p.). Therefore, 2-pentylfuran according to an exemplary embodiment can be usefully used for a degenerative brain disease including dementia by activating phagocytosis of microglia to reduce β-amyloid.

As used herein, the term "microglia" refers to a cell which performs a primary immune function in the central nervous system as a neuroglial cell of the central nervous system. Microglia serve to support tissues, supply necessary materials to nerve cells, and carry, destroy, and remove materials in tissues, and have different properties depending on whether they are activated or not.

As used herein, the term "activated microglia" refers to microglia after activation of the microglia, and activation of microglia, when microglia, which originally maintain the shape of elongated branches and thin cell bodies, detect toxins introduced from the outside or generated inside, transforms microglia into an activated shape having thick and short branches and thick cell bodies in order to protect nerve cells from these toxins. Unlike microglia in a normal state, the activated microglia activate phagocytosis, proliferate cells, and produce inflammation mediators by expressing genes such as cytokines such as TNF-α, IL-1β and IL-6, chemokines, inducible nitric oxide synthase (iNOS) and cyclooxygenase-2 (COX-2). Activation of microglia has an aspect of removing damaged cells and protecting nerve cells from invading bacteria and viruses from the outside, and also has another aspect of simultaneously damaging nerve cells when the microglia are over-activated.

Examples of an activator of the microglia may include lipopolysaccharide (LPS), which is a bacterial endotoxin, Interferon-γ, β-amyloid, a ganglioside, 2-pentylfuran, and the like, and may be 2-pentylfuran in an exemplary embodiment.

As used herein, the term "phagocytosis" may also referred to as an endocytic action, macrophage action, phagocytic action, phagocyte action, and phagocytosis action, and may mean a phenomenon in which a specific cell takes up solid particles from an environment and digests the solid particles intracellularly. The specific cell may be a reticulocyte, a histiocyte, a vascular epithelial cell, an astrocyte, a lymphocyte, a leukocyte, and microglia. In an embodiment of the present invention, the specific cell may be preferably microglia. The solid particles may be impurities such as bacteria, viruses and cell residues. In an embodiment of the present invention, the solid particles may preferably be a material which induces a degenerative brain disease. Microglia activated by 2-pentylfuran may activate phagocytosis and remove materials which induce a degenerative brain disease by such phagocytosis.

The pharmaceutical composition may include a pharmaceutically acceptable carrier in addition to an active ingredient. In this case, the pharmaceutically acceptable carrier is typically used during formulation, and includes lactose, dextrose, sucrose, sorbitol, mannitol, starch, acacia rubber, calcium phosphate, alginate, gelatin, calcium silicate, microcrystalline cellulose, polyvinylpyrrolidinone, cellulose, water, syrup, methylcellulose, methyl hydroxybenzoate, propyl hydroxybenzoate, talc, magnesium stearate, mineral oil, and the like, and is not limited thereto. Furthermore, the pharmaceutically acceptable carrier may further include a lubricant, a wetting agent, a sweetening agent, a flavoring agent, an emulsifier, a suspending agent, a preservative, and the like in addition to the above ingredients.

The pharmaceutical composition may be administered orally (oral preparation) or parenterally (for example, applied intravenously, subcutaneously, intraperitoneally or topically as an injection) according to a desired method, and may be administered subcutaneously (that is, a skin external preparation) or orally (that is, an oral preparation), but is not limited thereto.

As a buffer added to the various dosage forms, it is preferred to use an isotonic, non-irritating buffer with a pH of 4 to 9 of a pH of 5 to 9. The dose varies depending on the patient's condition and body weight, severity of the disease, drug form, administration route, and duration, but may be suitably selected by those skilled in the art.

The pharmaceutical composition may be administered in a pharmaceutically effective amount. The term "pharmaceutically effective amount" means an amount sufficient to treat diseases at a reasonable benefit/risk ratio applicable to medical treatment, and an effective dosage level may be determined according to factors including the type of diseases of patients, the severity of disease, the activity of drugs, sensitivity to drugs, administration time, administration route, excretion rate, treatment period, and simultaneously used drugs, and other factors well known in the medical field. Another pharmaceutical composition of the present invention may be administered as an individual therapeutic agent or in combination with other therapeutic agents, may be administered sequentially or simultaneously with therapeutic agents in the related art, and may be administered in a single dose or multiple doses. It is important to administer the composition in a minimum amount that can obtain the maximum effect without any side effects, in consideration of all the aforementioned factors, and this amount may be easily determined by the person skilled in the art.

An effective amount of the pharmaceutical composition may vary depending on the age, gender, condition, and body weight of a patient, the absorption of the active ingredients in the body, inactivation rate and excretion rate, disease type, and the drugs used in combination, and may be generally in a range of 0.1 to 500 mg per 1 kg of a body weight, and the pharmaceutical composition may be administered daily or every other day or may be dividedly administered once to five times a day. However, since the effective amount may be increased or decreased depending on the administration route, the severity of obesity, gender, body weight, age, and the like, the dose is not intended to limit the range thereof in any way.

Another aspect provides a health functional food for preventing or alleviating a degenerative brain disease, including one compound of the compounds described above, a solvate thereof, a stereoisomer thereof or a nutraceutically acceptable salt thereof.

As used herein, the term "alleviation" refers to all actions that at least reduce a parameter associated with an abnormal condition, for example, the degree of symptoms. In this case, in order to prevent or alleviate a degenerative brain disease, the health functional food composition may be used individually or simultaneously with a medicament for treatment prior to the onset stage of the corresponding disease or after the onset of the corresponding disease.

More specifically, the alleviation in the present specification may include reduction of a material which induces a degenerative brain disease by enhancing activation of microglia, and thus increasing phagocytosis, when a health functional food including 2-pentylfuran is ingested.

The food composition may be used by adding an active ingredient as it is to food or may be used together with other foods or food ingredients, and may be appropriately used by a typical method. The mixing amount of the active ingredient may be suitably determined depending on its purpose of use (for prevention or alleviation). In general, when a food or beverage is prepared, the composition of the present invention is added in an amount of 60 wt % or less, preferably 40 wt % or less based on the raw material. For long-term intake for the purpose of health and hygiene or for the purpose of health control, however, the amount may be below the above-mentioned range.

Other ingredients to be added are not particularly limited, except that the food composition contains the active ingredient as an essential ingredient at an indicated ratio, and the food composition may contain various flavoring agents, natural carbohydrates, and the like as an additional ingredient as in a typical beverage. Examples of the above-described natural carbohydrates include typical sugars such as monosaccharides, for example, glucose, fructose and the like; disaccharides, for example, maltose, sucrose and the like; and polysaccharides, for example, dextrin, cyclodextrin and the like, and sugar alcohols such as xylitol, sorbitol, and erythritol. As the flavoring agent except for those described above, a natural flavoring agent (thaumatin, a stevia extract (for example, rebaudioside A, glycyrrhizin and the like), and a synthetic flavoring agent (saccharin, aspartame and the like) may be advantageously used. The proportion of the natural carbohydrate may be appropriately determined by the choice of a person skilled in the art.

The food composition may contain various nutrients, vitamins, minerals (electrolytes), flavoring agents such as synthetic flavoring agents and natural flavoring agents, colorants and fillers (cheese, chocolate, and the like), pectic acid and salts thereof, alginic acid and salts thereof, organic acids, protective colloid thickeners, pH adjusting agents, stabilizers, preservatives, glycerin, alcohols, carbonating agents used in a carbonated beverage, or the like, in addition to the additives. These ingredients may be used either alone or in combinations thereof. The ratio of these additives may also be appropriately selected by a person skilled in the art.

Each description and embodiment disclosed in the application may also be applied to different descriptions and embodiments, respectively. That is, all combinations of various elements disclosed in this application fall within the scope of the present application. Further, the scope of the present application is not limited by the specific description described below.

Advantageous Effects

2-Pentylfuran according to an aspect or a solvate, stereoisomer or pharmaceutically acceptable salt thereof has an effect of removing a material which induces a degenerative brain disease, and thus can be used as an active material capable of replacing existing therapeutic agents because it is possible to prevent or treat the degenerative brain disease.

DESCRIPTION OF DRAWINGS

FIG. 1 is an image illustrating that the top color heat maps show residence frequencies after a control media (Ctrl) and culture supernatants (Sup) in which Streptococcus pneumoniae intraperitoneally (IP) injected into mice in three different amounts ($10^4$, $10^5$, and $10^6$ colony forming units (CFUs)) is introduced. The total moving distance values were quantified under the same conditions (10/condition at n=5). ($P<0.05$; , $P<0.01$; and *, $P<1.0\times10^{-3}$).

FIG. 2 shows the mRNA expression levels of pro- (Tnf, Il6, Il1b) and anti-inflammatory cytokines (Il10, Il13) in microglia, which are measured in the cerebral cortex treated with Sup and IP injected.

FIG. 3 shows the mRNA expression levels of pro-(Tnf, Il6, Il1b) and anti-inflammatory cytokines (Il10, Il13) in astrocytes, which are measured in the cerebral cortex treated with Sup and IP injected.

FIG. 4 is a set of images illustrating protein amounts of cytokines, which are measured in primary microglia treated with Sup prepared in four different Streptococcus pneumoniae administration amounts (1, 10, 100, and 1000 multiplicity of infection (MOI); n=5/condition). (Tnf, IL6, IL1b). ($P<0.05$; , $P<0.01$; and *, $P<1.0\times10^{-3}$)

FIG. 5 is a set of representative fluorescence images showing that a GFP intensity reflects the morphology of Ctrl- and Sup-treated microglia. The images show microglia present in the cerebral cortex after IP injection of Ctrl or Sup into CX3CR1$^{GFP/-}$ mice. Scale bar: 20 um. GFP intensity was quantified under the following two conditions (n=3 to 5 mice/condition).

FIG. 6 is a set of images showing the amount of $O_2^-$ accumulated after production after treatment with Ctrl and Sup, which are measured at intervals of 1 minute for 25 minutes. Data is expressed as mean±SEM at each time point.

FIG. 7 is a set of images showing primary microglia that have migrated due to Ctrl or Sup. The images were made using a Boyden chamber assay. The chemotaxis index indicates the quantified number of migrated microglia (n=5/condition).

FIG. 8 shows the distribution of primary microglia of fluorescein isothiocyanate (FITC)-dextran measured by fluorescence activated cell sorting (FACS) analysis after treatment with Ctrl or Sup. The phagocytosis index represents mean fluorescence intensities (MFIs) (n=5 condition).

FIG. 9 is a set of images showing chemotaxis analysis and ROS production. ($P<0.05$; , $P<0.01$; and *, $P<1.0\times10^{-3}$)

FIG. 10 is a set of images showing chemotaxis analysis, and phagocytosis after Ctrl, Sup and flow-through (FT) treatment. ($P<0.05$; , $P<0.01$; and *, $P<1.0\times10^{-3}$)

FIG. 11 is an image showing that odorant receptors are expressed in primary microglia according to the mRNA-seq data.

FIG. 12 is an image showing the relative expression levels of odorant receptors induced by treatment with Sup.

FIG. 13 is a set of images showing that the relative luciferase activity (y-axis) of Olfr110 and Olfr111 was measured at increasing concentrations of 11 furan analogues.

FIG. 14 is an image showing the relative luciferase activity by comparing of Olfr110 and Olfr111 to candidate metabolites.

FIG. 15 is an image showing the relative luciferase activity of Olfr111.

FIG. 16 is an image showing a circular map describing the molecular acceptance ranges of Olfr110 and Olfr111 for 11 furan analogues. An analogue located at the center means the most reactive analogue, and an analogue located at the outermost periphery means the least reactive analogue.

FIG. 17 is an image showing a structural model of a 2-PF-Olfr110 polymer assembly showing four definitive residues (F102, F104, Y252, and Y259) for the interaction of 2-PF with Olrf110.

FIG. 18 is a set of images showing the relative luciferase activity (y-axis) of the wild-type Olfr110 and nine Olfr110 mutants (shown in the legend) measured with an increasing concentration of 2-PF (x-axis).

FIG. 19 shows images of Hana3A cells expressing MOCK, Olfr110, or Olfr111 migrating to 2-PF (top). The images were made using a Boyden chamber assay. The chemotaxis index showing the number of migrated microglia was measured after treatment with a control solvent (NT) and 2-PF at concentrations of 10, 100, 1000 um (n=5/condition).

FIG. 20 is a set of images showing ion chromatograms (EICs) extracted for 2-PF precursor ions (m/z=153.091) obtained from LC-MS/MS datasets for synthetic 2-PF, Sup, and control media (Ctrl).

FIG. 21 is a set of images showing MS/MS spectra of 2-PF precursor ions in synthetic 2-PF and Sup. fragmented ions of 2-PF precursor ions, shown with their corresponding structures, as predicted by HMDB (Wishart et al., 2007).

FIG. 22 is a set of images showing an EIC for 2-PF precursor ions in Sup after the addition of $10^2$ and $10^4$ uM 2-PF.

FIG. 23 is an image showing a cytotoxic assay.

FIG. 24 is an image showing an assay of active oxygen.

FIG. 25 is an image showing an assay of phagocytosis. Phagocytosis was measured after treating Sup with control media (Ctrl) and ATP, or with an increasing concentration of 2-PF (0, 100, 300, or 500 uM) (see text).

FIG. 26 is an image showing the olfactory epithelium (OE) and olfactory bulb (OB) used as positive controls, along with western blot analysis of primary microglia and astrocyte Olfr110. B-actin was used as a loading control.

FIG. 27 is a set of images showing a co-immunostaining analysis showing the expression of Olfr110 (red) and Iba-1 (green) in the cerebral cortex (upper panel). Microglial marker; expression of Olfr110 and GFAP (green) in the hippocampus (middle panel), microglial marker; expression of Olfr110 and NeuN (green) in the cerebral cortex (lower panel), a neuronal cell marker. DAPI is shown in blue. Scale bar: 50 um.

FIG. 28 is a set of images an immunostaining analysis showing the expression of Olfr110 (red) in GFP(+)microglia (green) in the CX3CR1$^{GFP/+}$ cerebral cortex. The left and right panels show low and high resolution images. Scale bar: 50 um (left) and Scale bar: 20 um (right).

FIG. 29 is a set of images showing an immunostaining analysis showing the expression of Olfr110 measured after treatment with PBS (Ctrl) and 2-PF (lower panel) along with control media (Ctrl) and Sup (upper panel). The expression level of Olfr110 was quantified by the intensity of red.

FIG. 30 is a set of heat maps showing the residence frequency of mice after IP injection of a PBS solvent and 2-PF at three different concentrations. The total migration distance was quantified under the same conditions and displayed on a bar graph.

FIG. 31 is a graph showing the mRNA expression levels of inflammatory cytokines measured in the cerebral cortex after IP injection of 2-PF.

FIG. 32 is a set of fluorescence images showing the intensity of GFP in microglia after injection of the control or 2-PF into CX3CR1$^{GFP/+}$ mice, produced by microglia of the cerebral cortex.

FIG. 33 is a set of time-lapse confocal microscopic images formed by measuring cerebral cortex slices at 1, 16, 25, 40, and 92 minutes, respectively after treatment the control or with 2-PF. The volume of microglia is shown in green, and the protruding parts during phagocytosis are represented by arrows.

FIG. 34 is a graph showing the degree of mRNA expression of inflammatory cytokines of primary microglia transfected with non-targeting siRNA+Mock (siCtrl), siRNA against Olfr110+Mock (siOlfr110), and siRNA against Olfr110+the rescue vector (Rescue) after 2-PF pretreatment. (*, P<0.05; , P<0.01; and *, P<0.001)

FIG. 35 is a set of graphs showing the protein levels of Tnf and Il16 after 2-PF treatment measured in a culture supernatant.

FIG. 36 is a set of graphs showing the amount of accumulated oxygen produced in primary microglia when siRNA transfection was performed after treatment with 2-PF.

FIG. 37 is a set of graphs showing the distribution of primary microglia with FITC-dextrin intensity measured by FACS analysis after siRNA transfection. FIG. 37 is as described in FIG. 36. The phagocytosis index indicates the quantified average fluorescence intensity.

FIG. 38 is a set of images showing primary microglia at three different concentrations of 10, 100, and 1000 μM 2-PF.

FIG. 39 is a representative brain image showing transfected microglia (yellow). Non-microglia are shown in red, and non-transfected microglia are shown in green. The area shown by an asterisk is a part of the cerebral cortex of a CX3CR1$^{GFP/+}$ mouse after stereotactic injection.

FIG. 40 is a graph of measuring the mRNA expression levels of Olfr110 and Olfr111. The mRNA expression levels were measured after injection of non-targeting siRNA+Mock+siGLO (Ctrl); Olfr110 siRNA+Mock+siGLO (siOlfr110); or Olfr110 siRNA+rescue vector+siGLO (Rescue), respectively. (*, P<0.05; , P<0.01; and *, P<0.001)

FIG. 41 is a set of images showing the distribution of beads in three types of cells in the brain of a CX3CR1$^{GFP/+}$ mouse. Beads are indicated by white dots, and microglia are indicated by yellow dots. Beads were counted at 6 positions in 3 independent mice under 3 conditions, and the counted beads were displayed as a bar graph. (*, P<0.05; , P<0.01; and *, P<0.001)

FIG. 42 is an image showing the DEGs relationship between the microglia of the control and experimental group. Each number means a DEG number.

FIG. 43 is an image of a heat map showing loge-fold-changes of the up-regulated (red) and down-regulated (green) genes.

FIG. 44 is a graph showing that GOBPs are enriched by up-regulated genes in 2-PF-treated microglia.

FIG. 45 is a graph showing the cAMP production of microglia (n=5/condition) treated at different concentrations (0, 100, and 500 μM) in groups treated with SQ22536 (adenylyl cyclase inhibitor) or not.

FIG. 46 is a graph showing cAMP produced in primary microglia after treatment with 2-PF at the same concentration. (n=5/condition)

FIG. 47 is an image showing an increased calcium concentration inside the microglia measured by fura-2AM calcium imaging. High concentrations are shown in red and low concentrations are shown in green.

FIG. 48 is a set of images showing the western blot results of phosphorylated ERK (pERK), p38 (pp38), JNK (pJNK) and Akt (pAkt) measured in primary micronerve cells using western blot analysis at 0, 2, 5, 10, 20 and 30 minutes after treatment with 2-PF and LPS. β-actin was loaded.

FIG. 49 shows the concentrations of Tnf and 116 secreted from primary glial cells after pretreatment with 2-PF. The graph is divided into a group pretreated with adenylyl cyclase (SQ: SQ22536) and a group not pretreated with adenylyl cyclase (SQ: SQ22536).

FIG. 50 is a graph showing the amount of active oxygen produced under the same experimental conditions as in FIG. 49.

FIG. 51 is a graph showing the degree of phagocytosis under the same experimental conditions as in FIG. 49.

FIG. 52 is a set of images showing the migrated microglia, and at the same time, is a graph showing cytotoxicity under the same experimental conditions as in FIG. 49. (n=5)

FIG. 53 is a set of graphs showing the amounts of ERK, phosphor-ERK (pERK), CREB, and phosphor-CREB (pCREB) measured in primary microglia by western blot after pre-culture with SQ22536 or pd98059 and treatment with 2-PF. (*, P<0.05; , P<0.01; and *, P<0.001)

FIG. 54 is a graph showing an increase in concentration of 2-EF co-treated with 300 μM of 2-PF on the x-axis and the relative luciferase activity of Olfr110 on the y-axis. (*, P<0.05; , P<0.01; and *, P<1.0)

FIG. 55 is a graph of active oxygen production generated in primary microglia treated with 2-EF-treated Sup and 2-EF-untreated Sup, respectively (Left). FIG. 55 is a graph of active oxygen production generated in primary microglia treated with 2-EF Sup co-treated with 500 μM of 2-PF and Sup treated with 2-EF not co-treated with 500 μM of 2-PF, respectively (Right). (*, P<0.05; , P<0.01; and *, P<1.0) The Tukey's post-hoc modification method was used with ANOVA.

MODES OF THE INVENTION

Hereinafter, the present invention will be described in more detail through Examples. However, these Examples are provided only for exemplarily describing the present invention, and the scope of the present invention is not limited to these Examples.

REFERENCE EXAMPLES. EXPERIMENTAL MATERIALS AND EXPERIMENTAL PREPARATION

1. Culture of Microglia and Astrocytes

In the present example, microglia or astrocytes were primarily extracted from the cerebral cortex of E18.5 mouse embryos (Tamashiro et al., 2012) and then cultured as in Example 1. More specifically, the cortex of mouse embryos was collected and then stored in a cold supernatant (#14170-112; Thermo Fisher Scientific) and pretreated at 37° C. in a 0.25% trypsin solution (#15090-046; Thermo Fisher Scientific) for 20 minutes. Then, cells were plated in a minimal nutrient medium supplemented with 10% FBS (#SH30919.03; Hyclone), 2 mM L-glutamine (#25030-081; Thermo Fisher Scientific), 0.04% glucose (#G7021; Sigma Aldrich), and 1% penicillin/streptomycin (#15140-122; Thermo Fisher Scientific), and then filtered using a 40 μm strainer (#352340; Thermo Fisher Scientific). Microglia were plated at a density of $1.2 \times 10^7$ cells in a T75 flask coated with poly-D-lysine (#P7280; Sigma Aldrich). After 2 hours, the mixture was transferred to a Dulbecco's modified eagle medium (DMEM; #SH30243.01; Hyclone), and the medium was replaced every 3 days for 2 weeks. In order to separate the microglia from this mixed solution, first, the mixed solution was shaken at 37° C. at 150 rpm for 2 hours, then the mixed solution containing microglia was separately extracted from the top and transferred, and then the microglia were isolated by centrifugation at 1300 rpm at room temperature for 5 minutes. The isolated microglia were transferred to a culture medium. After the microglia were transferred, the microglia were completely removed by shaking the remaining mixed solution at 160 rpm for 1 day for culturing. Then, astrocytes were isolated by treatment with 0.25% trypsin and again cultured in a T75 flask for 4 days for collection. The purity of the collected microglia and astrocytes was evaluated by qRT-PCR analysis and by immunocytochemistry using Iba-1 and Gfap, which are a marker gene and a protein, respectively.

2. Selection of 2-pentylfuran from *Streptococcus pneumoniae* Culture Solution Two encapsulated serotype strains (D39 *S. pneumonia*, Kim et al., 2015) were cultured with 30 g of sterilized Todd Hewitt Broth (#249240; BD Biosciences) and 0.5% yeast extract (#288620; BD Biosciences). Subsequently, the grown bacteria were transferred to THY broth and cultured at 37° C. for 24 to 48 hours to a concentration of $10^8$ CFU/ml. The culture solution was maintained at 4° C. at 4,000× g and centrifuged for 10 minutes to isolate a culture supernatant (Sup), and the culture supernatant was used for intraperitoneal injection (IP). In order to isolate a fraction including metabolites, the culture solution was further filtered using an Ultracel YM-3 membrane (3 kDa pore, Millipore Corporation, Bedford, MA.). In addition, a synthetic 2-PF solution of 98% purity (purchased from St. Louis, MO, USA) was prepared for the experiment, and then an equal amount of methanol was added to the solution to make a mixed solution. $10^2$ or $10^4$ 2-pentylfuran was added to Sup, and the resulting product was treated with 0.1% TFA.

3. Preparation of Animal Model

All mice were maintained and managed according to protocols approved by DGIST's Animal Care Ethics Committee, under standard temperature control, laboratory conditions, or conditions with free access to colored tunnels, mazes, climbing materials, and running wheels. In both in vivo and ex vivo experiments, 8- to 10-week-old BL6J or heterozygous $CX3CR1^{+/GFP}$ mice were used. The mice were generated by cross-breeding C57/BL6J with $CX3CR1^{GFP/GFP}$. All mice were randomly provided with sterile food and water at room temperature on a 12-hour cycle.

4. Method of Performing qRT-PCR

For the measurement of mRNA, RNA was isolated from red blood cells, microglia, astrocytes, Hana3A cells, or cerebral cortical cells using the MagNa Lyser (Roche Molecular Diagnostics) using TRIzol reagent (Invitrogen, Carlsbad, CA.) according to the manufacturer's protocol. Then, cDNA was generated through reverse transcription using the isolated mRNA (using PrimeScript™ 1st str and cDNA Synthesis kit—#6110; Takara Bio Inc). This process was quantitatively measured in real time through quantitative real-time-PCR (using LightCycler® 480 SYBR Green I Master). The measured values were calculated using the 2-ΔΔCt method.

5. Method of Performing Cytokine ELISA Assay

The expression levels of Tnf, il6, and Il1b cytokines secreted from microglia were measured according to the manufacturer's protocol. More specifically, the expression levels were measured by ELISA 24 hours after treatment with 2-PF or a cell supernatant. The ELISA kit was purchased from BD Biosciences (#DY410 for Tnf; #DY406 for Il6; #DY401 for Il1b).

6. Quantitative Morphological Analysis Method

In order to analyze morphological changes in microglia activation, 9-week-old $CX3CR1^{GFP/-}$ mice were used. Two hours after an IP containing or not containing 2-PF was injected into two mice, brain sections were collected by cryosection. After a 40 μm-thick brain tissue fragment was prepared to be smaller than 1 μm, a GFP signal of microglia was measured using a 40-fold magnification confocal microscope. A GFP-pixel signal of microglia was analyzed using Zeiss ZEN Software (Zeiss).

7. Method of Measuring Superoxide ($O_2^-$) Concentration

Superoxide concentrations were calculated by measuring the degree of decrease in cytochrome c using a VersaMax microplate reader (Babior et al., 1973). Microglia were cultured on a 96-well plate at a concentration of $1.0 \times 10^5$ cells/well, and the microglia were activated by a 10 μM ATP solution containing 2-pentylfuran and cytochrome c, or a solution of Sup mixed with cytochalasin B (5 μM; #C66762; Sigma Aldrich). The resulting ROS concentration was measured by changes in light absorption at 550 nm at intervals of 1 minute for 25 minutes.

8. Method of Measuring Cell Chemotaxis

Cell chemotaxis was measured using a multiwell Boyden chamber. More specifically, a polycarbonate filter (8 μm pore; #101-8; Neuroprobe) was coated with 10 mg/ml fibronectin in PBS (Sigma-Aldrich) for 2 hours, and the coated filter was placed in a Boyden chamber. In addition, the bottom side of the plate was filled with serum-free DMEM containing 2-pentylfuran or a culture supernatant. Next, microglia or Hana3A cells were transfected with an odorant receptor structure and then suspended in serum-free DMEM. Subsequently, microglia and Hana3A cells were allowed to stand at 37° C. for 4 hours and 8 hours, respectively. Cells sinking to the bottom were fixed with 4% PFA, and stained with hematoxylin for 10 minutes. Fixed cells were counted under an optical microscope in 5 randomly selected fixed magnetic fields (200×) using a scored eyepiece. The chemical chemotaxis index was defined as the number of migrating cells using an untreated group as a standard.

9. Method of Measuring Phagocytosis

Primary microglia were cultured for 24 hours after being seeded in a 24-well plate ($5 \times 10^5$ cells/well). Cells were pre-cultured with 2-PF or Sup for 30 minutes, transferred to FITC-dextran (1 mg/ml, 20 mg/ml in PBS; #FD70S; Sigma Aldrich) in serum-free DMEM at 37° C. for 30 days, and washed with PBS at 4° C. Cells were detached by 0.25% trypsin in PBS (#15090-046; Thermo Fisher Scientific) and the detached cells were analyzed by FACS Accuri™ C6 (BD Biosciences). Mean fluorescence intensity (MFI) was calculated by integrating fluorescence histograms under each condition using the aforementioned software. The phagocytosis index was defined as MFI using an untreated group as a standard.

10. Method of Measuring Active Oxygen Concentration

Active oxygen levels were measured using 2',7'-dichlorodihydrofluorescein diacetate (DCF-DA, #D6883; Sigma Aldrich) using a method that had undergone minor modifications from the existing method. (Bae et al., 2001). More specifically, the primary microglia were treated with 10 μM DCF-DA in a 24-well plate ($5.0 \times 10^5$ cells/well) for 24 hours at a temperature of 37° C. for 30 minutes. One plate was treated with 2-PF and one was not. Cells in each well were measured by a flow cytometer (FACS Accuri™ C6; BD Biosciences). MFI was measured in the same manner as described above.

11. Odorant Receptor Cloning and Cell Surface Expression Measurement

Full-length odorant receptor genes from mouse and human genomic DNA were amplified using appropriate primers. After the resulting cDNA was digested with a restriction enzyme, the product was ligated to produce an odorant receptor structure having a restriction enzyme site in a pME18S expression vector containing N-terminal Lucy, Flag, and Rho tags as described above. The structure of all odorant receptors was confirmed by sequence analysis (Shepard et al., 2013). Next, Hana3A cells were transfected with RTP1S, and their location and presence on the cell membrane were confirmed as previously described (Behrens et al., 2009; Zhuang and Matsunami, 2008). Such transfection was performed using Lipofectamine 2000 (#11668-019; Thermo Fisher Scientific) according to the manufacturer's instructions. More specifically, the transfected cells were grown on a coverslip (#0101050; Marienfeld) coated with poly D lysine (10 μg/ml; #P7280; Sigma Aldrich). Next, the cells were washed with a warm PBS solution and cooled with ice for 30 minutes to block endocytosis. After being washed with cold PBS, the cells were fixed with ice-cold methanol and acetone for 2 minutes (v/v=1:1) (Methanol: #106009; MERCK, Acetone: #179124; Sigma Aldrich). The cells were then incubated with normal horse serum (#008-000-121; Jackson ImmunoResearch) at room temperature for 1 hour. The resulting cells were incubated with mouse anti rhodopsin (anti-Rho; 1:1,000; #MABN15; Millipore) or rabbit anti Olfr110 (#ab177327; Abcam) at 4° C. overnight. After being washed with PBS, the cells were treated with a Cy3-conjugated donkey anti-mouse antibody (1:1,000; #715-165-150; Jackson ImmunoResearch), an Alexa488-conjugated donkey anti-mouse antibody (1:1,000; #715-545-150; Jackson ImmunoResearch), or a Cy3-conjugated donkey anti-rabbit antibody (1:1,000; #711-165-152; Jackson ImmunoResearch) at room temperature for 1 hour. The cells were mounted with a Vectashield fluorescent mounting medium containing DAPI (#H-1200; Vector Laboratories). The expression of heterologous odorant receptors was analyzed with a confocal laser scanning microscope LSM700 and ZEN software (Zeiss).

12. Luciferase Assay Measurement Method

The Dual-Glo luciferase assay system (#E2940; Promega) was used for odorant receptor ligand screening. More specifically, Hana3A cells were streaked and spread on a white polystyrene 96-well plate (#353296; BD Biosciences) one day before transfection. pCRELuc (1 μg; #219076; Agilent Technologies), pRL-SV40 (1 μg; #E2231; Promega), RTP1S (1 μg), and OR (6 μg; or Mock) vectors were transfected for 24 hours in each plate. Each plate was analyzed using Lipofectamine 2000 (#11668-019; Thermo Fisher Scientific) according to the manufacturer's protocol. Transfected cells were stimulated in CD293 medium (#11913-019; Thermo Fisher Scientific) at 37° C. for 4 hours using diluted odorants at various concentrations. The activity of luciferase was normalized by the activity of Renilla luciferase. The amount of light emitted was measured using a SpectraMax L microplate reader (Molecular Devices).

13. Homology Modeling Method

Olfr110/111 mouse odorant receptor homology modeling includes a template search, alignment of gene sequences, model determination, model quality evaluation, and the like. Further, this was performed by SWISS-MODEL, which is a web-based homology modeling tool. The amino acid sequence of Olfr110/111 was first obtained from NCBI Protein BLAST using the UniprotKB/Swiss-Prot database. BLAST and HHblits of the SWISS-MODEL Template Library (SMTL) were used for template searchs for Olfr110/111. As a result, 179 and 186 templates were found. The X-ray crystal structure of a human adenosine A2A receptor (resolution: 2.7 Å, PDBID: 3VG9) was selected as a template structure to construct a homology model for Olfr110/111, which is based on both sequence identity and similarity. The 3d homology model structure was generated using Promod. A QMEAN scoring function was used for the overall evaluation of the generated model. The final 3D model structure of Olfr110/111 was downloaded from the SWISS-MODEL website.

14. Modeling Method of Receptor-Ligand Molecular Binding

A two-dimensional structure of a ligand was generated by ChemBioDraw (ver. 11.0.1) and transferred to Chem3D Pro (ver. 11.0.1) to generate a three-dimensional structure. The procedure used for ligand preparation and optimization was performed using the 'Sanitize' protocol (default) of SYBYL-X 2.1.1 (Tripos Inc., St. Louis). The homology model of Olfr110/111 (template structure PDB ID: 3VG9) was generated using the SWISS-MODEL homology modeling tool. The structural preparation frequency of SYBYL-X 2.1.1 was also used in the protein preparation process. The deletion of amino acid residues was corrected, and a hydrogen atom was further added to the protein using a TRIPOS force field. Then, in the POWELL method (Abagyan et al., 1994), the initial optimization setting was changed from the default setting to 'none', and then the protein minimization process was performed. The EHgks termination gradient was set to 0.5 kcal/(mol*Å), and the maximum iteration was set to 1000 times. Next, the entire docking process was performed using the protein and ligand prepared by the above method using the Surflex-Dock GeomX module (SYBYL-X 2.1.1). The docking site was induced by the Surflex-Dock protomol, which is an ideal ligand phenotype, characterized by all interactions with existing binding sites. This protocol was defined by jointly selecting and finding the receptor that is most widely expressed on the multi channel surface of SYBYL-X 2.1.1. Two protocol generation factors, Bloat and Threshold, were set to 0.5 (Å) and 0, respectively. The maximum value of the generated poses was set to 20, and the minimum RMSD between the generated forces was set to 20. The minimum value of RMSD between poses was set to 0.05. Other docking factors of Surflex-dock GeomX were set to the default values.

15. Site-Specific Mutagenesis

Specific mutant vectors of the Olfr110 structure were generated using PfuUltra High-Fidelity DNA polymerase (#600380; Agilent Technologies). All mutant vectors (F102W; F104W; Y252F; Y259F; F102W/F104W; Y252F/Y259F; F102W/Y252F/Y259F; F104W/Y252F/Y259F; F102W/F104W/Y252F/Y259F) were sequenced in forward and reverse directions (Macrogen).

16. Sample Preparation

A synthetic 2-PF solution (purity of 98% or higher) was purchased from Sigma Aldrich (St. Louis, MO, USA). An equal amount of absolute (99.9%) methanol was added to the original 2PF solution. The original 2-PF solution and the methanol-added solution (2-PF+CH$_3$OH) were analyzed by direct infusion mass spectrometry. For liquid-chromatography-tandem-mass-spectrometry (LC-MS/MS) analysis of synthetic 2-PF, a 2-PF+CH$_3$OH solution was used. For LC-MS/MS analysis of Sup and Control media (Ctrl), proteins were removed by filtering Sup or Ctrl (1 ml) through an Ultracel YM-3 membrane with a processing size of 3 kD (Millipore Corporation, Bedford, MA). 500 µl of a flow-through was mixed with an equal volume of methanol. The resulting sample was sonicated for 10 minutes and centrifuged at 14,000 g at 4° C. for 20 minutes (Lau et al., 2015). The supernatant was analyzed by LC-MS/MS (FIGS. 3A and 3B). In addition, each of $10^2$ and $10^4$ uM 2-PF was added to Sup. The resulting sample was acidified with 0.1% trifluoroacetic acid (TFA), and then analyzed by LC-MS/MS.

17. Direct Infusion with HESI Source

2-PF and 2-PF+CH$_3$OH samples were injected into a heated electric spray ionization source at a flow rate of 20 µl/minute using a 500 µl gas-tight syringe. Furthermore, measurement was performed for 8 minutes by a single ion monitoring method of a Q Exactive Hybrid Quadrupole-Orbitrap mass spectrometer. In addition, the capillary voltage was set to 3.5 kV (positive mode) and the temperature of a solvent removal capillary was set to 250° C. Next, the entire MS was monitored in a mass range between 50 and 750 Thomsons (Th) with a resolution of 70,000 (m/z 200). The maximum ion injection time was 100 ms and the automatic gain control value was 1×10$^6$. An isolation window was set to 1.0 m/z (Looβe et al., 2015).

18. LC-MS/MS Analysis Method

Thermo EASY-nLC 1000 (Thermo Scientific, Odense, Denmark) equipped with an analytical column (Thermo Scientific, Easy-Column, 75 µm×50 cm) and a trap column (75 µm×2 cm) was used for LC separation. Parameters used herein are as follows: injection volume=10 µl; operation temperature of the analytical columns=50° C.; flow rate=300 nL/min; and mobile phase A=0.1% formic acid and mobile phase B=0.1% formic acid and 2% water in acetonitrile. For LC separation, the following concentration gradient was used for 50 minutes: 2% to 40% solvent B for 36 minutes, 40% to 80% solvent B for over 6 minutes and 80% to 2% solvent B for over 6 minutes. Samples eluted from the LC were analyzed using a Q-Exactive™ hybrid quadrupole-Orbitrap mass spectrometer (Thermo Scientific) equipped with a nanoelectrospray device. The capillary voltage was set to 3.5 kV (positive mode), and the capillary temperature was set to 250° C. Further, Q-Exactive was set to a data dependent mode, and a 50 to 750 Th mass range scan was performed at 70,000 resolution (at m/z 200). As a result of the experiment, the top 10 ions detected the most were isolated at 1.0 m/z. In addition, it was confirmed that the ions are fragmented due to collisions with high energy. MS scans were detected with a resolution of 17,500 (Saigusa et al., 2016). The maximum ion injection time was 100 ms and 50 ms for full MS and MS/MS scans, respectively. The automated gain control target values were set to 1.0×10$^6$ and 1.0×10$^5$ for full MS and MS/MS scans, respectively.

19. Extracted Ion Chromatogram (EIC) and MS/MS Spectra Measurement Method

The precursor ions of 2-PF were extracted from the raw data obtained using full MS scans including full MS and MS/MS scans (m/z=153.091 Da). The precursor ions were extracted by setting chromatographic peaks to 17 and 22 or 16 and 22 within a tolerance of 2 ppm. In each spectrum, the peaks of m/zf—the mass of CH$_3$ and the corresponding ones were connected, and as a result, a candidate structure was obtained with fragmented peak ions (HMDB) (Wishart et al., 2007).

20. Western Blot Method

Cells and tissues were prepared using the T-PER® reagent (#78510; Thermo Fisher Scientific) with protease inhibitors (#04-693-116-001; Roche Molecular Diagnostics), DMSF (Sigma-Aldrich) and lysed using the MagNA Lyser (Roche Molecular Diagnostics). A total protein extract was quantified by the Bradford assay. The sample was dissolved in 7.5% SDS-PAGE or 4 to 20% gradient mini-PROTEIN TGX Precast Gels (#456-1064; Bio-Rad Laboratories), and then blotted onto nitrocellulose membranes (#10600002; GE Healthcare). The membrane was then blocked in 5% skimmed milk powder, TBST, 0.1% TWEEN® 20 (#P9416; Sigma-Aldrich) and Tris-buffered saline for 1 hour, and then incubated with primary antibodies at 4° C. overnight. The antibodies are as follows: Olfr110 (36 kDa; 1:1,000; #ab177327; Abcam), anti rhodopsin (39 kDa; 1:1,000; #MABN15; Millipore), CREB (43 kDa; 1:1,000; #9197; Cell Signaling Technology), phospho-CREB (43 kDa; 1:1, 000; #9198; Cell Signaling Technology), ERK (44 kDa; 1:1,000; #sc094; Santa Cruz), phospho-ERK (42, 44 kDa; 1:1,000; #sc-7383; Santa Cruz), phospho-Akt (60 kDa; 1:500; sc-293125; Santa Cruz), phospho-JNK (46, 54 kDa; 1:500; sc-6254; Santa Cruz), phosphor-p38 (38 kDa; 1:1, 000; sc-7973; Santa Cruz), or beta-Actin (45 kDa; 1:10,000; #4967; Cell Signaling Technology). Furthermore, an iso-type-matched horseradish peroxidase-conjugated secondary antibody was used at 1:100,000 with anti-rabbit in TBST (#711-035-152; Jackson ImmunoResearch) and 1:40,000 with anti-mouse (#715-035-150; Jackson ImmunoResearch) at room temperature for 2 hours. As an immunoreactive protein band, SuperSignal™ West Pico Chemiluminescent Substrate (#34080; Thermo Fisher Scientific) was used.

21. Immunostaining

For immunofluorescence staining, a 22 mm coverslip (#0101050; Marienfeld) was coated with poly-D-lysine (10 μg/ml; #P7280; Sigma Aldrich) under standard conditions for 48 hours, and then microglia were cultured. Thereafter, the cells were washed with PBS and fixed in 4% paraformaldehyde (#6148; Sigma Aldrich) for 5 minutes. Subsequently, the cells were cultured in PBS containing 4% normal horse serum (#008-000-121; Jackson ImmunoResearch) and 0.1% TWEEN® 20 (#P9416; Sigma-Aldrich) at room temperature for 1 hour. Then, the cells were blocked at 4° C. overnight with the primary antibodies listed below. The antibodies are as follows: Olfr110 (rabbit-anti-Olfr110; 1:10,000; #ab177327; Abcam), Iba-1 (goat-anti-Iba-1; 1:1, 000; #ab5076; Abcam), and GFAP (mouse-anti-GFAP; 1:1, 000; #556330; BD Biosciences). Samples were cultured with secondary antibodies in PBS including 0.1% TWEEN® 20 (#P9416; Sigma-Aldrich) at room temperature for 1 hour. The secondary antibodies as follows: Cy3-conjugated donkey anti-rabbit (1:1,000; #711-165-152; Jackson Immuno-Research), Alexa488-conjugated donkey anti-goat (1:1, 000; #705-545-147; Jackson ImmunoResearch), or Alexa488-conjugated donkey anti-mouse (1:1,000; #715-545-150; Jackson ImmunoResearch). Thereafter, the cells were mounted with a Vectashield fluorescent material containing DAPI (#H-1200; Vector Laboratories), and then the images resulting from the experiment were obtained using a confocal laser scanning microscope and using LSM700 and ZEN software (Zeiss).

22. Immunohistochemistry

Mice were anesthetized at a dose of 400 mg of ketamine/kg body weight, perfused epidurally and then fixed with paraformaldehyde (PFA; #6148; Sigma Aldrich) in 4% PBS. The brains of mice were transferred to 4% PFA at 4° C. for 4 hours, and then stored in a 30% sucrase solution for 1 day. After the brains were washed with an O.C.T compound (#4583; Scigen), a sample was formed by cutting the brain to a thickness of 40 μm using a cryotome (#HM 550; Thermo Fisher Scientific). The brain samples were stored on slides, and simultaneously immersed in 2% donkey serum in 0.3% PBST (1×PBS/0.3% Triton X-100) for 30 minutes and then cultured with primary antibodies in a blocking buffer at 4° C. overnight. The primary antibodies are as follows: rabbit anti-Olfr110; 1:10,000; #ab177327; Abcam, goat anti-Iba-1; 1:1,000; #ab5076; Abcam, mouse anti-GFAP; 1:1, 000; #556330; BD Biosciences)

For the next step, that is, the knockdown and rescue experiment, slides were cultured with secondary antibodies in PBST. The secondary antibodies are as follows: Cy3-conjugated donkey anti-rabbit 1:1,000; #711-165-152; Jackson ImmunoResearch, Alexa488-conjugated donkey anti-mouse; 1:1,000; #715-545-150; Jackson ImmunoResearch, Alexa488-conjugated donkey anti-goat (1:1,000; #705-545-147; Jackson ImmunoResearch). Next, stained slides were treated with a Vectashield fluorescent material containing DAPI (#H-1200; Vector Laboratories). An image obtained as a result of the experiment was shown as a 20-fold magnification image using a confocal laser scanning microscope LSM700 (Zeiss).

23. Knockdown and Rescue Experimental Method

The primary microglia of mice were placed in a 6-well plate one day before transfection. Subsequently, to differentiate the primary microglia, Lipofectamine RNAiMAX (#13778150, Themo Fisher Scientific) in Opti-MEM (#11058021; Thermo Fisher Scientific) was used according to the manufacturer's protocol. Further, the cells were cultured using 100 nM Olfr110 siRNA (#LQ-064350-01-0002; 4 sets of ON-TARGET+mouse Olfr110 siRNA; #1: CCU-GUAAUUUAUACGCUAA; #2: CGUUAAGGUACU-CAUUUAU; #3: CUGAAUGAAUUGCAGUAUU #4: GAUUGAUCUCAGUGCUGUA, Dharmacon) or 100 nM non-targeting siRNA (UGGUUUACAUGUCGACUAA, Thermo Fisher Scientific) for 24 hours. siRNA delivery efficiency was confirmed using a siGLO Red oligonucleotide duplex (#D-001630-02-05, Thermo Fisher Scientific). Thereafter, the siRNA #3 rescue vector of Olfr110 with several silent homozygous mutations (5'-CU-CAACGAGCUGCAAUACC-3') was generated using the mentioned site-directed mutagenesis method, and then transfected for Olfr110 knockdown for 24 hours. In the rescue vector experiment, the rescue vector used Lipofectamine LTX (#15338100; Thermo Fisher Scientific) according to the manufacturer's protocol, and was transfected into cells transfected with non-targeting siRNA or siRNA #3 for 24 hours.

24. Ex Vivo Knockdown and Rescue Experimental Method

After a 9-week-old CX3CR1$^{GFP/+}$ male mouse was anesthetized with ketamine, a small hole (about 1 mm in diameter) was drilled into the skull, and a stereotaxic injection accessing the brain was performed (bregma −0.11 mm, 1 mm left spot from longitudinal fissure). According to the manufacturer's protocol, 0.5 μl of siRNA (665 ng) with a Mock vector (in the case of knockdown) or a rescue vector (in the case of recovery) and 0.5 μl of a siGLO red oligonucleotide duplex (133 ng, #D-001630-02-05, Thermo Fisher Scientific) were injected into the cerebral cortex using Lipofectamine RNAiMAX. Injection was performed at a rate of 0.5 μl/min using a Hamilton syringe. 48 hours after injection, an ex vivo imaging analysis method was performed with a slight modification to the above-described method (Takayama et al., 2016). The delivery of the siRNA structure could be confirmed by the red fluorescence of the siGLO RED oligonucleotide duplex. Further, the efficiency of transfection at the injection site could also be confirmed using qRT-PCR.

25. mRNA-Sequencing and Data Analysis

After treatment with a vehicle (control), Sup (MOI 100) or 2-PF (100 µM) for 2 hours, total RNA was isolated from $2 \times 10^6$ primary microglia using a RNeasy mini Kit (Qiagen, 74104) and analyzed using a Qubit RNA HS assay kit (Thermo Fisher Scientific, Q32852) according to the manufacturer's standard protocol for quantification. The RNA integrity number (RIN) of each sample was measured using an Agilent Technologies 2100 BioAnalyzer, and the RIN of all samples was 8.5 or more, which is suitable for mRNA sequencing. Full-length cDNA was generated using a SMARTer-Seq v4 Ultra Low input RNA Kit (Clontech, 634888) according to the manufacturer's recommended protocol. The synthesis of the first strand of cDNA was initiated by adding 1 µl of 3 'SMART CDS primer II A from 10 ng of total RNA at 72° C. for 3 minutes. The second strand was synthesized by adding SMARTer-seq v4 oligo and SMART-Scribe reverse transcriptase, and the reactant was incubated at 42° C. for 90 minutes and then inactivated at 70° C. for 10 minutes. Double-stranded cDNA was amplified for 8 cycles by PCR and purified using Agencourt AMPure beads (Beckman, A63881). An mRNA-seq library was created using a Nextera XT DNA library preparation kit (Illumina, FC-131-1024) according to the manufacturer's protocol. The cDNA was subjected to tagmentation (simultaneous fragmentation and tagging with a sequencing adaptor) and amplified by PCR using Index Primers of a Nextera XT DNA Index Kit (Illumina, FC-131-1001). After PCR, the DNA library was purified using AMPure beads and the quality was evaluated using an Agilent 2100 Bioanalyzer. The DNA library of individual samples was quantified using a KAPA library quantification kit (KAPA biosystems, KK4854) and then pooled. All libraries were sequenced on the Illumina Hiseq2500 instrument to generate dual-indexed 100 bp paired reads, thereby generating an average of 58 million reads for each sample. The quality of the raw sequences was confirmed using FastQC (Babraham Bioinformatics), and the adapter sequences were cleaned up using cutadapt software. The remaining reads were aligned to the mouse reference genome (GRCm38) using TopHat (Trapnell et al., 2009) with default options. Then, the aligned reads were assembled into the annotated genes, and fragments per kilobase per million mapped reads FPKM were calculated using Cufflinks (Trapnell et al., 2010).

26. Selection of Differentially Expressed Genes

On average, 58 million pieces of data were collected from each sample, and 89.9% of the data aligned to the mouse's reference genome. Genes with FPKM>1 in at least one sample have been shown to be expressed as previously described (Graveley et al., 2011). After the FPKM values of each sample were collected, quantum normalization (Bolstad et al., 2003) was applied to the FPKM values converted to $\log_2$. To identify DEGs, these normalized values were compared as follows using previously reported integrated statistical tests (Lee et al., 2010). The comparison is to compare Sup-treated samples with Control (Sup) and compare 2-PF-treated samples and Control (2-PF). First, a Student's t-test was performed for each gene to obtain a T-value, and then a random sampling experiment was performed 1,000 times, and Gaussian kernel density estimation was applied to the T value obtained by the experiment performed 1,000 times. An empirical null distribution for T values was generated. In addition, for each gene, the corrected P value of the observed T-value was calculated using the empirical distribution by a two-tailed test. DEGs were identified as genes with a corrected P value of less than 0.05 and an absolute $\log_2$-median-ratio>cutoff ($\log_2$ fold change=0.41 and 0.54 for Sup vs. control, 2-PF vs. control).

The cutoff was determined as the mean of the 5th and 95th percentile values in the distribution of loge fold changes obtained in the random sampling experiment described above. Enrichment analysis of a Gene Ontology Biological Process (GOBP) was performed using DAVID software (Huang da et al., 2009). As a result, the enriched GOBP was P<0.05 calculated from DAVID and the count was ≥3.

27. cAMP ELISA Assay

Primary microglia were inoculated into 48 well plates ($2 \times 10^5$ cells/well) and treated with 30 µM forskolin (#F3917, Sigma Aldrich), or 2-PF (10, 100, 500 µM) for 30 minutes. In order to confirm the effect of an inhibitor, 1 mM SQ22536 (#17318-31-9; Calbiochem) was first pretreated for 30 minutes. The cells were lysed in a solution of 0.1 M of HCl with 1% Triton X 100 for 10 minutes, and the lysate was centrifuged at 600×g for 2 minutes. The supernatant was directly used for cAMP analysis using a cAMP ELISA kit (Enzo Life Science) according to the manufacturer's protocol. The optical density at 405 nm was measured using a VersaMax microplate reader (Molecular Devices).

8. Calcium Imaging

The newly isolated microglia were placed on poly-D-lysine-coated 18-mm aperture microscope cover glasses (#0111580; Marienfeld), and after 24 hours, the microglia were cultured in a superfusion chamber for 30 minutes. The chamber contained 4 µM of Fura-2/AM ($Ca^{2+}$-sensitive fluorescent dye; #F1221; Thermo Fisher Scientific) in a 0.22 µm-filtered Ringer's solution (115 mM NaCl, 2.5 mM KCl, 1 mM $CaCl_2$, 1.5 mM $MgCl_2$, 4.5 mM HEPES, pH 7.4). After calcium staining culture, the chamber was placed under an inverted microscope and rinsed with Ringer's solution for 20 minutes before treatment with 3-PF. In this case, the flow rate of the solution is 12 ml/min. Next, the primary microglia were treated with 300 µM ATP (#A2383; Sigma Aldrich) for 5 seconds. After being washed for 5 minutes, the primary microglia were treated with a 2-pentylfuran solution at a concentration of 100 µM for 5 seconds. This step was performed with a 2-pentylfuran solution at two concentrations (300 and 1000 µM). Finally, the primary microglia were treated with a 300 µM ATP solution for 5 seconds. The emitted fluorescent material was photographed using a CCD camera every 2 seconds. Pseudo-color images were converted using fractional fluorescence changes (ΔF/F, Δ[$Ca^{2+}$]i). Furthermore, these images show changes in intracellular calcium ions. The color intensity of the captured images was set to a maximum of 1.5±0.1 AU (arbitrary linear units) and a minimum of 0.4±0.1 AU. A representative calcium ion peak was selected after analyzing 160 cells.

29. Chemicals and Inhibitors

The chemicals used in this experiment were purchased from Sigma-Aldrich. All purchased compounds are as follows: Acetic acid (#695092), acetone (#W332607), 2 aminoacetophenone (#W390607), dimethyl sulfide (#471577), ethanol (#E7023), hexanal (#115606), hydrogen sulfide (#742546), indole (#W259306), isopentanol (#320021), 2-pentylfuran #W331708), trimethylamine (#W324108), furan (#185922), 2-methylfuran (#M46846), 2,3-dimethylfuran (#428469), 2-ethylfuran (#W367303), 2-propylfuran (#P1488; Tokyo Chemical Industry, TCI), 2-butylfuran (#CDS001204), 2-t-butylfuran (#386278), 2-hexylfuran (#H26698; Alfa Aesar), and 2-heptylfuran (#A10604; Alfa Aesar) (#D2650; Sigma Aldrich) diluted in DMSO. ATP (#A2383; Sigma Aldrich) was diluted in DMSO. Inhibitors of the adenylyl cyclase, PKA, ERK, G, and PLC pathways were diluted in DMSO according to the following concentrations: pd98059 50 µM (#PHZ1164; Thermo Fisher Scientific), 300 µM SQ22536 (#568500; Calbiochem), 5 µM U73122 (#662035; Calbiochem), 10 µM H-89 (#tlrl-h89; InvivoGen), and 10 µM Gallein (#371709; Calbiochem. Further, each inhibitor was pretreated one hour before the experiment.

30. Statistical Analysis

All data in this experiment was expressed as mean±SEM. Statistical significance was determined by an unpaired Student's t-test method for comparing repeated measurements and respective control values using the GraphPad Prism 5 Software package (GraphPad Software Inc.).

Example 1. Confirmation of Activation of Microglia of Metabolites by *S. pneumoniae*

Disease behavior is known to be one of the symptoms caused by the excessive secretion of cytokines (Dantzer et al., 2008). In this experiment, after a *S. pneumoniae* culture solution was intraperitoneally injected into a mouse, the mobility of the mouse was measured to confirm the induction of disease behavior and the response. Among the responses occurring in mice, changes in intake, changes in body weight, or changes in body temperature corresponded to immediate responses. The inventors focused on the amount of change in the mobility of the mouse (Dantzer et al., 2008). It was confirmed that the mobility of the mouse significantly decreased (P<0.01) after the intraperitoneal injection, and this change also had a significant dependence on the injection amount (see FIG. 1). Conversely, it was observed that there was no symptom shown in the case of mice intraperitoneally injected with the control. It is known that the symptom and disease behavior are caused by excessive secretion of cytokines in the immune system (KKonsman et al., 2002). The cytokine mRNA levels in the cerebral cortex were measured and compared to confirm whether cytokines were actually secreted in mice. In this case, as an analysis method, quantitative real-time polymerase chain reaction (qPT-PCR) was used. In the experimental group, when the secretion of inflammatory and non-inflammatory cytokines in the cerebral cortex by intraperitoneal injection was compared with that of the control, it could be confirmed that all the secretions significantly increased ($P<1.0\times10^{-3}$) (see FIG. 2). It is known that both microglia and astrocytes, after infection, secrete pro- and anti-cytokines, respectively (Norden et al., 2016). When the present inventors intraperitoneally injected microglia and astrocytes, it was investigated whether the cytokine secretion was increased preferentially in either case. As a result, a significant ($P<1.0\times10'$) increase in the mRNA secretion of five cytokines was confirmed in microglia. Tnf, Il6, Il1b, Il10, and Il13 cytokines were all increased during microglia injection, but not by astrocyte injection (see FIG. 3). Further, it could also be confirmed that the increase in Tnf, Il16, and Il1b was also dose-dependent (see FIG. 4).

In addition, it is known that the activation of microglia causes a morphological change from an existing divided form to an amoeba form, and simultaneously increases the number of stages and the length of each cell (Kreutzberg, 1996). The present inventors compared the intensity of GFP in CX3CR1$^{GFP/+}$ mice using a control and microglia-specific tagged GFP to confirm the morphological change as described above. As a result, it could be confirmed that the intensity of GFP was significantly higher ($P<1.0\times10^{-3}$) in the group in which microglia were injected intraperitoneally when compared to that of the control. This means that the injection of 2-PF causes activation of microglia, and this activation increases the number and length of microglia (See FIG. 5). In addition, it can be confirmed that as time passes, microglia are activated and their shapes change. This is a change from the existing divided form to the amoeba form. Furthermore, it could be seen that the GFP intensity of the microglia in the experimental group injected with Sup was significantly higher ($P<1.0\times10'$) than that of the control. Therefore, it can be concluded that the activation of microglia occurs and morphological changes also occur after the injection of 2-pentylfuran (see FIGS. 6 to 8).

As a result, it was confirmed that small molecules derived from *S. pneumoniae* increase cytokine secretion and increase phagocytosis (see FIGS. 9 and 10) and induce activation of microglia, which leads to morphological changes of microglia.

Example 2. Confirmation of Interaction between 2-pentylfuran and microglia Olfr110

The present inventors hypothesized that metabolites released from *S. pneumoniae* can induce activation of microglia by binding to odorant receptors. In order to primarily determine odorant receptor candidates, mRNA sequencing analysis of primary microglia was performed. As a result, it could be confirmed that 13 discovered odorant receptors were Olfr111, Olfr110, Olfr482, Olfr99, Olfr132, Olfr115, Olfr77, Olfr543, Olfr461, Olfr455, Olfr1420, Olfr1417, and Olfr57, and among them, Olfr111/110 was the most expressed (see FIG. 11). In addition, seven odorant receptors (Olfr110, Olfr111, Olfr99, Olfr1029, Olfr433, Olfr222, and Olfr920) expressed in microglia were additionally found using a gene phenotype database (GSE52564; (Zhang et al., 2014). These seven odorant receptors include Olfr111/110 and are specifically expressed in microglia compared to other cells. By integrating these processes, a total of 17 candidate receptors were found.

Furthermore, many receptors which recognize patterns associated with pathogens are also induced by pathogen infections for an effective immune response (Wornle et al., 2006). Therefore, the present inventors first investigated whether 17 odorant receptor candidates were derived from primary microglia after treatment with Sup using qRT-PCR. As a result, it could be confirmed that the treatment with Sup increased Olfr110/111 the most, followed by Olfr920, Olfr1417, and Olfr99 (see FIG. 12). Next, it was investigated whether these five candidate odorant receptors react with the volatile molecules of Sup.

Through mRNA-sequencing analysis of microglia, 11 volatile metabolites (Olfr111, Olfr110, Olfr482, Olfr99, Olfr132, Olfr115, Olfr77, Olfr543, Olfr461, Olfr455, Olfr1420, Olfr1417, and Olfr57) derived from *S. pneumoniae* were selected. After it was confirmed that candidate odorant receptors were immediately infected using these 11 types of metabolites and activated, reactivity was confirmed using a luciferase assay (Zhuang and Matsunami, 2008) together with Hana3A cells. It was confirmed that the candidate odorant receptor exhibited a particularly strong reactivity to 2-PF among the 11 metabolites. The remaining three receptors also showed higher reactivity to ethanol, but also responded to MOCK, which appears to be a non-specific reaction. Therefore, these results mean that Olfr110/111 can act as a selective ligand for 2-pentylfuran (see FIG. 13).

To further evaluate the 2-PF-OR, the receptors were analyzed at a molecular level. More specifically, reactivities were compared after 2-PF was treated with Olfr110/111 using a luciferase assay. These analogues included five furans such as 2-PF, 2-butylfuran, 2-t-butylfuran, 2-hexylfuran, and 2-propylfuran. All five furans showed reactivity to Olfr110/111 (see FIGS. 14 to 16). Particularly among these, 2-PF showed the highest reactivity, and particularly showed the strongest reactivity with Olfr110 (data not shown). The key residues of Olfr110 binding to 2-PF were investigated by homology modeling of Olfr110 and docking analysis between Olfr110 and 2-PF. The docking analysis predicting amino acids of Olfr110 is important for hydrophobic interactions between 2-PF and F102 and F104 in transmembrane domain 3, and Y252 and Y259 in transmembrane domain 6 (FIG. 17). Among these, it can be seen that F104 and Y252 are particularly important for odorant recognition by MOR256-3. Analysis was performed using one of the four residues (F102, F104, Y252 and Y259) predicted by a luciferase assay, or a method of inducing multiple site-directed mutagenesis. As a result, in the case of an F104W mutation, luciferase activity was completely lost, indicating that F104 plays the most important role in the interaction between 2-PF and Olfr110 (FIG. 18). After 2-PF treatment, a chemotaxis assay showed that Olfr111- or Olfr110-treated cells are increased in mobility in a concentration-dependent manner. This data shows that the interaction between 2-PF and Olfr110 can change cellular functions, for example, increase cell migration (FIG. 19).

Example 3. Confirmation of Activation of Microglia by 2-pentylfuran 3.1. Confirmation of Activation of Microglia by 2-PF Next, it was confirmed whether 2-PF is present in Sup using liquid-chromatography-tandem mass-spectrometry (LC-MS/MS) analysis. After data on 2-PF was obtained using liquid-chromatography-tandem mass-spectrometry (LC-MS/MS), a 2-PF ion precursor was confirmed using a mass-to-charge ratio (m/z=153.091). As a result, precursor ions were confirmed in Sup, but not in the control (see FIG. 20). It was also confirmed that the Sup of the synthetic 2-PF had the same MS spectrum (see FIG. 21). As a result of comparing the intensities of the 2-PF precursor ions when treated with F102 and F104, it could be confirmed that in the case of treatment with F104, the intensity increased (56.0-fold) more than the intensity in the case of treatment with F102 (see FIG. 22). This result means that 2-PF is specifically present in Sup. Further, to determine whether 2-PF induces activation of microglia in Sup, microglia were treated with 2-PF at 100, 300, and 500 μM, and microglia were primarily treated. As a result, chemotaxis (FIG. 23), active oxygen secretion (FIG. 24) and phagocytosis (FIG. 25) are significantly increased in a concentration-dependent manner ($P<1.0\times10^{-3}$).

Next, experiments were conducted on metabolites induced by 2-PF in the brains of experimental mice. It was found that Olfr110 was expressed in microglia, and it was confirmed that Olfr110 was specifically expressed in microglia, but not in olfactory tissue or astrocytes, using a western blot using an antibody (see FIG. 26).

Immunostaining confirmed strong expression in Olfr110, but not in GFAP-positive astrocytes or NeuN-positive neurons in the cerebral cortex, and GFP (+) microglia of $CX3CR1^{GFP/+}$ mice (see FIG. 28). In various cerebral regions such as the cerebral cortex and hippocampus, hypothalamus, and substantia nigra, specific Olfr110 expression in Iba-1-positive microglia was observed (data not shown). It was shown that Sup treatment induces mRNA expression of Olfr110 (FIG. 21), and increases a protein level of Olfr110 (FIG. 29, top image). Interestingly, 2-PF significantly increases an Olfr110 level ($P<1.0\times10^{-3}$) (FIG. 29, bottom image). As a pathological behavior induced by 2-PF injection, a concentration-dependent decrease in mouse mobility was shown (FIG. 30). The 2-PF injection also significantly increased an expression level of inflammatory cytokines ($P<0.05$; Tnf, Il6, Il1b, and Il10) (FIG. 31). The intensity of GFP expression in 2-PF treated $CX3CR1^{GFP/+}$ mice was also highly increased (FIG. 32). These results mean that 2-PF-induced morphological changes in microglia can lead to microglial activation. In addition, it was investigated whether 2-PF can change ex vivo phagocytosis of microglia after 2-PF culture in brain slices of $CX3CR1^{GFP/+}$ mice. Through time-lapse confocal microscopy imaging, it was seen that the capacity of microglia, a protrusion degree, and the activity of phagocytosis are increased (FIG. 33), and it was seen that, as macrophages are significantly increased ($P<1.0\times10^{-3}$), phagocytosis is also increased (FIG. 22). Taken together, this data suggests that 2-PF activates microglia in the brain.

3.2. Experiment for Increasing Disease Behavior

It is known that an increase in disease behavior by activation of microglia is due to an increase in secreted cytokines. This experiment was conducted to confirm an increase in disease behavior with an increase in cytokines. The evaluation of disease behavior was made after IP injection of Sup or 2-PF into the mice.

After IP injection, the mouse was placed in a space with four open sides (40×40×40 cm, white field, black wall), and after the position of the mouse was recorded for 30 minutes using a camera, the movement distance was calculated Thereafter, a pseudo-color heat map was drawn using Etho-Vision XT (Noldus, Netherlands).

3.3. Experiment for Increasing Ex Vivo Phagocytosis

In this experiment, in order to examine the phagocytotic action of microglia, the brain of a 9-week-old male $CX3CR1^{GFP/+}$ mouse was cut to a thickness of 150 μm using a vibratome (Leica VT1200) and then stored in an ice-cooled artificial cerebrospinal fluid (aCSF: 120 mM NaCl, 25, 25 mM $NaHCO_3$, 1.25 mM $NaH_2PO_4$, 5 mM KCl, 1 mM $CaCl_2$, 1 mM $MgSO_4$, 305mOsm glucose, pH7.4). Thereafter, the sliced brain was cultured for removal of cell debris. Oxygenated aCSF was pretreated in a perfusion chamber at 37° C. for 2 hours. Subsequently, before culture, the sliced brain was cultured with 500 μl of aCSF containing $9.10\times10^7$ microspheres (360/407 mm; #17458; Polysciences) and covered with a custom-made nylon grid. Time lapse videos were taken at intervals of 1 minute for 92 minutes using a confocal microscope. The number of phagocytosing microglia was calculated from the images.

Example 4. Whether or not Olfr110 Controls Microglial Activation by 2-PF

The present inventors tested whether the activation of microglia induced by 2-PF is mediated by Olfr110. In this experiment, a specific siRNA for Olfr110 and a specific mutant rescue vector structure of Olfr110 that restores the siRNA were designed. No. 3 of the four siRNA candidates was able to effectively reduce the mRNA and protein levels of Olfr110 in Hana3A cells. After transfection, reductions in mRNA and protein in primary microglia were confirmed, and the rescue vector restored the reductions in mRNA and protein induced by siRNA. It was confirmed that, using siRNA and a rescue vector, the effect of Olfr110 on 2-PF-induced microglial activation was able to be confirmed. First, Olfr110 knockdown reduced an increase in mRNA levels of inflammatory cytokines of primary macroglia induced by 2-PF, and conversely, the rescue vector restored the knockdown effect. In addition, a similar effect was observed at an mRNA level as well as a protein level. Increased active oxygen induced by 2-PF was reduced by siRNA, and restored by the rescue vector. However, an active oxygen increase mediated by a P2Y receptor was not affected by the presence of the rescue vector. After Olfr110 knockdown and rescue effects, similar 2-PF-induced effects on phagocytosis and chemotaxis were observed.

Next, the present inventors investigated whether Olfr110 knockdown and rescue effects occurred in mouse brains. More specifically, combinations such as non-targeting siRNA+Mock+siGLO (in the case of Ctrl), Olfr110 siRNA+Mock+siGLO (siOlfr110), and Olfr110 siRNA+rescue vector+siGLO (in the case of Rescue) were stereotactically injected into the cerebral cortex of CX3CR1$^{GFP/+}$ mice (Takayama et al., 2016). After injection, in mouse brain slices, transfected microglia (yellow) and non-transfected microglia (green), and transfected non-microglia (red) were compared and observed (FIG. 39). After microdissection of a fluorescent region of the sliced brain fragment, an expression level of Olfr110 was measured using qRT-PCR. As a result, it was observed that, after siOlfr110 injection, a significant decrease in the corresponding odorant receptor was found ($P<1.0\times10^{-3}$), and there was no change in a negative control Olfr920. The inventors observed that similar knockdown and rescue effects were also observed in the cerebral cortex of a CX3CR1$^{GFP/-}$ mouse. Taken together, it is concluded that Olfr110 can regulate the activation of microglia (cytokine secretion, secretion of active oxygen, cytotoxicity, and phagocytosis) induced by 2-PF both in vitro and ex vivo.

Example 5. Control of Olfr110-Dependent Microglial Activation Induced by 2-PF by $G_{\alpha s}$-s-cAMP-PKAERK and $G_{\beta \gamma}$-PLC-Ca$^{2+}$ Pathways In order to understand the activation of microglia through Olfr110 from a molecular point of view, in this experiment, mRNA-sequence analysis of primary microglia treated with Sup or 2-PF was performed. 1124 and 1438 differentially expressed genes (DEGs) were identified using mRNA-sequencing data (FIG. 42). It was confirmed that a significant part ($P<0.01$) of these DEGs (22.5 and 17.6% of 1124 and 1438 DEGs) includes 253 genes, and in this experiment, it was confirmed that the 253 genes are shared between both experimental groups. Among these 253 shared DEGs, 135 and 78 genes were consistently up-regulated or down-regulated in 2-PF-treated microglia, but the other 40 genes were not (FIG. 43). Next, overlapping genes which overlap upwards and downwards were investigated using gene ontology biological processes (GOBPs). The up-regulated genes are associated with microglial activity. Specific details on activation are as follows (FIG. 44): cytokine secretion (cytokine generation and secretion), chemotaxis (blood cell migration and chemotaxis), active oxygen generation (cellular responses to active oxygen and active oxygen metabolic process) and phagocytosis. This data means that both Sup and 2-PF-treated experimental groups up-regulate genes involved in microglial activation, but the down-regulated genes regulate transcription (data not shown). As a result, it was confirmed that 2-PF binding to Olfr110 is involved in microglial activation, thereby activating a signaling pathway inducing upregulation. To understand such a signaling system, it was necessary to reconstruct a network model describing interactions associated with cytokine production, chemotaxis, active oxygen generation and phagocytosis (data not shown). The newly established model revealed that cAMP, MAPK, PI3K, PLC, and Ca$^{2+}$ signaling pathways up-regulate genes involved in microglial activation, which is consistent with previous results (Verderio and Matteoli, 2001).

Next, the effects of 2-PF were examined using the established network model. For the cAMP signaling pathway, a cAMP concentration in primary microglia was measured after 2-PF treatment. As a result, cAMP treated by an adenylyl cyclase inhibitor showed that microglial activation was increased by 2-PF treatment in a concentration dependent manner (FIG. 45). Olfr110 siRNA was able to decrease cAMP production induced by 2-PF, and when the rescue vector was injected, the opposite effect was able to be obtained (FIG. 46). For a calcium signaling pathway, calcium imaging was performed after 2-PF treatment. As a result, it was confirmed that intracellular calcium ion levels increased according to an injection amount (FIG. 47). For MAPK and PI3K signaling pathways, the phosphorylation levels of ERK, p38, JNK, and Akt were measured, and it was confirmed that the phosphorylation levels after treatment increased from 2 minutes and stopped increasing at 20 minutes. Next, the relative contribution to microglial activation was investigated using the inhibitors for signaling pathways. After pretreatment with adenylyl cyclase (SQ22536), PKA (H-89), ERK (pd98059), or PLC inhibitor (U73122), 2-PF protein was treated, and Tnf and 116 cytokine levels were measured. As a result, it was confirmed that the cytokine levels showed a great decrease by SQ22536 or H-89, and a relatively less decrease by pd98059 or U73122 (FIG. 49). Particularly, U73122 completely inhibited ROS generation ($P<1.0\times10^{-3}$) (FIG. 50). It was confirmed that active oxygen generation can be similarly inhibited by gallein, which is an inhibitor of $G_{\alpha s}$s-cAMP-PKAERK and $G_{\beta \gamma}$-PLC-Ca$^{2+}$ pathways (Bonacci et al., 2006; Ukhanov et al., 2011). All inhibitors considerably decreased phagocytosis ($P<0.05$), and almost completely decreased chemotaxis ($P<1.0\times10^{-3}$). CREB and ERK phosphorylation was greatly decreased by SQ22536 and pd98059 (FIG. 53). The present study shows that the $G_{\alpha s}$-cAMP-PKA-ERK pathway regulates the production of cytokines, cytotoxicity, and phagocytosis, whereas the $G_{\beta \gamma}$-PLC-Ca$^{2+}$ pathway regulates the production of ROS.

Example 6. Selection of Competitive Inhibitors of 2-PF

There was a previous report that odorant receptors are structurally associated with an activator and an inhibitor.

Based on this, the inventors selected 2-ethylfuran (2-EF) reducing 2-PF activity by simultaneous treatment with 2-PF and derivatives which do not bind to either Olfr110 or Olfr1111 (2-methylfuran, 2,3-dimethylfuran, 2-ethylfuran, 2-hexylfuran, or 2-heptylfuran). After Olfr110 was transfected into Hana3A cells and 2-PF was fixed at 300 µM, 2-EF was treated at different concentrations from 1 µM to 10 mM, together with 2-PF, to measure competitive activity, confirming that as the 2-EF level increases, 2-PF activity decreases ($K_d$=120 µM). Consequently, active oxygen induced by 2-PF, which is an Olfr110 agonist, is decreased by 2-EF, which is its competitive inhibitor (antagonist) (FIG. 54). To confirm the microglial activity of 2-EF selected as a competitive inhibitor, 2-EF was pretreated at concentrations of 0, 100, 300, and 500 µM in primary microglia, and 100 MOI of Sup was treated, followed by measurement of an amount of active oxygen generation. As a result, it could be observed that the amount of active oxygen produced by MOI of 100 decreased as the concentration of 2-EF increased (see FIG. 55, left). Next, Sup was treated with MOI of 5, simultaneously treated with 500 µM 2-PF, and simultaneously treated with 2-ethylfuran at a concentration of 0, 100, 300, and 500 µM. Thereafter, the concentration of active oxygen was measured. As a result, active oxygen was produced by MOI 5, and the production of active oxygen was further increased by 500 µM of 2-PF (see FIG. 55, right). However, it could be confirmed that the higher the concentration of 2-EF added, the lower the concentration of active oxygen produced. This means that active oxygen was inhibited by the competitive inhibitor 2-EF.

The above-described description of the present invention is provided for illustrative purposes, and those skilled in the art to which the present invention pertains will understand that the present invention can be easily modified into other specific forms without changing the technical spirit or essential features of the present invention. Therefore, it should be understood that the above-described examples are only exemplary in all aspects and are not restrictive.

INDUSTRIAL APPLICABILITY

According to the present invention, it was confirmed that 2-pentylfuran activates microglia, and the phagocytosis by the cells increases accordingly, and from this, 2-pentylfuran or a solvate, stereoisomer, or pharmaceutically acceptable salt thereof can prevent or treat a degenerative brain disease by an effect of removing a material which induces the degenerative brain disease from the above-described result, and thus can be usefully used as an active material capable of replacing existing therapeutic agents in the field of developing a therapeutic agent for the degenerative brain disease.

The invention claimed is:

1. A method for preventing or treating a degenerative brain disease, comprising:
   administering to a subject in need thereof an effective amount of a pharmaceutical composition comprising 2-pentylfuran or a solvate thereof, a stereoisomer thereof or a pharmaceutically acceptable salt thereof as an active ingredient,
   wherein the subject requires microglial activation.

2. The method of claim 1, wherein the 2-pentylfuran is represented by the following Chemical Formula 1.

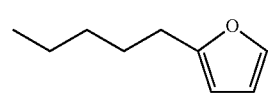

[Chemical Formula 1]

3. The method of claim 1, further comprising a pharmaceutically acceptable carrier, excipient or diluent.

4. The method of claim 1, wherein the degenerative brain disease comprises one or more from the group consisting of Alzheimer's disease and other types of dementias, Parkinson's disease (PD)-related disorders, a prion disease, a motor neuron disease, Huntington's disease, amyotrophic lateral sclerosis, Niemann-Pick disease, spinal muscular atrophy, spinocerebellar ataxia and stroke.

5. The method of claim 1, wherein the activated microglia promote phagocytosis, thereby reducing a material which induces the degenerative brain disease.

* * * * *